United States Patent
Olsen et al.

(10) Patent No.: US 7,727,278 B2
(45) Date of Patent: Jun. 1, 2010

(54) SELF FIXING ASSEMBLED BONE-TENDON-BONE GRAFT

(75) Inventors: Raymond E. Olsen, Logan, UT (US); Wesley I. Lewis, Archer, FL (US); John R. Bianchi, Gainesville, FL (US); Joe Kutsavage, High Spring, FL (US); Daniel J. Urbaniak, Aliso Viejo, CA (US); Angela Carr, Gainesville, FL (US); Ben R. Sanders, Alachua, FL (US)

(73) Assignee: RTI Biologics, Inc., Alachua, FL (US)

( * ) Notice: Subject to any disclaimer, the term of this patent is extended or adjusted under 35 U.S.C. 154(b) by 701 days.

(21) Appl. No.: 11/428,213

(22) Filed: Jun. 30, 2006

(65) Prior Publication Data

US 2006/0271192 A1 Nov. 30, 2006

Related U.S. Application Data

(63) Continuation-in-part of application No. 11/313,280, filed on Dec. 19, 2005, and a continuation-in-part of application No. 11/073,281, filed on Mar. 4, 2005, and a continuation-in-part of application No. 11/073,202, filed on Mar. 4, 2005, and a continuation-in-part of application No. 11/073,400, filed on Mar. 4, 2005.

(51) Int. Cl.
*A61F 2/08* (2006.01)

(52) U.S. Cl. .............. 623/13.12; 623/13.13; 623/13.14; 623/13.15

(58) Field of Classification Search ...... 623/13.11–13.2
See application file for complete search history.

(56) References Cited

U.S. PATENT DOCUMENTS

| D3,574 S | 7/1869 | Benedict |
|---|---|---|
| D26,174 S | 10/1896 | Bren |

(Continued)

FOREIGN PATENT DOCUMENTS

| DE | 89 14308 | 3/1990 |
|---|---|---|

(Continued)

OTHER PUBLICATIONS

Advertisement for LinX HT™ Hamstring Tendon Polymer Fastener by Innovasive Devices, Inc.

(Continued)

*Primary Examiner*—Thomas J Sweet
*Assistant Examiner*—Andrew Iwamaye
(74) *Attorney, Agent, or Firm*—McAndrews, Held & Malloy, Ltd.

(57) ABSTRACT

The present invention has multiple aspects relating to assembled self fixing bone-tendon-bone (BTB) grafts and BTB implants. A preferred application in which self fixing assembled bone-tendon-bone (BTB) grafts and implants of the present technology can be used is for ACL repairs in a human patient. In one embodiment, a self fixing BTB graft is characterized by the presence of threads along at least a portion of the exterior surface of one or both bone blocks. In another embodiment, a self fixing assembled bone-tendon-bone implant comprises a removable tendon tensioner which imparts a predetermined tension on the tendon of the BTB graft.

34 Claims, 34 Drawing Sheets

U.S. PATENT DOCUMENTS

| | | | |
|---|---|---|---|
| 3,705,586 A | 12/1972 | Sarracino | |
| D236,683 S | 9/1975 | Tegner et al. | |
| 4,034,444 A * | 7/1977 | Moertel | 24/394 |
| 4,349,921 A | 9/1982 | Kuntz | |
| 4,611,592 A * | 9/1986 | Talboy | 606/207 |
| 4,723,548 A * | 2/1988 | Lalonde | 606/150 |
| 4,744,793 A | 5/1988 | Parr et al. | |
| 4,772,286 A | 9/1988 | Goble et al. | |
| 4,781,183 A | 11/1988 | Casey et al. | |
| 4,828,562 A | 5/1989 | Kenna | |
| 4,911,710 A | 3/1990 | Milthorpe et al. | |
| 4,927,421 A | 5/1990 | Goble et al. | |
| 5,062,843 A | 11/1991 | Mahoney, III | |
| 5,067,962 A | 11/1991 | Campbell et al. | |
| 5,092,887 A | 3/1992 | Gendler | |
| 5,133,168 A | 7/1992 | Neilly et al. | |
| 5,139,520 A | 8/1992 | Rosenberg | |
| 5,147,400 A * | 9/1992 | Kaplan et al. | 623/13.18 |
| 5,171,326 A | 12/1992 | Ducheyne et al. | |
| RE34,293 E | 6/1993 | Goble et al. | |
| D336,683 S | 6/1993 | Inoue et al. | |
| 5,282,802 A | 2/1994 | Mahoney, III | |
| 5,320,115 A | 6/1994 | Kenna | |
| 5,366,457 A | 11/1994 | McGuire et al. | |
| 5,370,662 A | 12/1994 | Stone et al. | |
| 5,383,878 A | 1/1995 | Roger et al. | |
| 5,391,169 A | 2/1995 | McGuire | |
| RE34,871 E | 3/1995 | McGuire et al. | |
| 5,397,356 A | 3/1995 | Goble et al. | |
| 5,397,357 A | 3/1995 | Schmieding et al. | |
| 5,425,733 A | 6/1995 | Schmieding | |
| 5,425,767 A | 6/1995 | Steininger et al. | |
| 5,443,509 A | 8/1995 | Boucher et al. | |
| 5,454,811 A | 10/1995 | Huebner | |
| 5,496,326 A | 3/1996 | Johnson | |
| 5,531,747 A | 7/1996 | Ray | |
| 5,556,428 A * | 9/1996 | Shah | 623/13.13 |
| 5,562,669 A | 10/1996 | McGuire | |
| 5,681,314 A | 10/1997 | Derouin et al. | |
| 5,713,897 A * | 2/1998 | Goble et al. | 606/53 |
| 5,733,289 A | 3/1998 | Seedhom et al. | |
| 5,766,252 A | 6/1998 | Henry et al. | |
| 5,772,664 A | 6/1998 | DeSatnick et al. | |
| 5,800,544 A * | 9/1998 | Demopulos et al. | 623/13.13 |
| 5,846,484 A | 12/1998 | Scarborough et al. | |
| 5,888,224 A | 3/1999 | Beckers et al. | |
| 5,895,425 A | 4/1999 | Grafton et al. | |
| 5,897,570 A | 4/1999 | Palleva et al. | |
| 5,902,015 A | 5/1999 | Allcock | |
| 5,951,560 A | 9/1999 | Simon et al. | |
| 5,961,520 A | 10/1999 | Beck et al. | |
| 5,968,046 A | 10/1999 | Castleman | |
| 6,001,100 A | 12/1999 | Sherman et al. | |
| 6,019,792 A | 2/2000 | Cauthen | |
| 6,025,538 A | 2/2000 | Yaccarino, III | |
| D426,148 S | 6/2000 | Markarian | |
| 6,080,158 A | 6/2000 | Lin | |
| 6,080,192 A * | 6/2000 | Demopulos et al. | 623/13.14 |
| 6,090,998 A | 7/2000 | Grooms et al. | |
| 6,106,556 A * | 8/2000 | Demopulos et al. | 623/13.16 |
| 6,110,210 A | 8/2000 | Norton et al. | |
| 6,123,731 A | 9/2000 | Boyce et al. | |
| 6,129,762 A | 10/2000 | Li | |
| 6,179,874 B1 | 1/2001 | Cauthen | |
| 6,190,412 B1 | 2/2001 | Lee et al. | |
| 6,200,347 B1 | 3/2001 | Anderson et al. | |
| 6,270,528 B1 | 8/2001 | McKay | |
| 6,287,309 B1 | 9/2001 | Baccelli et al. | |
| 6,327,753 B1 * | 12/2001 | Rushing | 24/135 N |
| 6,368,325 B1 | 4/2002 | McKinley et al. | |
| D463,559 S | 9/2002 | Bryant et al. | |
| 6,454,770 B1 | 9/2002 | Klaue | |
| 6,482,584 B1 | 11/2002 | Mills et al. | |
| 6,497,726 B1 | 12/2002 | Carter et al. | |
| D471,085 S | 3/2003 | Markarian | |
| 6,579,295 B1 | 6/2003 | Supinski et al. | |
| 6,592,622 B1 | 7/2003 | Ferguson | |
| D479,331 S | 9/2003 | Pike et al. | |
| 6,613,278 B1 | 9/2003 | Mills | |
| 6,632,247 B2 | 10/2003 | Boyer, II et al. | |
| 6,652,592 B1 | 11/2003 | Grooms et al. | |
| 6,652,818 B1 | 11/2003 | Mills et al. | |
| 6,679,889 B1 * | 1/2004 | West et al. | 606/88 |
| 6,730,124 B2 | 5/2004 | Steiner | |
| 6,761,739 B2 | 7/2004 | Shepard | |
| 6,805,713 B1 | 10/2004 | Carter et al. | |
| 6,857,874 B2 | 2/2005 | Kim | |
| 6,890,354 B2 | 5/2005 | Steiner et al. | |
| 6,893,462 B2 | 5/2005 | Buskirk et al. | |
| 7,011,684 B2 | 3/2006 | Eckman | |
| 7,063,725 B2 | 6/2006 | Foley | |
| 7,141,066 B2 | 11/2006 | Steiner et al. | |
| D533,277 S | 12/2006 | Blain | |
| 7,169,183 B2 | 1/2007 | Liu et al. | |
| D536,453 S | 2/2007 | Young et al. | |
| 7,217,293 B2 | 5/2007 | Branch, Jr. | |
| D552,734 S | 10/2007 | Eckman | |
| D553,745 S | 10/2007 | Park | |
| 7,323,011 B2 | 1/2008 | Shepard et al. | |
| 7,351,262 B2 | 4/2008 | Bindseil et al. | |
| D583,053 S | 12/2008 | Zhukauskas et al. | |
| D583,054 S | 12/2008 | Zhukauskas et al. | |
| D583,055 S | 12/2008 | Lewis et al. | |
| D583,056 S | 12/2008 | Goede et al. | |
| D583,473 S | 12/2008 | Goede et al. | |
| D604,850 S | 11/2009 | Lewis et al. | |
| D605,768 S | 12/2009 | Zhukauskas et al. | |
| 2001/0031254 A1 * | 10/2001 | Bianchi et al. | 424/93.7 |
| 2002/0029084 A1 | 3/2002 | Paul et al. | |
| 2002/0072806 A1 * | 6/2002 | Buskirk et al. | 623/23.51 |
| 2003/0023304 A1 | 1/2003 | Carter et al. | |
| 2003/0130735 A1 * | 7/2003 | Rogalski | 623/13.15 |
| 2003/0171810 A1 | 9/2003 | Steiner | |
| 2003/0171811 A1 | 9/2003 | Steiner et al. | |
| 2003/0229394 A1 * | 12/2003 | Ogle et al. | 623/2.14 |
| 2004/0030385 A1 | 2/2004 | Steiner | |
| 2004/0102780 A1 * | 5/2004 | West, Jr. | 606/73 |
| 2004/0210308 A1 | 10/2004 | Carter et al. | |
| 2005/0015940 A1 * | 1/2005 | Stafford | 24/135 N |
| 2005/0059987 A1 * | 3/2005 | Hermann et al. | 606/157 |
| 2005/0152881 A1 | 7/2005 | Mills et al. | |
| 2005/0159812 A1 | 7/2005 | Dinger et al. | |
| 2005/0228378 A1 * | 10/2005 | Kalfas et al. | 606/61 |
| 2005/0229323 A1 | 10/2005 | Mills et al. | |
| 2007/0162124 A1 * | 7/2007 | Whittaker | 623/13.14 |

FOREIGN PATENT DOCUMENTS

| | | |
|---|---|---|
| DE | 299 22088 | 4/2000 |
| EP | 1797845 A1 | 6/2007 |
| FR | 2683715 * | 5/1993 |
| FR | 2683715 A1 | 5/1993 |
| WO | 02/064180 | 8/2002 |

OTHER PUBLICATIONS

H. Boszotta, M.D., "Arthroscopic Reconstruction of Anterior Cruciate Ligament Using BTYB Patellar Ligament in the Press-Fit Technique", Surg. Technol. Int. 11:249-253 (2003).

S.M. Schlicht and W.A. Morrison, "The Plantaris Tendon As A Tendo-Osseous Graft. Part I. An Anatomical Study", J. Hand Surg. [BR]; 17 (4): 471-5 (Aug. 1992).

W. A. Morrison and S.M. Schlicht, "The Plantaris Tendon As A Tendo-Osseous Graft. Part II. Clinical Studies" J. Hand Surg. [BR]; 17 (4): 467-70 (Aug. 1992).

H. H. Paessler, M.D., D. S. Mastrokalos, M.D., "Anterior Cruciate Ligament Reconstruction Using Semitendinosus and Gracilis Tendons, Bone Patellar Tendon, or Quadriceps Tendon-Graft with Press-Fit Fixation Without Hardware. A New and Innovative Procedure", Orthop. Clin. North Am.; 34 (1): 49-64 (Jan. 2003).

J. Dargel, R. Schmidt-Wiethoff, T. Schneider, Gert-Peter Brüggemann, J. Koebke, "Biomechanical Testing of Quadriceps Tendon-Patellar Bone Grafts: An Alternative Graft Source for Press-Fit Anterior Cruciate Ligament Reconstruction?", Arch Orthop Trauma Surg (2006) 126: 265-270.

R. Schmidt-Wiethoff, J. Dargel, M. Gerstner, T. Schneider, J. Koebke, "Bone Plug Length and Loading Angle Determine The Primary Stability of Patellar Tendon-Bone Grafts in Press-Fit ACL Reconstruction", Knee Surg. Sports Traumatol. Arthrosc (2006) 14: 108-111.

D.T. Cheung, N. Perelman, E. C. Ko, M. Nimni, "Mechanism of Crosslinking of Proteins By Glutaraldehyde III. Reaction with Collagen in Tissues", Connective Tissue Research, (1985) vol. 13, pp. 109-115, Gordon and Breach, Science Publishers, Inc. and OPA Ltd.

J. P. Van Kleunen, D. Elliott, "Effect of a Natural Crosslinking Agent (Genipin) on Tendon Longitudinal and Transverse Tensile Properties", 2003 Summer Bioengineering Conference, Jun. 25-29, Sonesta Beach Resort in Key Biscayne, FL.

E. Oberg, F. Jones, H. L. Horton, H. H. Ryffel, "Machinery's Handbook", 24th Edition, pp. 1616-1617; 1628-1633; 1652-1653; 1656-1657; 1992 by Industrial Press, Inc., New York, New York.

International Search Report corresponding to International Application No. PCT/U2007/09218, mailed Feb. 21, 2008, 5 pages.

Written Opinion of the International Searching Authority corresponding to International Application No. PCT/US2007/09218, mailed Feb. 21, 2008, 5 pages.

Non-Final Rejection corresponding to U.S. Appl. No. 11/073,400, dated Jun. 11, 2009.

Final Rejection corresponding to U.S. Appl. No. 11/073,400, dated Apr. 3, 2009.

Non-Final Rejection corresponding to U.S. Appl. No. 11/073,400, dated Sep. 8, 2008.

Final Rejection corresponding to U.S. Appl. No. 11/073,202, dated Sep. 24, 2009.

Non-Final Rejection corresponding to U.S. Appl. No. 11/073,202, dated Mar. 13, 2009.

Non-Final Rejection corresponding to U.S. Appl. No. 11/073,202, dated Aug. 5, 2008.

Final Rejection corresponding to U.S. Appl. No. 11/073,281, dated Sep. 24, 2009.

Non-Final Rejection corresponding to U.S. Appl. No. 11/073,281, dated Mar. 27, 2009.

Non-Final Rejection corresponding to U.S. Appl. No. 11/073,281, dated Aug. 5, 2008.

Examiner's Answer corresponding to U.S. Appl. No. 11/313,280, dated Oct. 16, 2009.

Interview Summary corresponding to U.S. Appl. No. 11/313,280, dated Jul. 24, 2009.

Final Rejection corresponding to U.S. Appl. No. 11/313,280, dated Mar. 27, 2009.

Non-Final Rejection corresponding to U.S. Appl. No. 11/313,280, dated Sep. 30, 2008.

Advertisement for LinX HT(TM) Hamstring Tendon Polymer fastener by Innovasive Designs, Inc.

European Search Report for European Patent Application No. 06736865.4-1526, mailed Dec. 29, 2009.

* cited by examiner

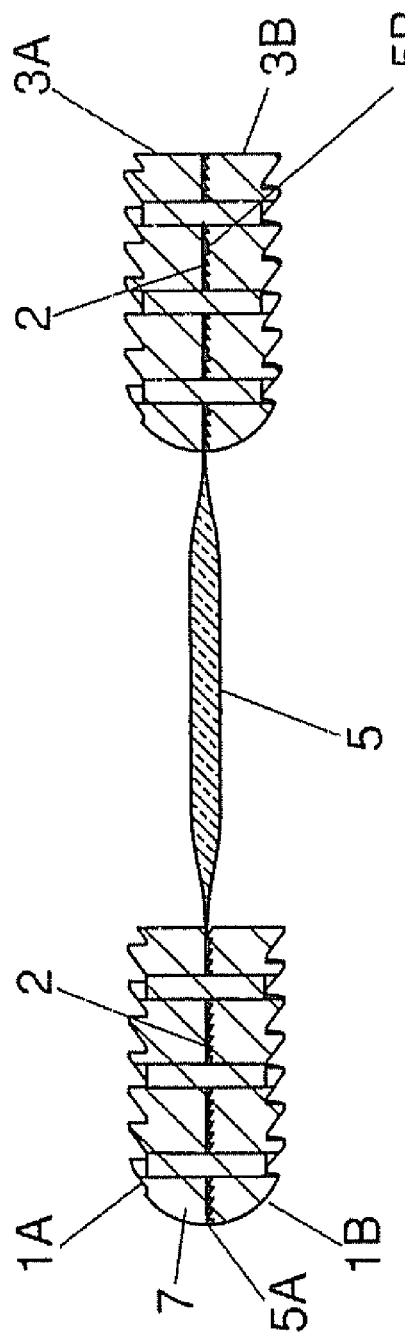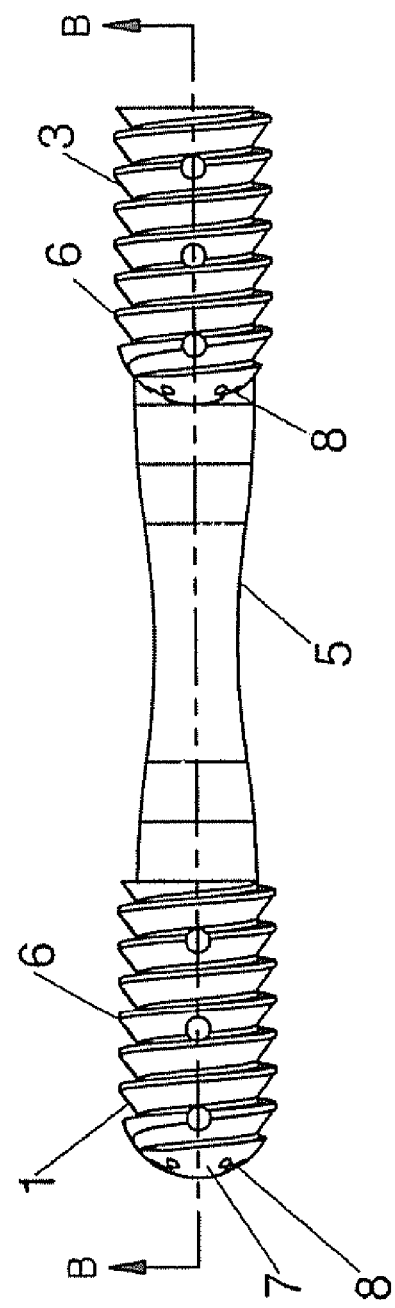

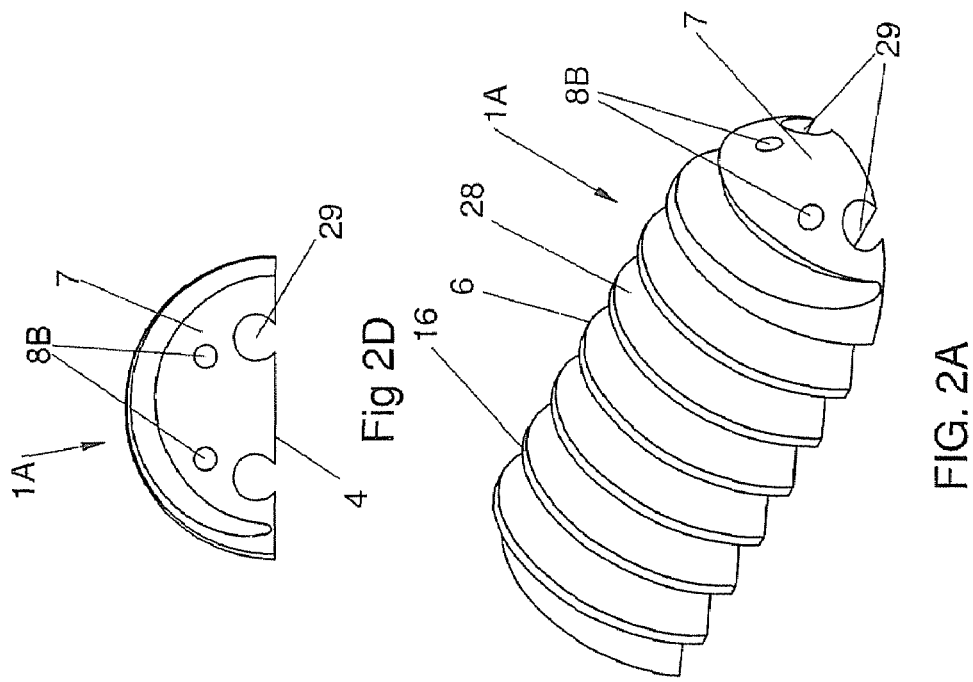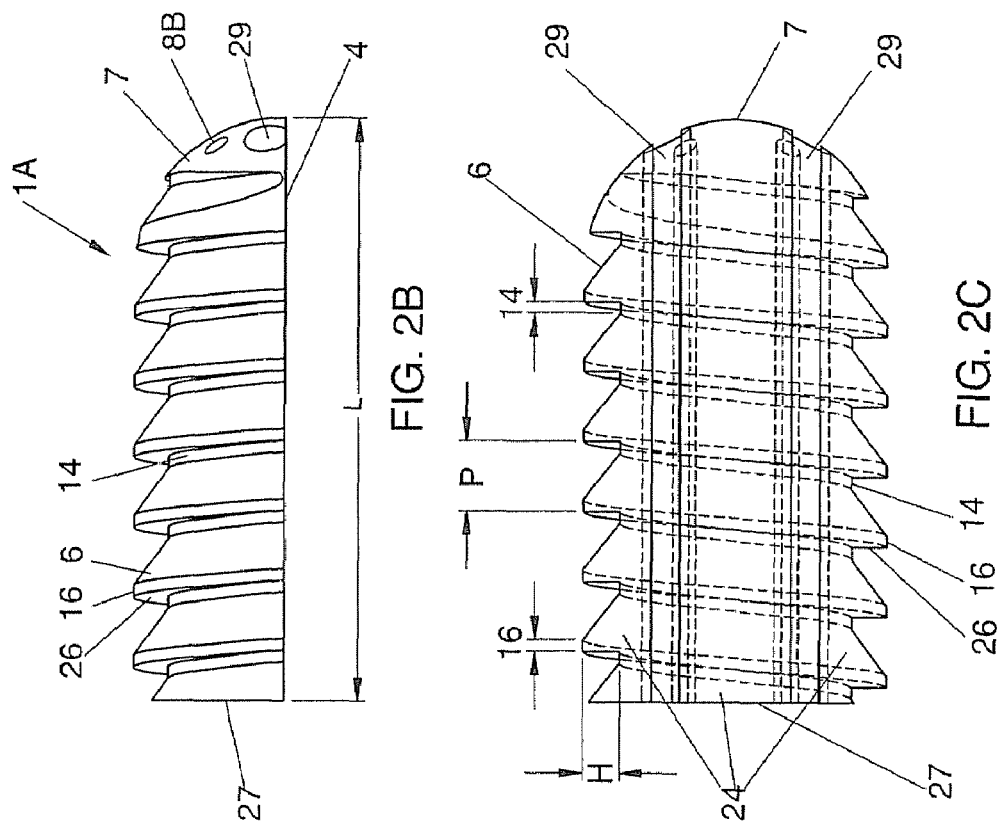

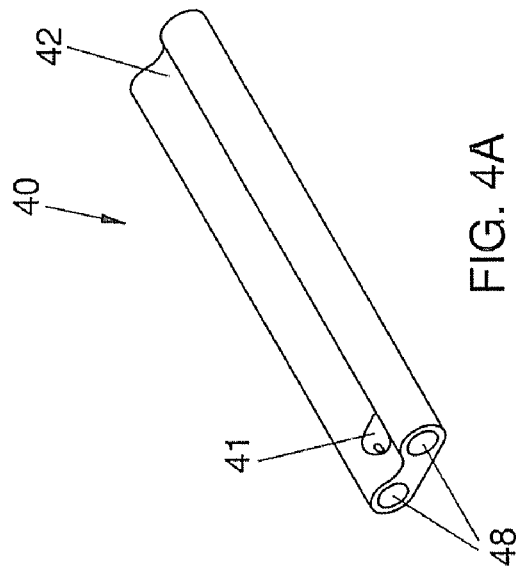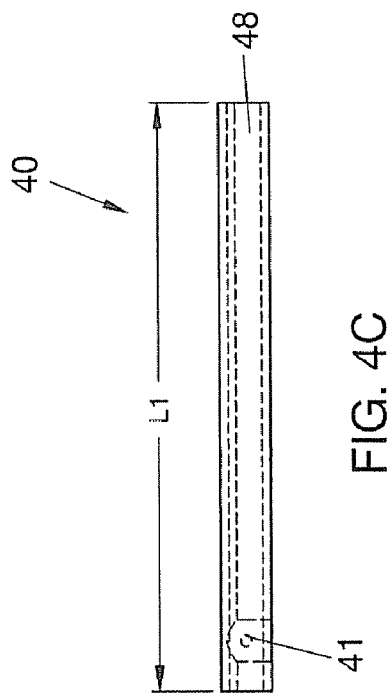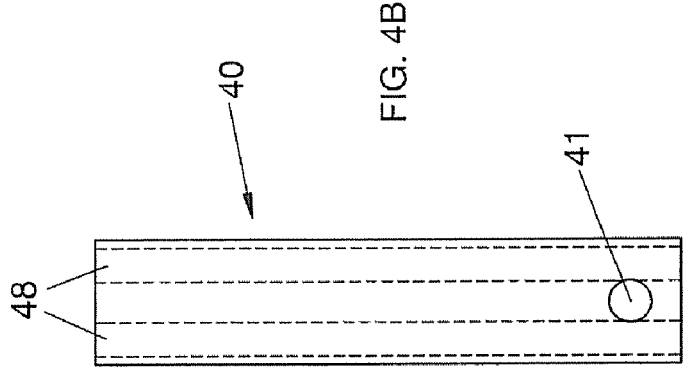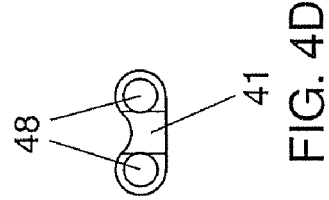

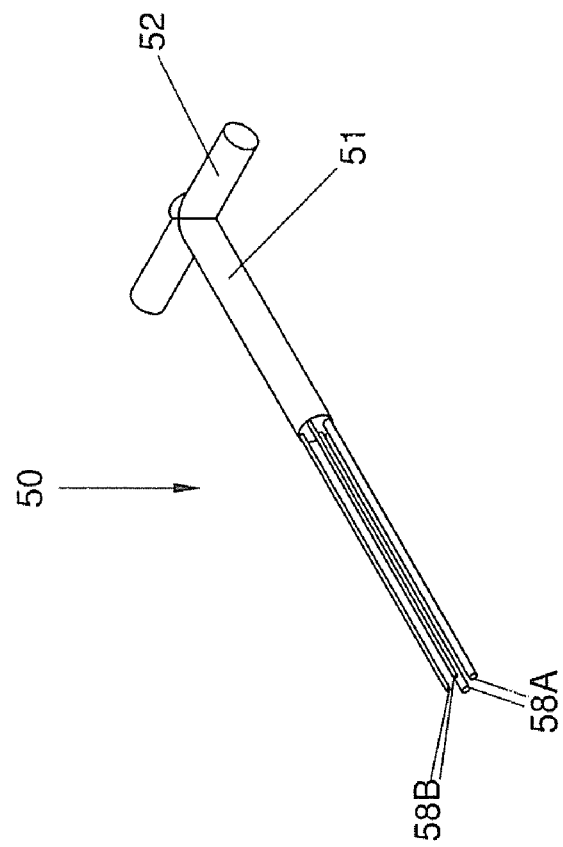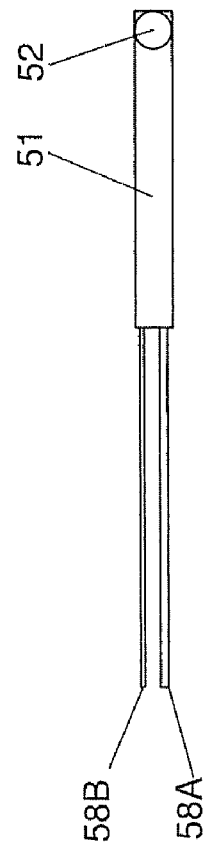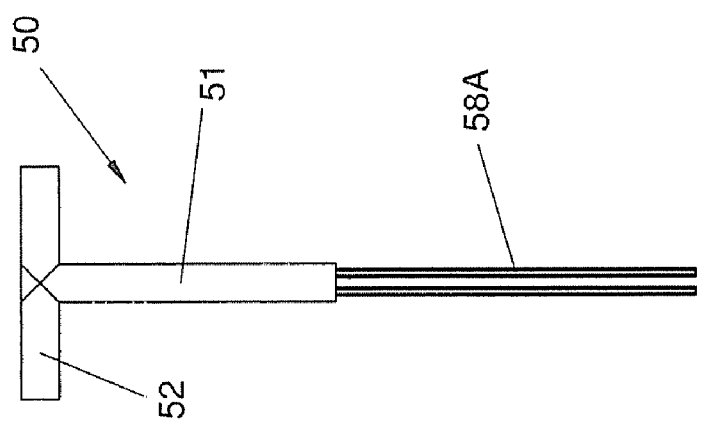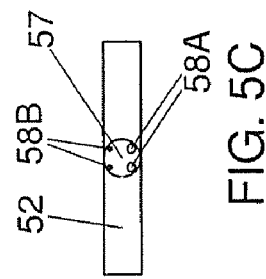
FIG. 5A
FIG. 5D
FIG. 5B
FIG. 5C

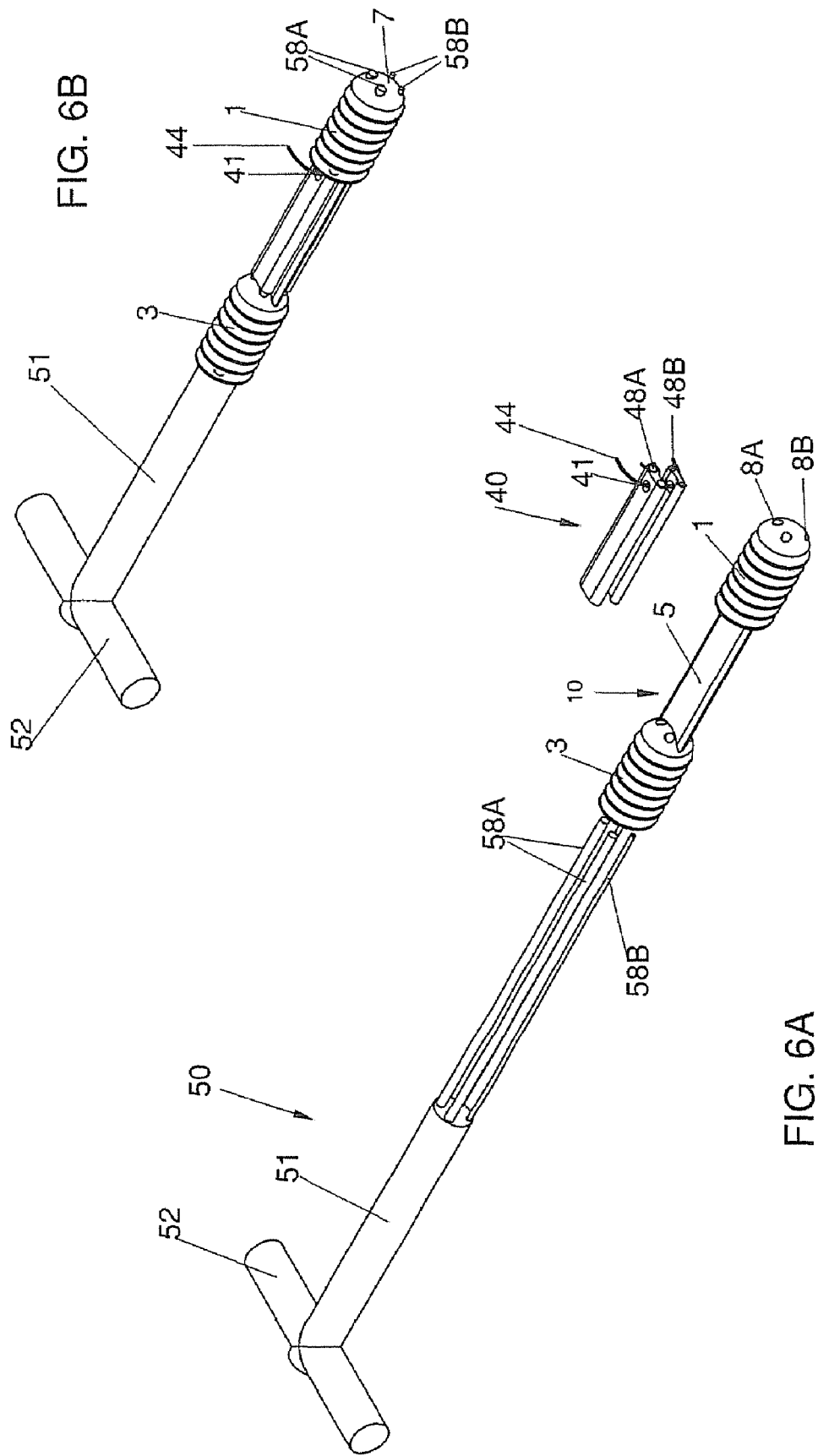

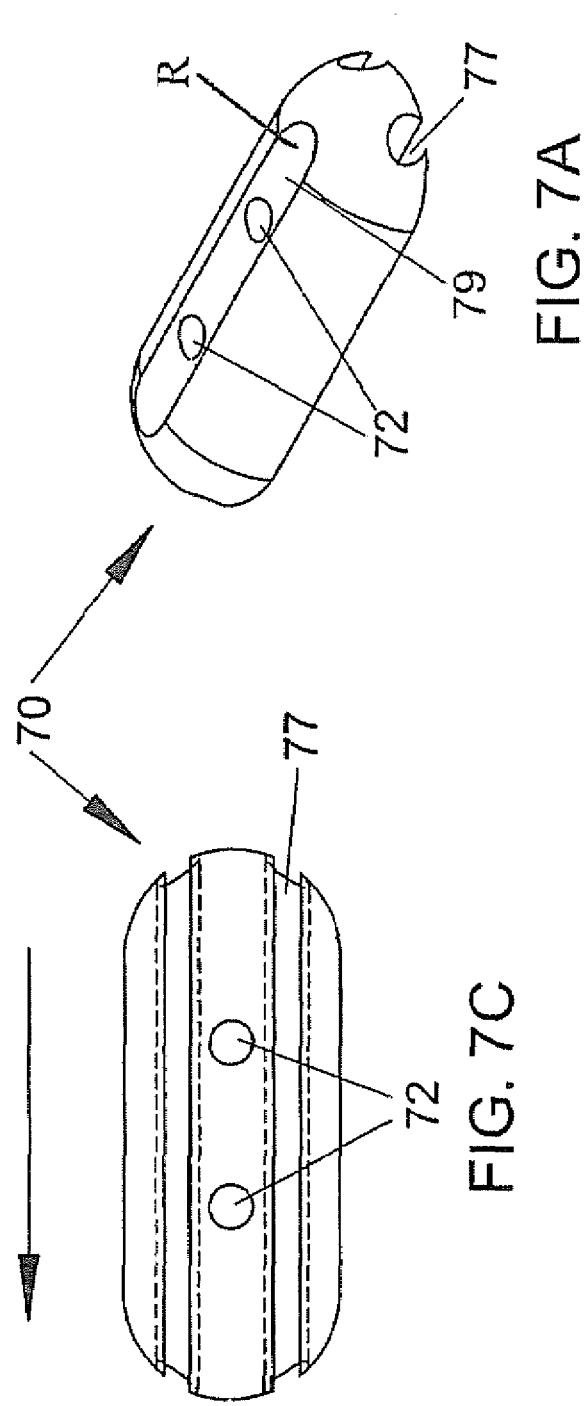
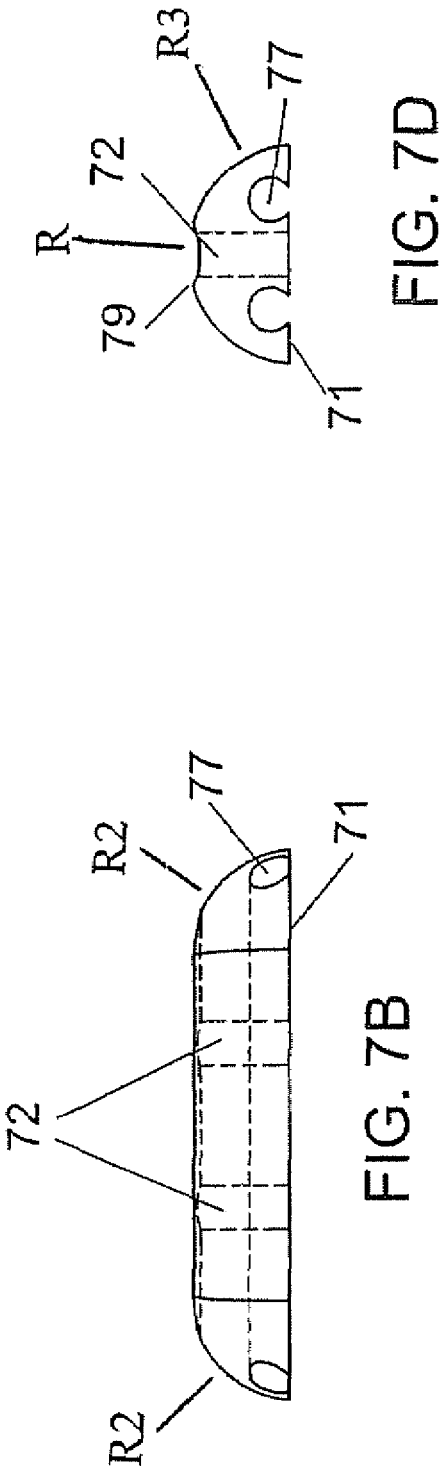

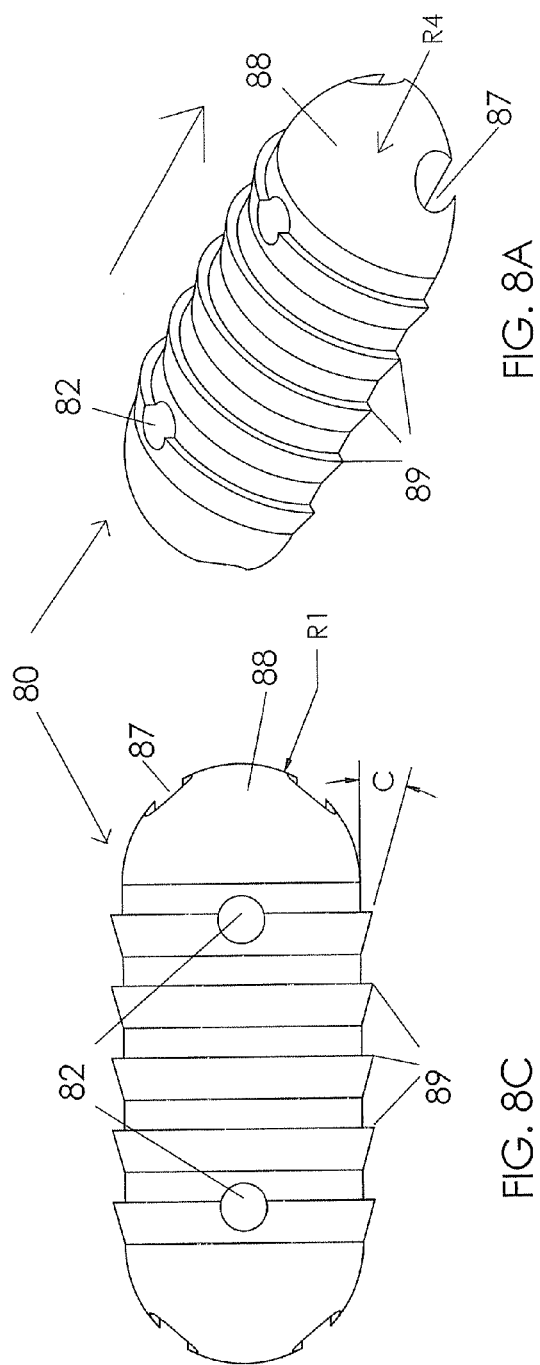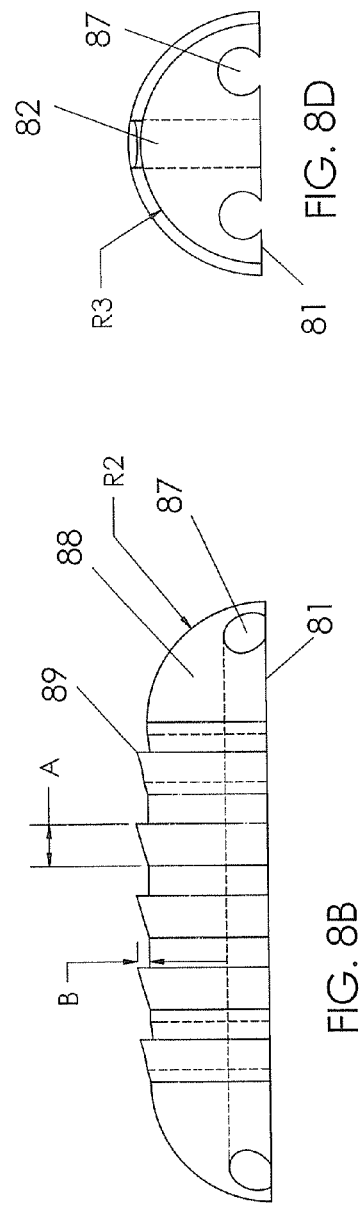

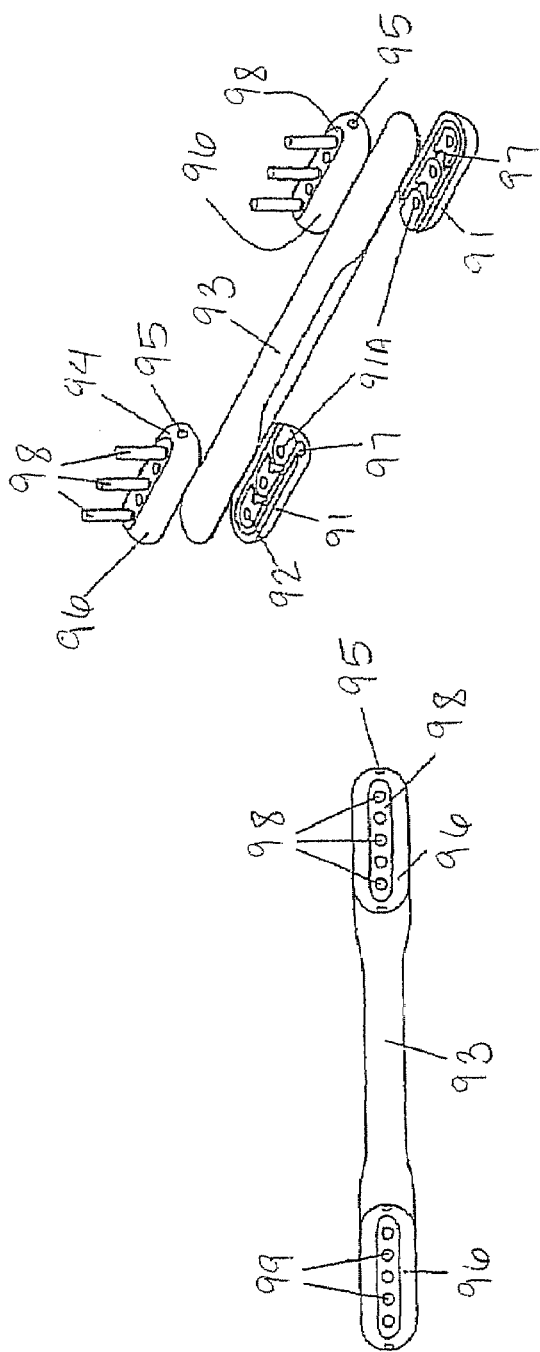
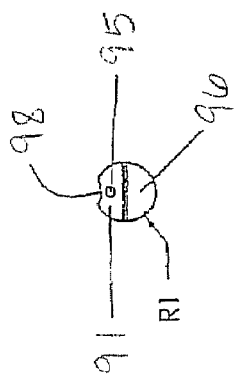
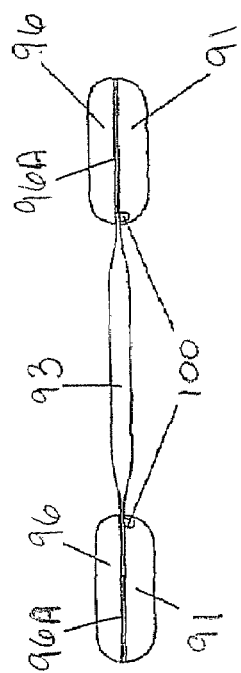
FIG. 9A
FIG. 9D
FIG. 9C
FIG. 9B

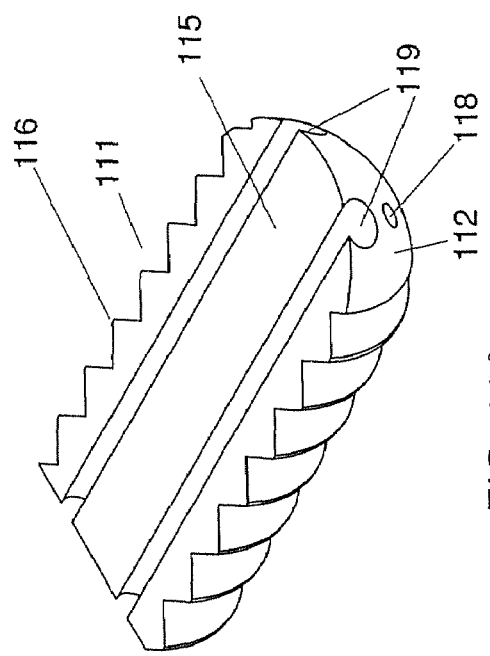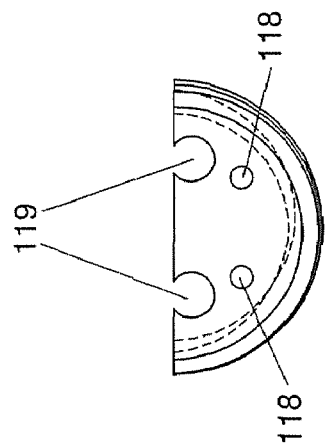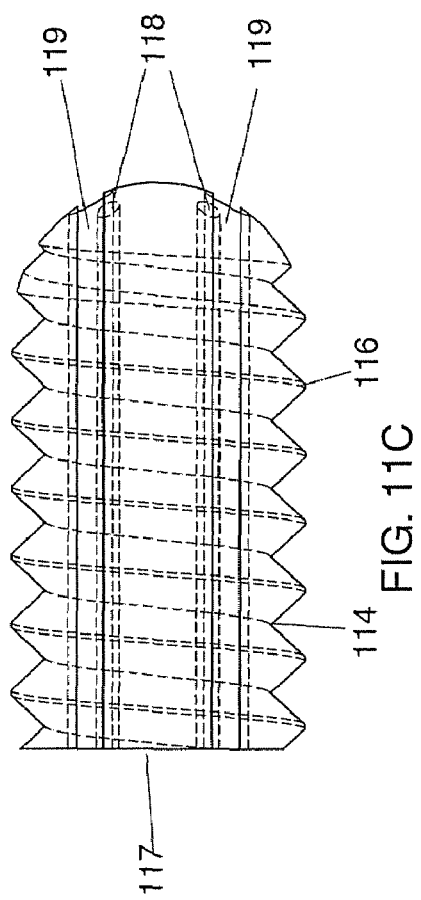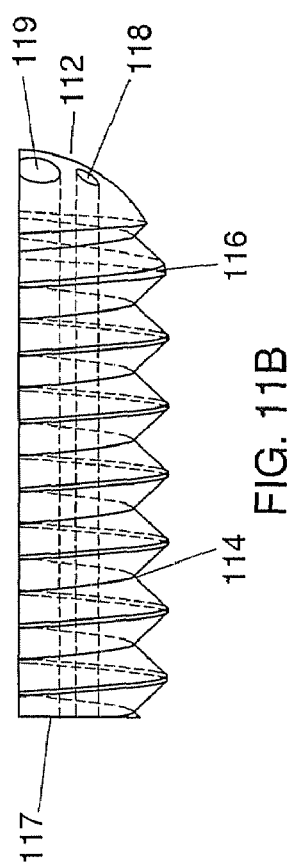

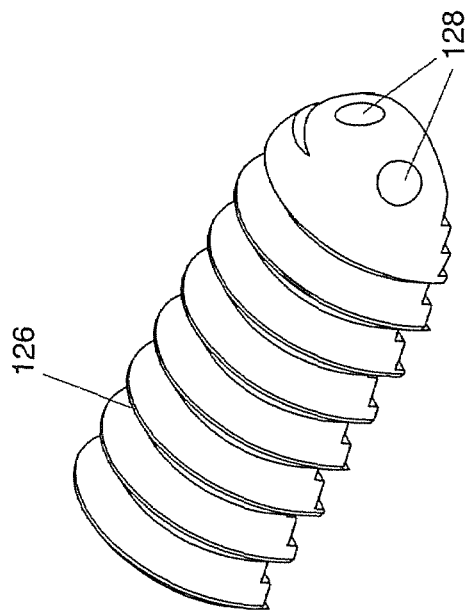
FIG. 12A
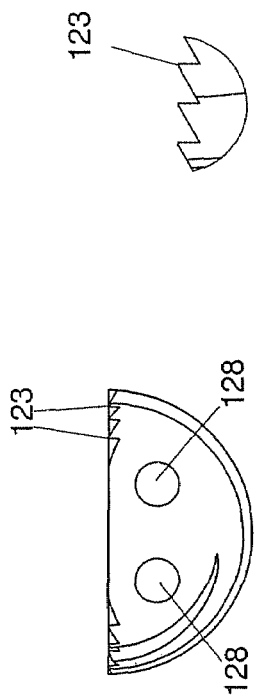
FIG. 12D
FIG. 12E
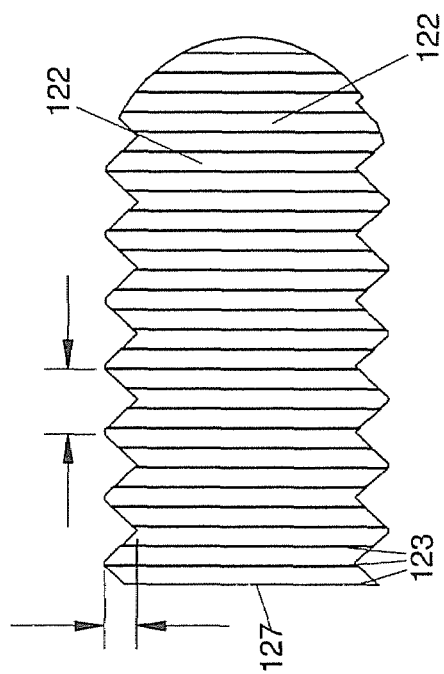
FIG. 12C
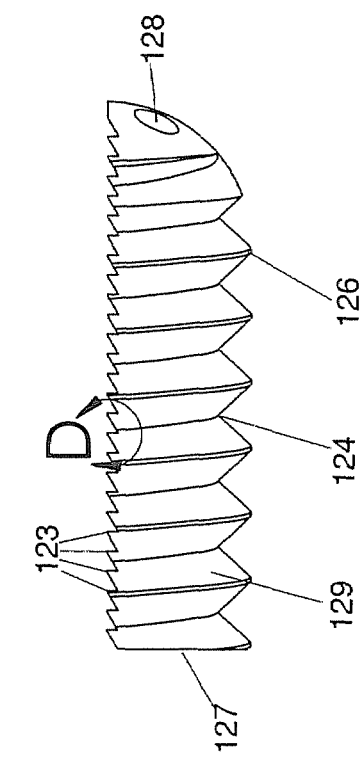
FIG. 12B

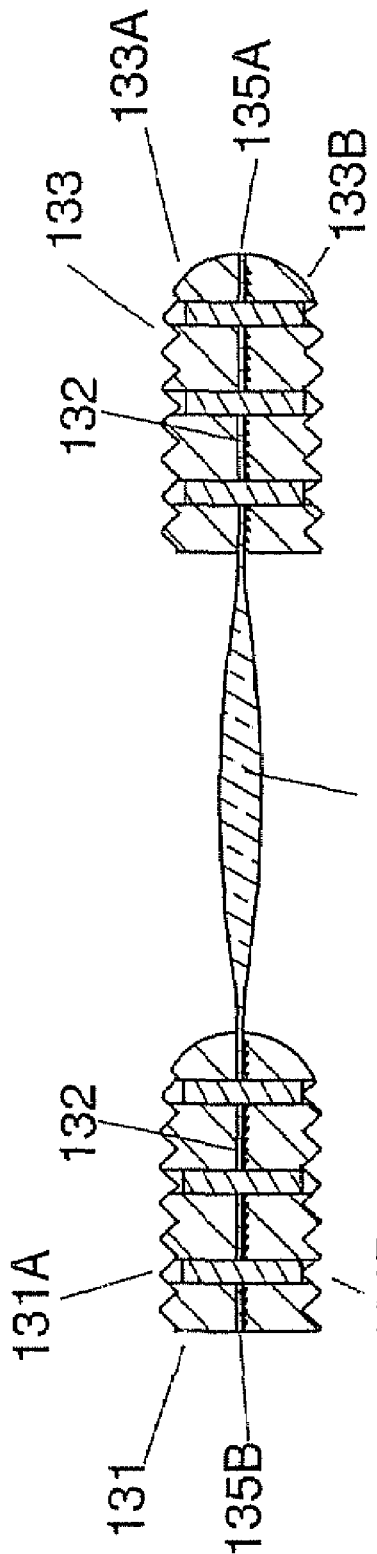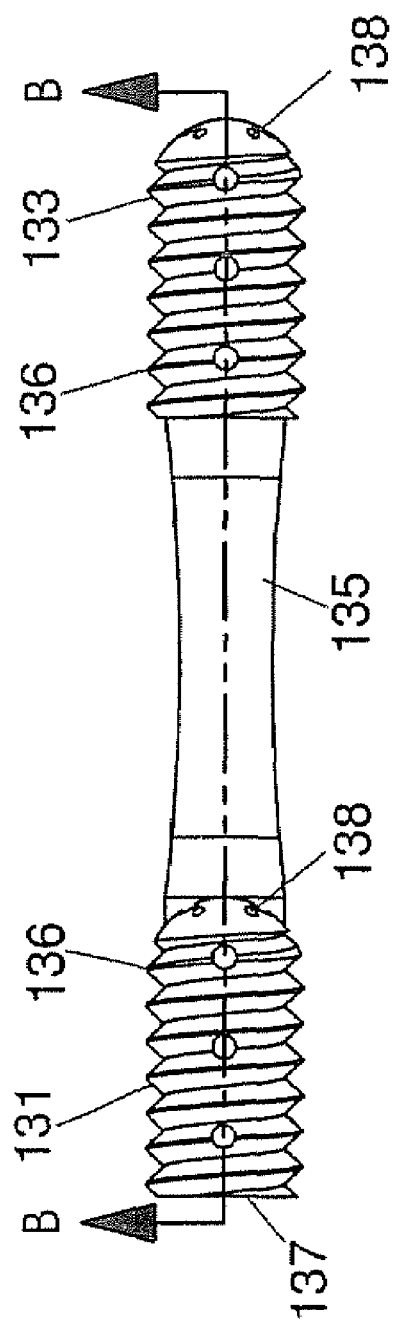
FIG. 13B
FIG. 13A

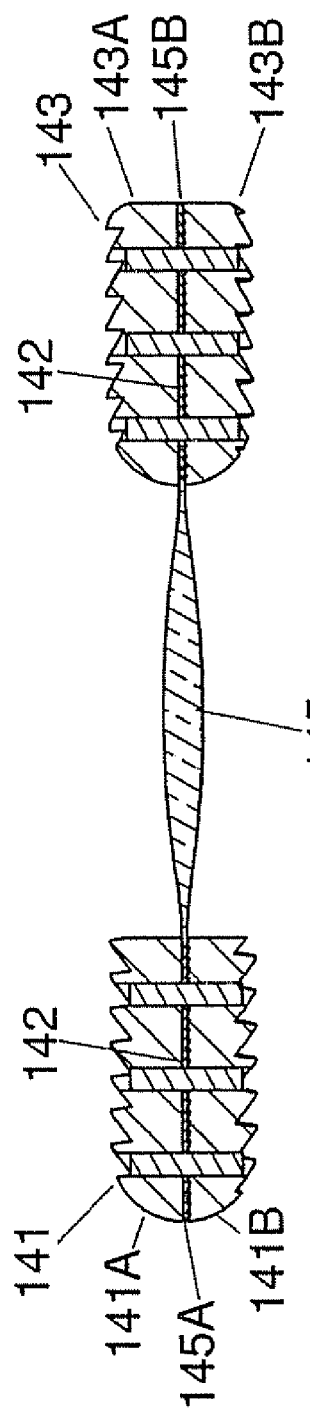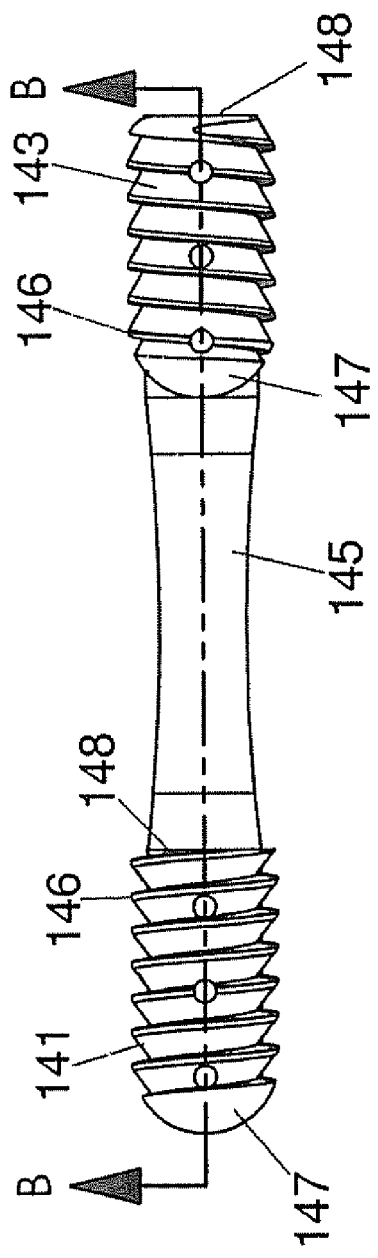

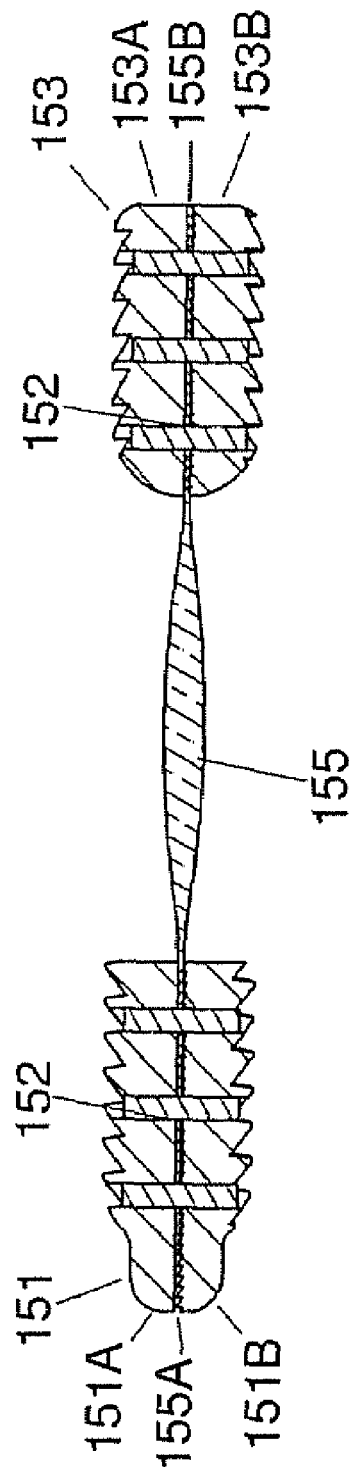
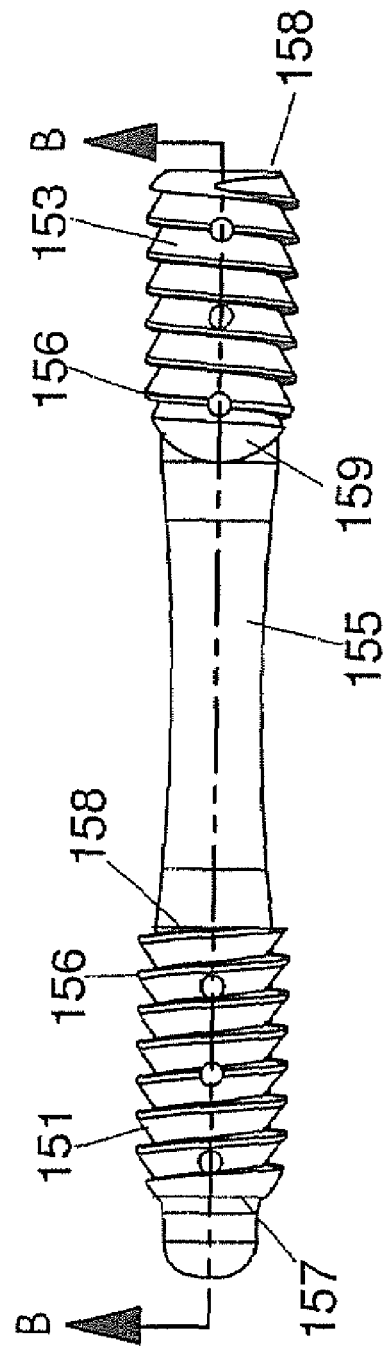

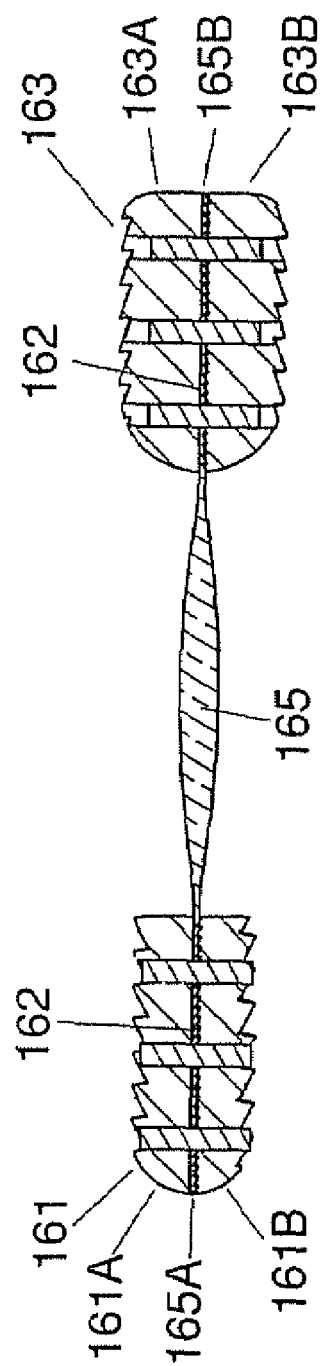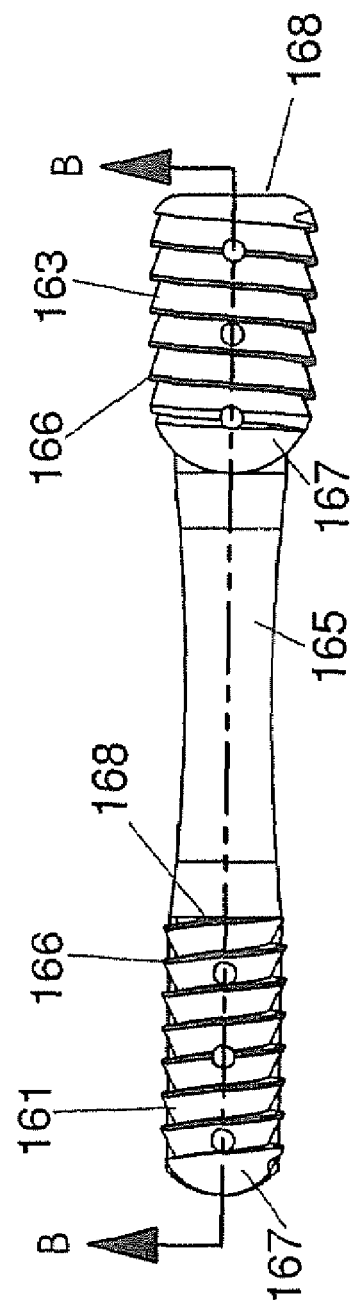

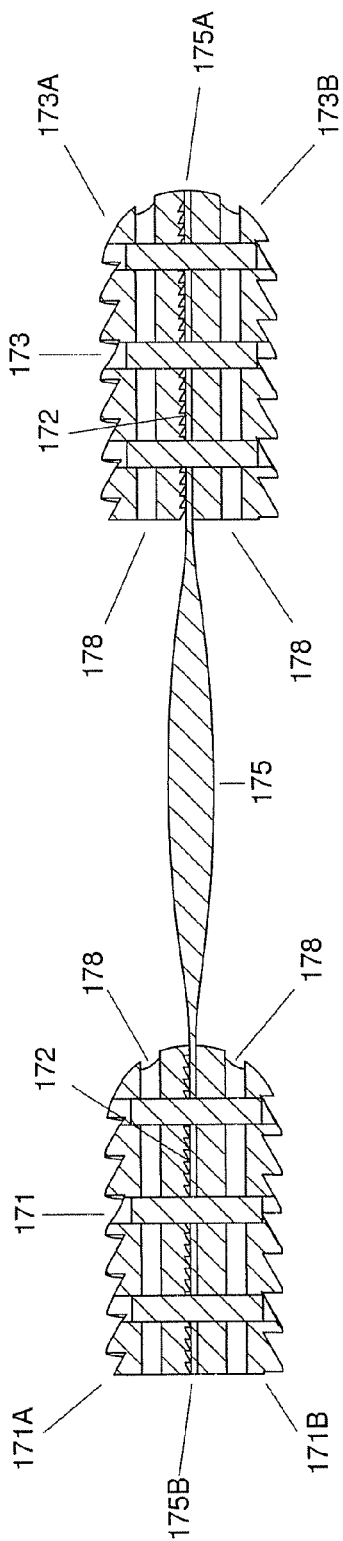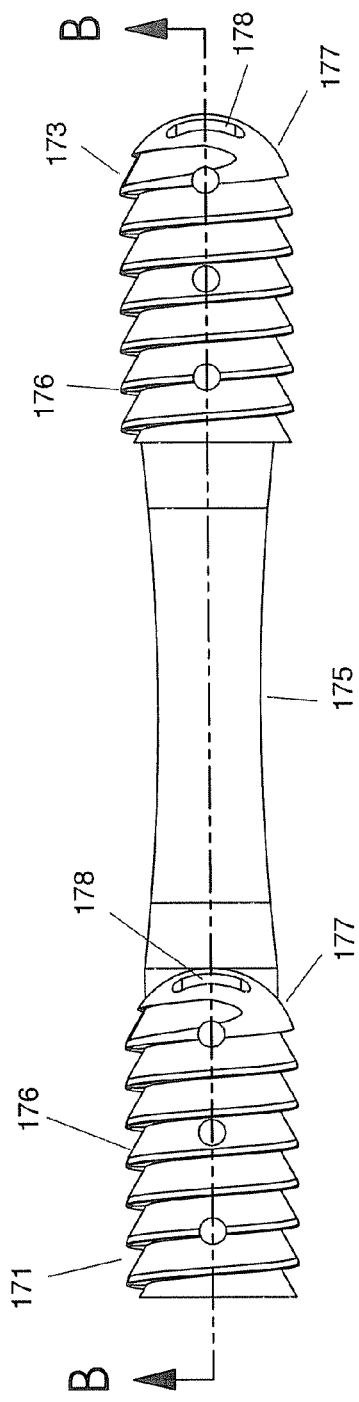
FIG. 17B
FIG. 17A

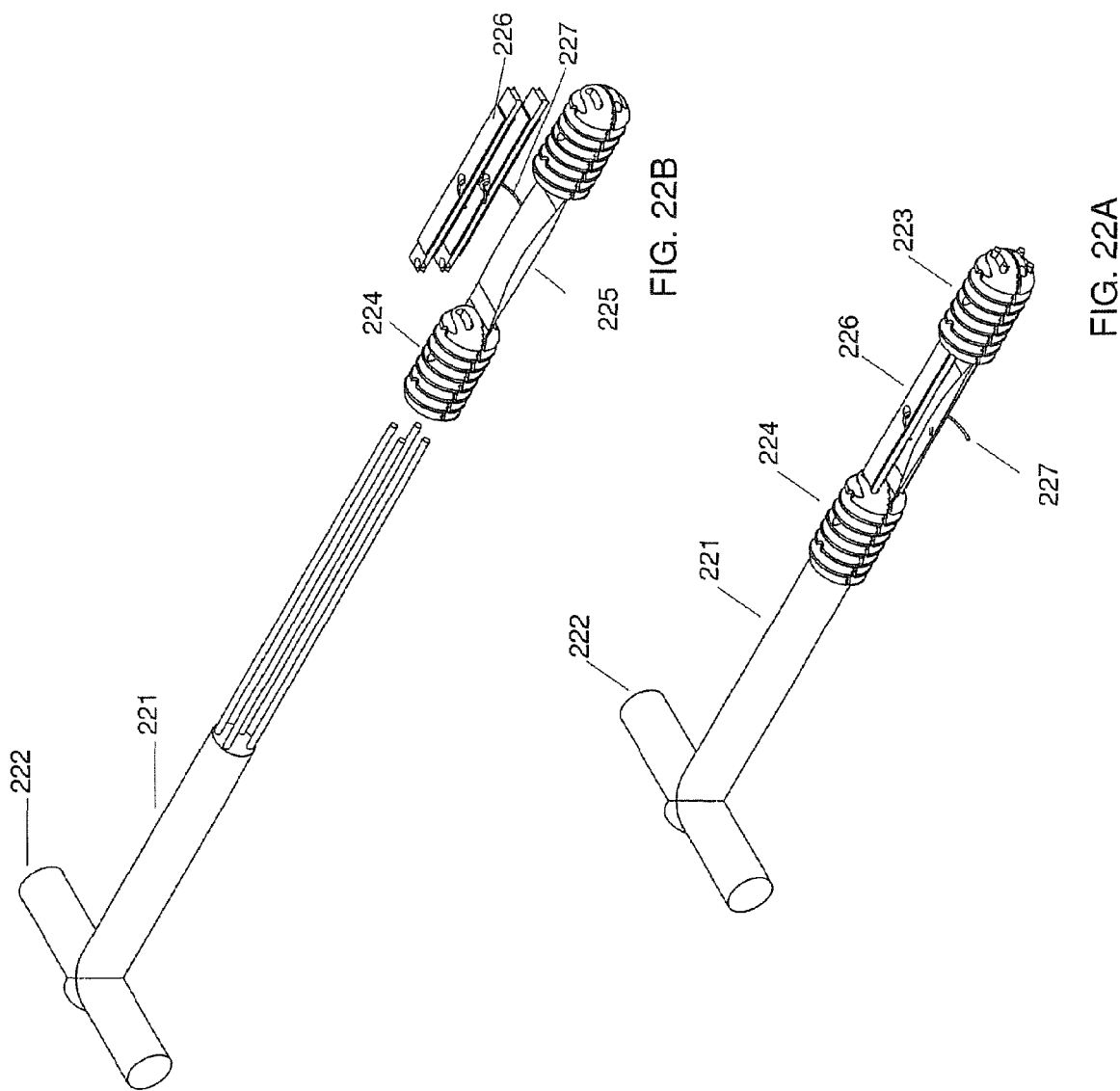

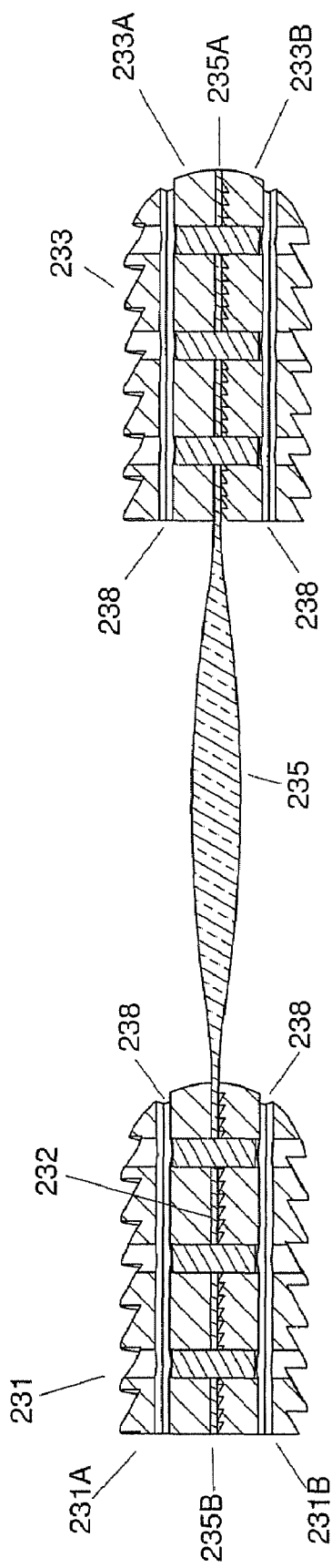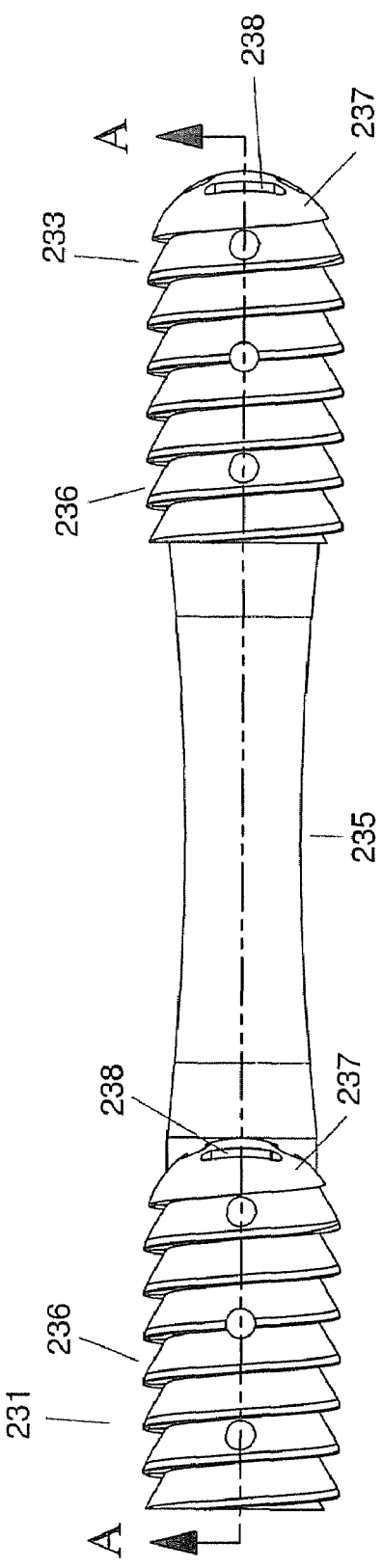
FIG. 23B
FIG. 23A

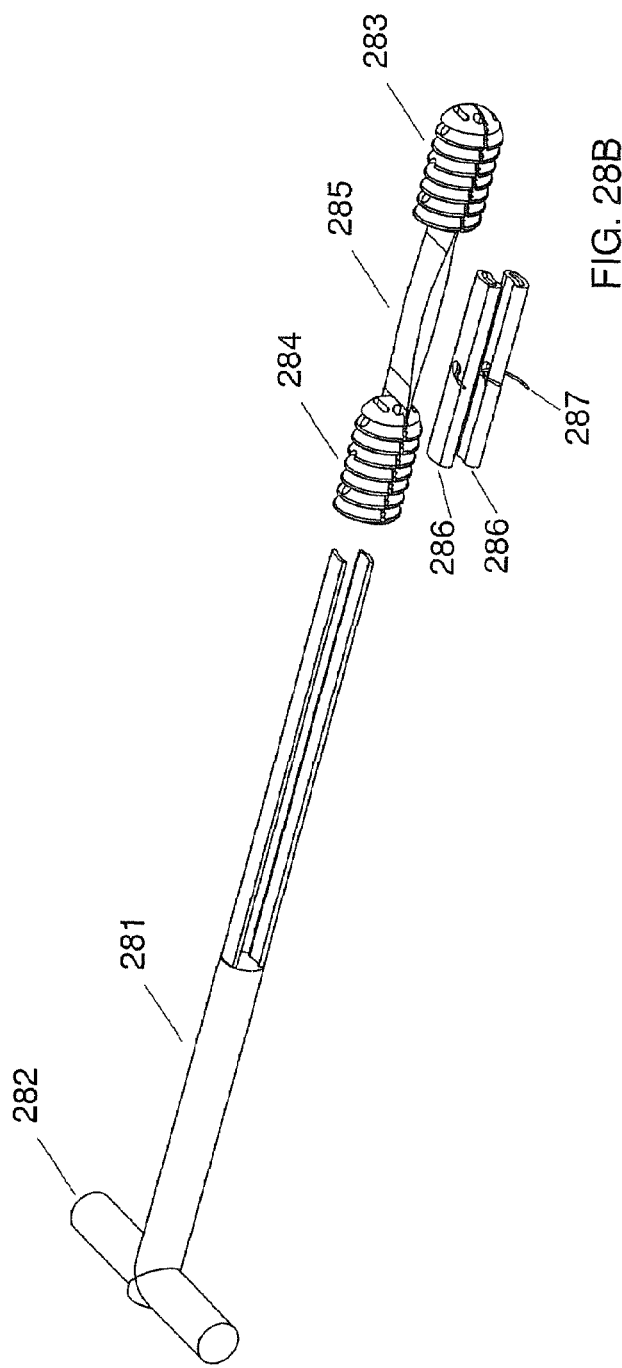
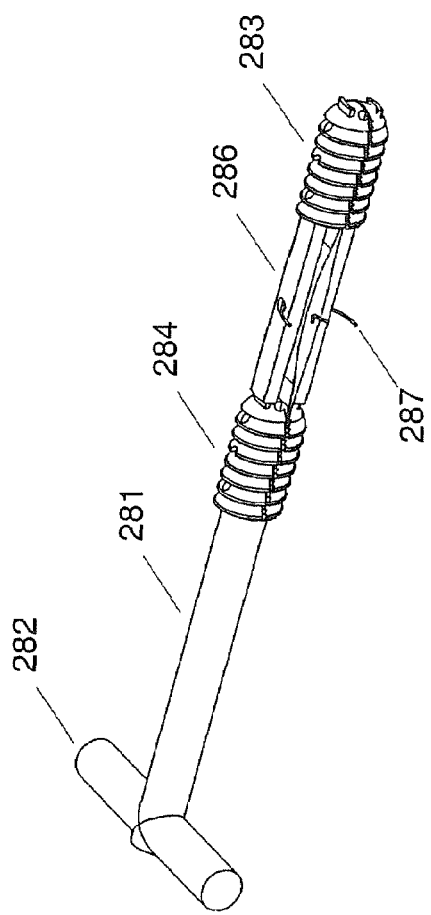
FIG. 28B
FIG. 28A

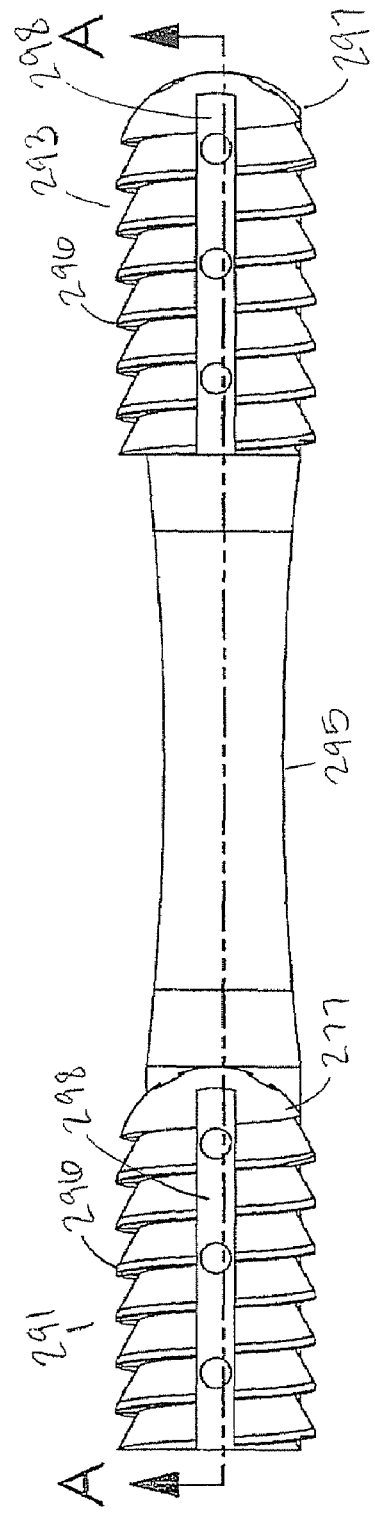
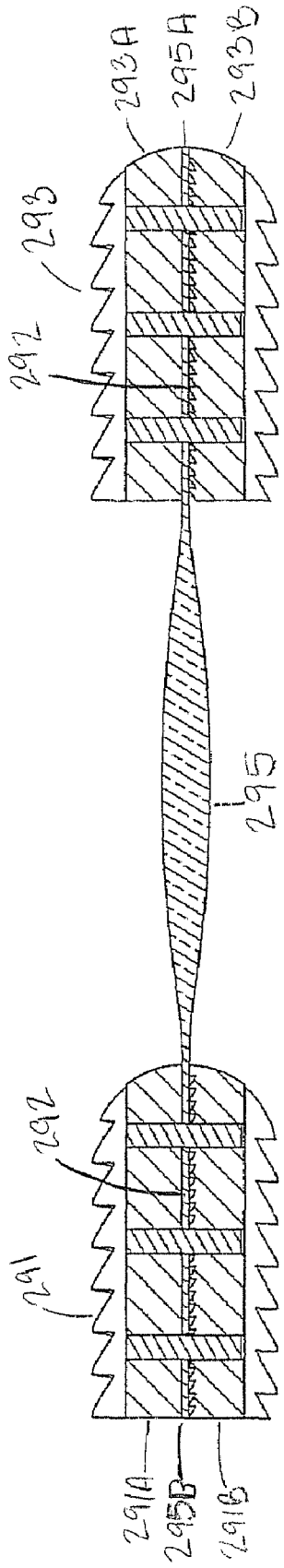
FIG. 29A
FIG. 29B

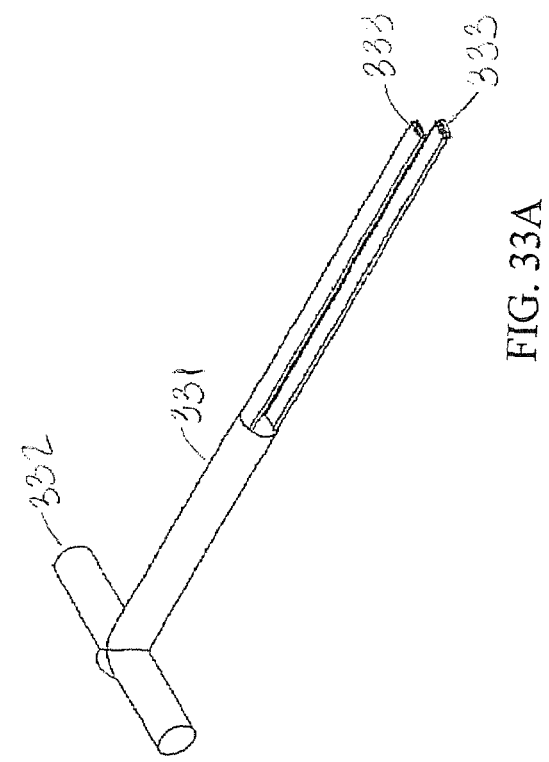
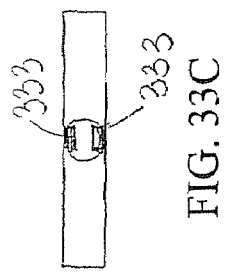
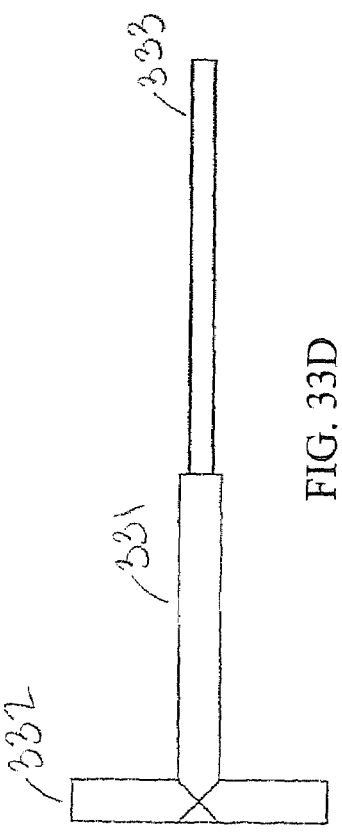
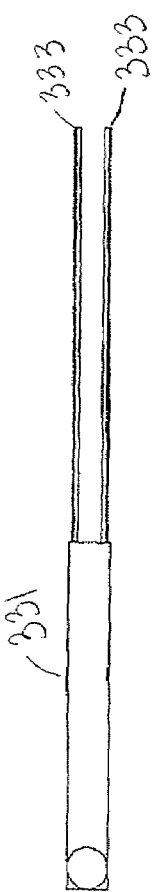
FIG. 33A
FIG. 33C
FIG. 33D
FIG. 33B

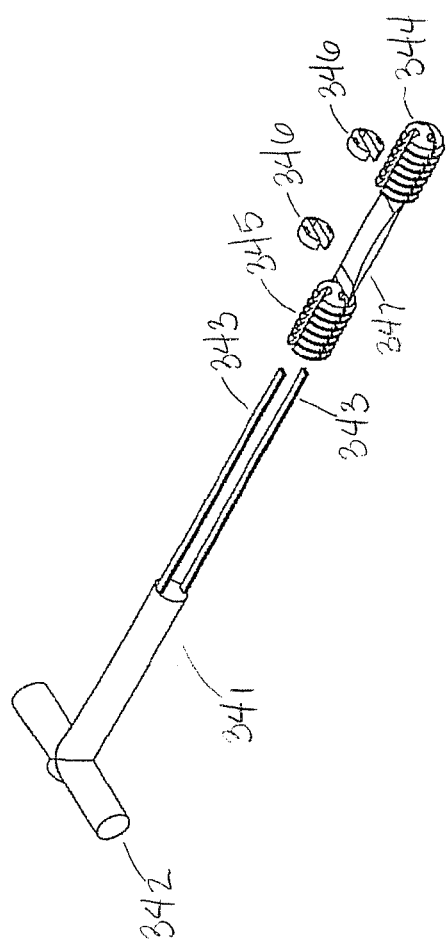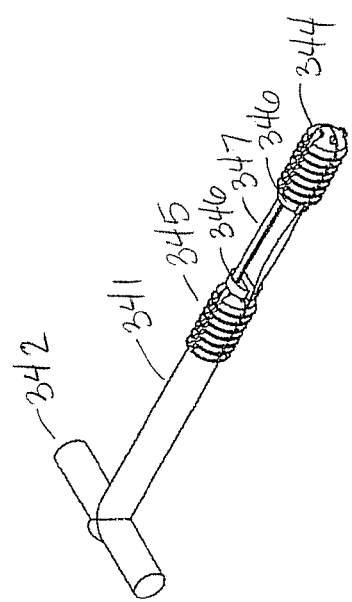
FIG. 34B
FIG. 34A

SELF FIXING ASSEMBLED BONE-TENDON-BONE GRAFT

This application is a continuation-in-part of commonly assigned U.S. Ser. No. 11/073,400, filed Mar. 4, 2005, now pending; and a CIP of U.S. Ser. No. 11/073,202, filed Mar. 4, 2005, now pending; and a CIP of U.S. Ser. No. 11/073,281, filed Mar. 4, 2005, now pending; and a CIP of U.S. Ser. No. 11/313,280, filed Dec. 19, 2005, now pending, all of which are incorporated herein by reference.

FIELD OF THE INVENTION

The present invention is related to the field of bone-tendon-bone implants, grafts and components thereof, for implantation in mammals, particularly for implantation in humans. In at least one aspect, the present invention is related to a self fixing bone-tendon-bone (BTB) graft comprising a length of tendon or ligament (collectively "tendon") having a first opposing end and a second opposing end, wherein a first bone block is attached to said first opposing end of said tendon and a second bone block is attached to said second opposing end of said tendon, and wherein at least one of said first bone block or said second bone block has an exterior surface having threads along at least a portion thereof. In one preferred embodiment, a self fixing assembled bone-tendon-bone (BTB) graft is provided wherein the two bone blocks on the opposing ends of the BTB have an exterior surface that is threaded in the same direction, so as to be capable of being inserted as a unit. In some embodiments, the tendon is preferably pre-tensioned by a removable tensioner that spans the gap between the bone blocks and applies tension to the tendon. Embodiments of self fixing assembled bone-tendon-bone grafts of the present invention are useful because they offer surgeons and patients various advantages such as simplified surgical technique, faster insertion and fixation, reduced operating room times, full internal tendon capture, bone to bone contact at the healing interface without the need for interference screws or secondary fixation, use of any suitable tendon specimen, construction to a predetermined gage length, and/or adherence to preferred surgical techniques, while maintaining a significantly increased tensile strength over BTB grafts formed by stitching, stapling or compression alone.

BACKGROUND OF THE INVENTION

In the field of medicine, there has been an increasing need to develop implant materials for correction of biological defects. Particularly in the field of orthopedic medicine, there has been the need to replace or correct bone, ligament and tendon defects or injuries. As a result, there have emerged a number of synthetic implant materials, including but not limited to metallic implant materials and devices, devices composed in whole or in part from polymeric substances, as well as allograft, autograft, and xenograft implants. It is generally recognized that for implant materials to be acceptable, they must be pathogen free, and must be biologically acceptable. Generally, it is preferable if the implant materials may be remodeled over time such that autogenous bone replaces the implant materials. This goal is best achieved by utilizing autograft bone from a first site for implantation into a second site. However, use of autograft materials is attended by the significant disadvantage that a second site of morbidity must be created to harvest autograft for implantation into a first diseased or injured site. As a result, allograft and xenograft implants have been given increasing attention in recent years. However, use of such materials has the disadvantage that human allograft materials are frequently low in availability and are high in cost of recovery, treatment and preparation for implantation. By contrast, xenograft implant materials, such as bovine bone, are readily available. However, immunological, regulatory and disease transmission considerations impose significant constraints on the ready use of such materials.

In view of the foregoing considerations, it remains the case that there has been a long felt need for increased supplies of biologically acceptable implant materials to replace or correct bone, ligament and tendon defects or injuries. This invention provides a significant advance in the art, and largely meets this need, by providing materials and methods for production of various bone-soft tissue implants from component parts to produce assembled implants.

Orthopedic medicine is increasingly becoming aware of the vast potential and advantages of using bone-tendon-bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting tendons to provide increased support to a damaged knee. These conventional techniques are not without their shortcomings; in most cases, the repaired joint lacks flexibility and stability.

The recent utilization of bone-tendon-bone grafts has dramatically improved the results of joint repair in cases of severe trauma. Even in cases of extensive damage to the joint ligaments, orthopedic surgeons have been able to achieve 100 percent range of motion and stability using donor bone-tendon-bone grafts. Despite these realized advantages, there have been some difficulties encountered with utilizing bone-tendon-bone grafts. For example, surgical procedures involving transplantation and fixation of these grafts can be tedious and lengthy. Currently, bone-tendon-bone grafts must be specifically shaped for the recipient during surgery, which can require thirty minutes to over an hour of time. Further, surgeons must establish a means of attaching the graft, which also takes up valuable surgery time. Accordingly, there is a need in the art for a system that addresses this and the foregoing concerns. Thus it is an object of this invention to provide a bone-tendon-bone graft that is constructed to precise dimensions and is adapted for robust fixation while allowing adherence to preferred surgical techniques and promoting reduced operating room times and providing fewer opportunities for error during surgery.

Bone-tendon-bone (BTB) grafts of the prior art are made in one of two ways: (1) by harvesting a naturally occurring tendon/ligament and portions of the bone(s) to which it is attached, thus maintaining the naturally occurring attachment of tendon/ligament and bone; or (2) by attaching the opposing ends of one or more pieces of tendon, ligament or a synthetic material to separate bone blocks. The name BTB is used for historical reasons. One skilled in the art recognizes that by definition, a "tendon" is a collagenous cord that attaches muscle to its point of origin, typically to bone. By definition, a "ligament" is a band of collagenous tissue that interconnects bone or supports viscera. Thus, it would appear that a BTB would more properly be called a bone-ligament-bone graft or implant. However, many of the earliest BTBs employed a tendon, which is larger and generally more plentiful in a body. The name bone-soft tissue graft thus more accurately encompasses the subject matter meant when the term bone-tendon-bone graft is used. Because the name BTB became adopted by the art, it is used herein to encompass all of the bone-soft tissue-bone and bone-soft tissue grafts described herein.

Additionally, the term "tendon" as used herein means a length of tendon, a bundle of tendons of the same or different lengths, a length of ligament, a bundle of ligaments of the same length or different lengths, a segment or segments of pericardium, dermis or fascia, or a combination thereof. Preferably, the tendon is a length of tendon or ligament, or a bundle of tendons or ligaments of the same length or different lengths, or a combination thereof. It is also within the scope of the present invention that the tendons or ligaments or both in the bundles are of the same thickness or of different thicknesses. In the bundles, the tendons, or ligaments or both can be allograft, xenograft, synthetic, artificial ligament scaffolds or a combination thereof. Preferably, the tendons are allograft or xenograft.

Tendons (or ligaments) are fibrous semi-hard materials that are slippery and difficult to grip. Thus, one of the issues in manufacturing an assembled BTB is how to attach the slippery tendon to the bone. The tendon has a tendency to squirm and slip when compressed between boney surfaces, much like a banana peel compressed between the floor and one's foot. One solution that is commonly used is to bite the tendon with a component that has some sort of teeth or threads, providing improved gripping over a flat surface. However, teeth or threads have a tendency to cut into the tendon fibers when the tendon is pulled at high tensile strength. Thus, most assembled BTBs provide some sort of trade-off between reducing slipping and squirming by biting which does not allow for achievement of maximum tensile strength.

U.S. Pat. No. 5,370,662 ("the '662 patent"), which issued to Stone on Dec. 6, 1994 and which is entitled "Suture Anchor Assembly," discloses the use of a screw made from titanium, stainless steel, or some other durable, non-degradable, biocompatible material having an eyelet at one end for attaching a suture connected to a soft material, such as a ligament or tendon. U.S. Pat. No. 5,370,662 at col. 1, lines 8-9. One problem with such a device is that the screw, although biocompatible, will never become assimilated into the patient's body. A second problem is that the tendon or ligament will never form a natural attachment to the screw.

One attempt at solving these problems was disclosed in U.S. Pat. No. 5,951,560 ("the '560 patent"), which issued on Sep. 14, 1999 to Simon et al. and which is entitled "Wedge Orthopedic Screw." The '560 patent discloses a wedge-shaped interference screw made from a biocompatible material for use with a ligament and with two bone blocks for performing anterior cruciate ligament repairs. In the '560 patent, a bio-compatible, wedge-shaped interference screw, a bone block and a ligament are inserted into an osseous tunnel drilled into a bone of a patient in need of a ligament repair. The interference screw compresses the flat surface of a bone block against a ligament that is pressed into the wall of the osseous tunnel. As the interference screw advances, the force that it presses against the ligament is buttressed by the force against the opposing tunnel wall. A second interference screw compresses a second bone block against an opposing end of the ligament in a second osseous tunnel drilled in a second bone in need of ligament repair. It is more difficult to pull a predetermined tension on the tendon because the tendon slips in the bone tunnel and uncontrollably alters the tension when the interference screw is being threaded in the bone tunnel. The slippery ligament is also subject to slippage when compressed between the bone block and the tunnel wall. Such slippage results in a loss of tension in the joint. In the case of an anterior cruciate ligament (ACL) repair, this loss of tension causes a wobbly knee. This is undesirable in any human, and particularly in athletes. It is an object of the present invention to provide a bone to tendon connection that will decrease slippage and loss of tension in a BTB. Therefore, it is an object of the present invention to provide a BTB with a stiffness of at least 90 N/mm, preferably 170 N/mm, more preferably 230 N/mm. It is also an object of the present invention to provide a BTB with an elongation of no more than 5 mm, preferably less than 2 mm, more preferably less than 1 mm. Stiffness and elongation for any given BTB can be calculated by methods known in the art. Stiffness is defined as the slope of the force-displacement curve when the BTB is subject to axial load increasing from below 100 Newtons to above at least 200 Newtons. Elongation is defined as the difference in length for a given BTB measured before the first cycle of a dynamic load test and after 1000 cycles of loading to at least 200 Newtons.

Another approach to making a BTB is disclosed in U.S. Pat. No. 5,961,520 ("the '520 patent") which issued to Beck, et al. on Oct. 5, 1999, and which is entitled "Endosteal Anchoring Device for Urging a Ligament Against a Bone." Like the '560 patent, the '520 patent utilizes an interference screw and a bone block (called an "anchor body" therein) to press the end of a ligament against the side wall of an osseous tunnel in the patient's bone. The '520 patent differs from the '560 patent in that the ligament loops around the bone block in a "U" shape. This "U" shape of the tendon captures the tendon in the first bone tunnel, but leaves two free tendon ends to be secured in the second bone tunnel. In addition in the '520 patent, the bone block, which presses the ligament against the walls of the osseous tunnel contains two grooves for "locking" (col. 7, line 2) the ligament in place, and "restricting excessive compression on the ligament" (col. 7, lines 8-9). The "locking" of the tendon against the tunnel wall still leaves the tendon free to move against the tunnel wall near the ends of the anchor body. This leads to impaired healing and recovery due to tendon to bone contact within the tunnel and also due to micromotions of the tendon within the tunnel. Ultimately, this may lead to widening of the bone tunnels rather than their closure. Additionally, the location of the tendon in the locking grooves is a function of the anchor body design and is not a controlled design parameter. Thus, the tendon placement with respect to either the tunnel wall or the tunnel centerline cannot be matched to particular surgical needs or to surgeon preference.

Yet another approach to making a BTB is disclosed in commonly assigned U.S. Pat Appl. Pub. No. 2003/0023304 ("the '304 publication"), to Carter et al., which published on Jan. 30, 2003. The '304 publication discloses several embodiments of a BTB. In each of the various embodiments, a tendon is bound in an internal chamber created in the bone blocks. For example, in FIG. 10, a plurality of cams reverse the direction of the tendon several times and cancellous chips packed in any open space bite into the tendon to keep it from slipping. In FIG. 12, a screw compresses the tendon against the side of an internal chamber. In FIG. 14, an internal wedge that has teeth bites into a tendon and tightens the grip as the tendon is pulled. In yet another embodiment, shown in FIG. 15, one end of a tendon is doubled over and the doubled over end is held in place by a series of grooves and rings. While all of these embodiments are useful, they each are challenging to manufacture and/or assemble due to their inherent complexity and reliance on small or intricate parts. It is an object of the present invention to provide a BTB having a robust design, simple components, ease of manufacturability, and high reliability, all while maintaining an acceptable tensile strength, stiffness, and elongation performance. This is important for all BTB grafts, especially for those implanted in athletes and other individuals where maximum performance is required.

One isolated and purified BTB that is not hindered by slippage or cut fibers when subjected to high tensile pulling is disclosed in commonly assigned U.S. Pat. No. 6,497,726 ("the '726 patent") which issued on Dec. 24, 2002 to Carter et al. The '726 patent discloses the use of natural BTBs that are cut from allograft or xenograft sources, commonly referred to as "pre-shaped BTBs." Typically, the BTB is cut as a single piece from a section of the patella (bone), patellar tendon and the tibia (bone) of the donor. One problem is that only 2-3 grafts can be obtained per knee of the donor, depending upon the donor's age and health. Hence, it is an object of the present invention to be able to make BTB grafts in large quantities. It is also an object of the present invention to make BTB grafts having high tensile strength, suitable for ACL repairs, from tendon and bone components, wherein the BTBs are constructed so as to minimize the art recognized slippage and tearing associated with conventional modes of construction as described above.

Another problem with pre-shaped (natural) BTBs is that the size of the BTB or the length of the tendon between the two bone pieces cannot be precisely selected. Some of the physical dimensions of the graft, particularly tendon (ligament) length, are determined by the anatomy of the donor. Frequently, this leads to compromises such as excessive gage length, or length between the bone blocks, which result in surgical challenges and compromised healing and recovery. For example, a natural BTB with a tendon that is too long for an ACL repair results in having a length of unsecured and wobbling tendon in the bone tunnel between the ends of the secured bone portions. The wobbling tendon hinders healing in the bone tunnel. Hence, it is yet another object of the present invention to be able to make BTB grafts having a predetermined and variable set of design parameters including gage length, bone block diameter, tendon size, and bone block or tendon shape, size, orientation or a combination thereof.

The standard method for implanting a BTB is to use an interference screw to fix each of the bone blocks in a bone tunnel. Typically, the bone block has a groove or a notch along all or a portion of its length to accommodate the shape of the screw. In some instances the groove in the bone block is even threaded. A problem with this mode of attachment is that in the bone tunnel, the forces are not equal on all sides of the bone bock. Rather, the side of the bone block that is in contact with the interference screw and the opposing side of the bone block that is in contact with the bone tunnel would experience the greatest force and some compression which often leads to fracturing. As a result, healing around the bone block would be uneven until all of the bone block was eventually remodeled. It is an object of the present invention to provide a BTB that can be installed and fixed within an osseous tunnel without an interference screw so as to eliminate variable compression between the bone blocks of the BTB and the bone tunnel. It is a further object of the present invention to provide a BTB wherein the tendon is optionally pretensioned.

BRIEF SUMMARY OF THE INVENTION

The present invention has multiple aspects. In a first aspect, the present invention relates to self fixing bone-tendon-bone (BTB) grafts that are useful in a mammalian patient in need of tendon replacement, repair or augmentation. In one embodiment, the self fixing bone-tendon-bone (BTB) graft comprises a length of tendon or ligament (collectively "tendon") having two opposing ends, a first opposing end and a second opposing end, wherein a first bone block is attached to the first opposing end of the tendon and a second bone block is attached to the second opposing end of the tendon.

More specifically, one embodiment of a self fixing bone-tendon-bone (BTB) graft of the present invention comprises a length of tendon or ligament (collectively "tendon") having two opposing ends, a first opposing end and a second opposing end, wherein a first bone block is attached to said first opposing end of said tendon and a second bone block is attached to said second opposing end of said tendon, and wherein at least one of said first bone block or said second bone block has an exterior surface having threads along at least a portion thereof. In one aspect of such an embodiment, each of said first bone block and said second bone block has an exterior surface having threads along at least a portion thereof, and the threads of said first bone block and said second bone block run in the same direction so that each bone block is implantable in a respective hole in opposing bones of a joint on a patient when the BTB is rotated as a whole in the threaded direction.

To facilitate rotating the BTB graft as a whole, in at least one aspect of the present invention the first and second bone blocks have a plurality of holes in alignment for placement on an insertion tool, which is then used to implant the BTB graft in opposing bones on opposite side of a joint in a body in need of ligament repair, replacement or augmentation. Typically from 2 to 6 holes in the first and second bone blocks are in alignment, more preferably 4 holes are in alignment. In one embodiment, four aligned holes on the bone blocks receive four pins or prongs of the insertion tool (see e.g., FIGS. 5A-5D) which is then used to simultaneously thread both bone blocks in respective holes in their corresponding bones.

A typical use for BTB implants and grafts of the present invention is for ACL repair in a human patient where the insertion tool is used to thread the first (leading) bone block up through a bone tunnel (preferably threaded) in the tibia and into a hole (preferably threaded) in the femur. In an embodiment where both the leading and trailing bone blocks have threaded exterior surfaces, while the first (leading) bone block is being threaded into a hole in the femur, the second (trailing) bone block is being simultaneously threaded into the bone tunnel (preferably threaded) of the tibia by the same turning motion of the insertion tool. The insertion tool is rotated until the first (leading) bone block is properly positioned in the femur. Thereafter, the tension on the tendon can be adjusted by pulling the insertion tool out of the first (leading) bone block turning the second (trailing) bone block ¼ turn to ½ turn as needed to increase or decrease the tension.

Other possible uses for the implants, grafts, tensioners, or inserters of the present invention include shoulder repairs such rotator cuff repair, elbow repairs such as "Tommy John" surgery, ankle repair such as Achilles' tendon reconstruction or replacement, and repair or replacement of the many small tendons found in the hand or foot. There is also the potential for application in the spine, for dynamic stabilization or for replacement of supporting tissues such as the anterior longitudinal ligament.

It is also within the scope of the present invention that the threads on the first (leading) bone block have a smaller outer diameter (as measured to the outside of the threads) than the outer diameter of the threads on the trailing bone block. In such embodiments, the bone block itself (as measured by the inner diameter, not including the height of the threads) could have a smaller diameter, or the threads could have a shorter height (thus resulting in a smaller outer diameter of the overall bone block). Preferably, the outer diameter of the leading bone block is only slightly smaller than the outer diameter of the trailing bone block. In one such embodiment, the leading bone block would not resistively engage threads of the tibial bone tunnel and would readily pass therethrough to engage the properly sized threads in a tapped hole in the femur of the patient. Thus, while the leading bone block was engaging the femur, the trailing bone block would be engaging the threads in correspondingly sized and tapped bone tunnel of the tibia.

BTBs of the present invention are useful in mammals, including domesticated animals, such as dogs, cats, horses, cows, cattle, pigs, sheep and goats. However, the mammalian patient is typically a human. While self fixing BTBs of the present invention are useful in tendon replacement, repair or augmentation in any joint held together by tendons, they are most useful in the tendon replacement, repair or augmentation of the knee joint, particularly the human knee joint. In a typical knee joint, several tendons hold the tibia in juxtaposition against the femur. The locations of these several tendons are well known in the art and their repair or replacement is the subject of other BTB grafts. The self fixing BTBs of the present invention are useful in repairing, replacing or augmenting any one or more of those well known tendons. Preferred tendons that are repaired, replaced or augmented with a self fixing BTB graft of the present invention include the anterior cruciate ligament (ACL), the posterior cruciate ligament (PCL) and the medial collateral ligament (MCL)), and any other tendons of the knee or other joints (e.g., the fingers, wrist, ankle, hip, or shoulder).

Assembled self fixing BTBs of the present invention may have a bone block on only one end of the tendon, or on each end thereof. When the BTB has only one bone block on one end of the tendon, it can be referred to as a bone-tendon, or BT graft.

Bone blocks suitable for use with the present invention can comprise one or more bone segments. In preferred embodiments, a bone block comprises a first bone segment and a second bone segment. In particularly preferred embodiments, each bone segment has a tissue (e.g., tendon or ligament) engaging surface and tissue is sandwiched between in an assembled BTB graft. Bone blocks comprising two bone segments are sometimes referred to as bone block assemblies or assembled bone blocks. When an assembled self fixing BTB of the present invention has a bone block assembly on each of its ends, the bone block assemblies may be the same or different.

It is also within the scope of the present invention that bone segments or bone blocks can be independently constructed from 1 to 30 bone portions, preferably from 1-10 bone portions, more preferably from 1 to 5 bone portions, even more preferably 1 to 3 bone portions, most preferably from 1 to 2 bone portions.

Embodiments of BTB grafts of the present invention are typically made from components that are autograft, allograft or xenograft. While autograft is the most immunologically acceptable material, its use necessitates an additional trauma to the patient which makes its use less acceptable. From a regulatory point of view, allograft material is preferred. From the perspective of relative abundance, xenograft material is preferred. From the perspectives of strength, machinability and cost, metal or ceramic materials are preferred. From the perspective of manufacturability and some degree of biocompatibility, synthetic polymer materials are preferred. From the perspective of enhanced biocompatibility and biomimetics, synthetic anorganic materials such as polymer or carbon nanofibers are preferred. When a BTB of the present invention is assembled from natural materials, it is within the scope of the present invention that it be constructed from autograft, allograft, xenograft or a combination of these. When a BTB of the present invention is assembled from synthetic materials, it is within the scope of the present invention that it be constructed from metals, ceramics, synthetic polymers, synthetic inorganics, or a combination of these. It is further contemplated within the scope of the present invention that a graft be assembled from any combination of autograft, allograft or xenograft tissue components, together with any combinations of metals, ceramics, or synthetic polymers. In one such embodiment for use in humans, the pins used to assemble the bone blocks are ceramic, the bone segments used to form the bone blocks are machined from xenograft bone and the tendon portion is preshaped from a harvested xenograft or allograft tendon.

It is also within the scope of the invention that the bone segments of the bone blocks may be made of artificial bone, by which is meant natural or synthetic materials including metals, ceramics polymers, composites or combinations thereof which exhibit properties similar to cortical bone. Commonly known examples are Poly L-Lactic Acid (PLLA) or calcium phosphate or hydroxyapatite based materials. These are available from various manufacturers such as U.S. Biomaterials, Alachua, Fla. and OsteoBiologics, Inc. (OBI), San Antonio, Tex. Artificial or natural bone constructs may also be enhanced by the addition of cultured autologous or allograft or xenograft cells or genetically modified cells which support bone growth and healing by the presence of or expression of growth factors, hormones, or cell lines involved in the healing process. Any cells added to the artificial or natural bone constructs may be selected, treated, genetically modified, processed or otherwise engineered to reduce negative effects such as antigencity, inflammation, rejection, or immune response by or against the host.

It is within the scope of the present invention that a self fixing BTB implant further comprise a tensioner (which may have one or more components). In some preferred embodiments, the tensioner spans the length of the exposed tendon and forceably engages the first and second bone blocks positioned on opposing ends of the tendon to exert a predetermined tension on the spanned tendon. A second function performed by some tensioners is acting as a spacer to hold the opposing bone blocks a predetermined distance from one another. In one embodiment, the tensioner is a pair of spacers on opposing faces of the exposed tendon. The pair of spacers are optionally held in place with one or more sutures. In a variation of this embodiment, as shown in FIGS. 6A-6B, the pair of spacers (tensioner) have through holes that run their length and align with corresponding holes in the bone blocks so that both the first and second bone blocks of the BTB graft and the tensioners are capable of being slidably inserted along prongs of an insertion tool, such as shown in FIGS. 5A-5D. In a further variation of this embodiment, the outside surface of the tensioner is threaded with threads that run in the same direction as the threads on one or more of the bone blocks, preferably on both bone blocks. In yet another embodiment, the threads on the tensioner are also continuous with the threads on one or more of the bone blocks, preferably on both bone blocks.

In yet another embodiment, the tensioner is a single spacer contacting the opposing bone blocks of the BTB and exerting tension on the tendon therebetween. In this embodiment, the tensioner has a slot for accommodating a portion of the tendon that is exposed between the bone blocks. In this embodiment, the tensioner optionally has at least one through hole running its length that aligns with one of the alignment holes on the opposing bone blocks. It is also within the scope of this embodiment that the tensioner is optionally threaded with threads that run in the same direction and pitch as threads on at least one of the bone blocks. When the tensioner of this embodiment is threaded, the tensioner typically has at least two holes that are aligned with the holes in the bone blocks and suited for receiving the prongs or pins of an insertion tool.

In another aspect, embodiments of the present invention relate to self fixing bone-tendon-bone (BTB) grafts for implantation through a tibial tunnel, the BTB grafts comprising a length of tendon or ligament (collectively "tendon") having two opposing ends, a first opposing end and a second opposing end, said first opposing end having a leading bone block attached thereto, said second opposing end having a trailing bone block attached thereto, said leading bone block and said trailing bone block each having an exterior surface that is threaded so that the threads run in the same direction, whereby the leading bone block and the trailing bone block are suited for simultaneous threading into tapped holes in a patient's femur and tibia, respectively.

In another aspect, embodiments of the present invention relate to assembled self fixing bone-tendon-bone (BTB) grafts, comprising a length of tendon or ligament (collectively "tendon") having two opposing ends, a first opposing end and a second opposing end, said first opposing end having a leading bone block attached thereto, said second opposing end having a trailing bone block attached thereto, said leading bone block and said trailing bone block each having an exterior surface that is threaded so that the threads run in the same direction, whereby the leading bone block and the trailing bone block are suited for simultaneous threading into tapped holes in a patient's femur and tibia, respectively. The leading bone block assembly comprises a first bone segment and a second bone segment sandwiching the first opposing end of the tendon therebetween. The first bone segment and the second bone segment each having a tendon engaging surface that is textured to grip the first opposing end of the tendon therebetween, and an exterior surface that is threaded such that in joined combination the threads are helically aligned, whereby in assembled combination, first bone segment and the second bone segment form the threaded first bone block assembly.

In yet another aspect of the present invention, an assembled self fixing bone-tendon-bone (BTB) graft for implantation through a tibial tunnel is provided, the BTB graft comprising a length of tendon or ligament (collectively "tendon") having two opposing ends, a first opposing end and a second opposing end, the first opposing end having a leading bone block assembly attached thereto, the second opposing end having a trailing bone block assembly attached thereto, the leading bone block assembly and the trailing bone block assembly each comprising a substantially cylindrical cross-section, and a tensioner disposed between the leading bone block assembly and the trailing bone block assembly; the tensioner configured to maintain tension in the tendon between the two bone block assemblies during implantation.

Suitable technology for producing intermediate bone blocks, bone blocks, and assembled embodiments of self fixing BTB grafts for use with the present invention is disclosed, for example, in commonly assigned U.S. patent application Ser. No. 11/313,280, filed Dec. 19, 2005, now pending; in commonly assigned U.S. Patent Publication No. 2003/0023304, published on Jan. 30, 2003; and in commonly assigned U.S. Pat. No. 6,893,462, issued May 17, 2005. Potentially suitable technology for producing intermediate bone blocks, bone blocks, and assembled embodiments of self fixing BTB grafts for use with the present invention is disclosed, for example, in U.S. Patent Publication No. 20010021875, to Enzerink, et. al., published on Sep. 13, 2001; and in U.S. Patent Publication No. 20050203623, to Steiner, et. al., published on Sep. 15, 2005. These and other known methods of assembling tendon to bone could potentially be adapted to support the present invention, with specific issues to be overcome including the potential weakness, low reproducibility, regulatory concerns and time requirements of suture as a primary fastening mechanism between bone and tendon, large amounts of tendon outside the bone blocks potentially interfering with the self-fixing features, and design constructs requiring cancellous bone which is weaker and more difficult to machine into a shape which will support the features required for a workable self fixing design. Particularly preferred technology for producing intermediate bone blocks, bone blocks, and assembled embodiments of self fixing BTB grafts for use with the present invention is disclosed in commonly assigned U.S. patent application Ser. No. 11/073,400, filed Mar. 4, 2005, now pending; U.S. Ser. No. 11/073,202, filed Mar. 4, 2005, now pending; and U.S. Ser. No. 11/073,281, filed Mar. 4, 2005, now pending, all of which are incorporated herein by reference.

In particular, certain embodiments of assembled self fixing BTB grafts of the present invention utilize the commonly assigned discovery that inserting one to ten cavities on the compressive surface (i.e., the soft tissue engaging surface) of a segment of a bone block ("bone segment") provides the bone segment with an unexpectedly superior grip on a tendon (or other soft tissue), relative to bone blocks of the prior art with untextured (smooth) or textured tissue engaging surfaces. Although not being bound by any particular theory, it is thought that the cavities on the tendon engaging face capture uncompressed tendon (or soft tissue) from above the cavity and the overflow of adjacent compressed tendon (or soft tissue) allowing the compressive surfaces of the bone block segment to grab and hold the tendon (or soft tissue) without damaging it, rather than simply floating on it. A preferred cavity is a channel cut into the tendon (or soft tissue) engaging face of a bone segment.

The cross-sectional shape of the cavities, and the layout of the cavities across the soft tissue engaging face of the bone block greatly affects the overall grip on a segment of soft tissue sandwiched between the tissue engaging faces of a first bone segment and an opposing bone segment. In embodiments of the present invention, one or more cavities have cross-sectional profiles that are rectangular, square, semicircular, semi-ovular, triangular, trapezoidal, sinusoidal, curvilinear, dovetail, omega or a combination thereof. Preferably, the cavity is undercut such that the body of the cavity is wider than its opening. More preferably, the cavity has an omega ("Ω") shaped cross-section, i.e., is an omega shaped cavity. By the term "omega" or "Ω" shaped cross section is meant that the lateral cross section of the cavity that is cut into the face of the bone segment has the shape of the Greek letter "Ω". By way of example, such an "Ω" shaped cavity is shown as element 29 of FIG. 2D herein.

These compression surfaces and cavities (i.e., enhanced gripping features) result in an assembled BTB graft that has various advantages. Some advantages that may be provided include, for example, full internal tendon capture, bone to bone contact at the healing interface, allowing the use of any suitable soft tissue (e.g., tendon) specimen, construction to a predetermined gage length, and adherence to preferred surgical techniques and fixation methods, while providing a significantly increased tensile strength over BTBs formed by stitching, stapling or compression alone.

When the cross-sectional shape of the cavity (preferably, a channel) is omega ("Ω") shaped, an even more enhanced gripping of the soft tissue (e.g., tendon) between the opposing faces of the bone blocks can be achieved. Without being bound by any particular theory, it is believed that the undercut shape of the omega cavity allows it to advantageously capture and hold the uncompressed and overflow soft tissue. Specifically, the omega cavity has a unique shape because it has a narrower mouth than the width of its cross section due to the fact that the face of the bone block is undercut and the undercut is rounded. This feature allows the soft tissue to enter the cavity and expand in a direction opposite to the direction of the compressed soft tissue immediately above on the tissue engaging surface of the bone block. The rounded profile also greatly reduces stress concentrations and allows the soft tissue to distribute the compressive load more evenly across the entire cavity. As a result, the omega cavity gently grips the soft tissue without cutting, and prevents it from slipping, sliding or flowing in the direction it is being pulled or squeezed. Moreover, unlike the edges of teeth or ridges (see FIGS. 3A-3D) that concentrate force on a tissue at all times during compression, the edge of the omega cavity only exerts force when needed in response to the tissue therein being pulled or squeezed. In addition, the narrow mouth of the omega cavity (or channel) on the bone block surface provides an additional benefit by maximizing contact (and thus grip) between the soft tissue (e.g., tendon) and the tissue-engaging surface of the bone block.

Any layout of the cavities and/or channels suitable for use with bone-tendon-bone grafts of the present invention, is also within the scope of this invention. Examples of bone blocks and bone segments suitable for use with the present invention can be found in commonly assigned U.S. patent applications Ser. No. 11/073,400, filed Mar. 4, 2005, now pending; U.S. Ser. No. 11/073,202, filed Mar. 4, 2005, now pending; U.S. Ser. No. 11/073,281, filed Mar. 4, 2005, now pending; and Ser. No. 11/313,280, filed Dec. 19, 2005, all of which are incorporated herein by reference. For example, a cavity can be a single hole in the surface of the bone block with an omega shaped sidewall. Alternatively, a cavity can be a pocket or larger hole made by removing an area of material with an undercut around some or all of the periphery. When the cavity is a single channel or a plurality of channels, the channel(s) can run in the direction of pull of the tendon, or across the direction of pull of the tendon, or at an angle to the direction of pull of the tendon. In one embodiment of the present invention, a bone segment has two channels with an omega cross-section running in the direction of pull of the tendon. See FIG. 11A.

In other embodiments of the present invention, the layout of the channels can be such that the channels intersect or cross one another. In one embodiment, a series of channels can be used that criss-cross one another to produce a waffle-like pattern on the tendon engaging face of the bone segment. In another embodiment, two channels can intersect one another to produce a "V" shaped layout on the tendon engaging face of the bone segment. This embodiment can also be thought of as a single channel that changes direction much like a bend in the road. It is within the scope of the present invention that the layout of channels include a single "V" shape, a plurality of "V" shapes, or some combination of different layouts. Other examples of layouts of the channels are "U" shaped, "W" shaped and "A" shaped. Alternative layouts for channels are graphic designs such as company insignia, random or psuedo-random designs such as a labyrinth or maze, or complex mathematically derived patterns such as fractal patterns.

A preferred layout for the channels is "U" shaped. The "U" shaped layout includes a single "U" or 2 to 10 "Us," which may be stacked or overlapped. Typically, the U's in the layout are stacked top to bottom. In a preferred embodiment, a set of three "U" channels are stacked top to bottom. In an especially preferred embodiment, a bone segment has a layout on its tendon engaging face of three stacked "U" shaped channels where each channel has an omega-shaped cross-section. This channel arrangement of three stacked "U" shapes can also be interpreted as a double stacked "A" shape.

It is also within the scope of the present invention that one or both ends of the bone block have the edge of the tendon engaging face reduced. Typically, this is performed by sanding, routing, grinding or cutting the edge to produce a round, beveled or chamfered edge. Preferably, this reduction of the end of the tendon engaging face results in an internal leading edge configuration that reduces tissue stresses during assembly and use. It is also within the scope of the present invention that the cross-sectional size of the cavities in any layout be the same or different. It is additionally within the scope of this invention for bone segments and bone blocks to have an overall lengthwise tapering profile.

The internal features such as cavities, channels, holes and textures are created on the bone blocks through careful application of conventional machining methods known in the art, using milling machines, lathes, router tables and the like. The external features such as threads, contours, grooves and slots are also created on the bone blocks through careful application of conventional machining methods known in the art. The complex geometry required by the external threads and contours makes computer controlled machining a preferred manufacturing method. Some features such as cavities, channels and textures are more readily created on each bone block individually for simplicity and efficiency of manufacture. Other features, including pin holes and external threads may either be made into each piece separately, or may be advantageously created on the assembled bone block as a whole to ensure proper form and alignment between mating features on adjacent bone portions.

Embodiments of bone block assemblies of the present invention are affixed to the end of a predetermined length of tendon by 1 to 30 biocompatible connectors that engage each of the two opposing bone blocks and the tendon that is sandwiched therebetween. Suitable biocompatible connectors include any connectors capable of holding the bone segments together as a unit (i.e., a bone block assembly). Some examples include pins that form an interference fit with holes machined in the bone blocks. Typical pins are made of stainless steel, titanium, or cortical bone. Preferred bone pins are cortical bone pins (i.e., pins made from cortical bone).

In some embodiments, a bone block assembly is made by stacking a first bone segment into an assembly fixture with its tendon engaging surface facing upward, then placing an end of a tendon into the fixture on top of the tendon engaging face, followed by stacking a second bone segment into the fixture such that its tendon engaging face engages the tendon. The assembly fixture is then tightened or clamped to hold the pieces in register while biocompatible connectors are installed. When the biocompatible connectors are pins, a drill is used to create holes through the assembly, then a reamer cleans and sizes the holes, and finally pins are pressed into the holes to hold the assembly together. The entire assembly is then treated through one or more cleaning or sterilization processes which produces an implantable graft without damaging the tissues in the graft. Alternatively, the components can be treated individually by an appropriate cleaning or sterilization process prior to assembly. In either case, the optional step of terminal sterilization is performed by methods known in the art such as gamma, e-beam, X-ray, or UV irradiation or by vapor phase hydrogen peroxide, or supercritical $CO_2$. Other optional steps include sterile packaging, and/or freezing or freeze drying.

BRIEF DESCRIPTION OF SEVERAL VIEWS OF THE DRAWINGS

FIGS. 1A-1B are views of one embodiment of a self fixing assembled BTB graft of the present invention. FIG. 1A is a top view of one embodiment of a self fixing assembled BTB graft of the present invention. FIG. 1B is a cross sectional view of the self fixing assembled BTB graft from FIG. 1A.

FIGS. 2A-2D are views of one embodiment of a first bone segment 1A of a bone block 1 of FIG. 1. FIG. 2A is a perspective view of one embodiment of a first bone segment showing the leading end of the bone segment and its threaded exterior surface. FIG. 2B is a side view of the embodiment of a first bone segment showing its threaded exterior surface. FIG. 2C is a bottom view of the embodiment of a first bone segment showing its textured tissue (e.g., tendon) engaging surface. FIG. 2D is a front end view of the embodiment of a first bone segment showing the leading end wherein the omega-shaped channels of the tissue engaging surface are visible.

FIG. 3A is a perspective view of one embodiment of a bone segment 3B showing the leading end of the bone segment, its textured tissue (e.g., tendon) engaging surface, and its opposing threaded exterior surface. FIG. 3B is a side view of the embodiment of a bone segment 3B showing its threaded exterior surface, and rows of ridged teeth angled against the direction of pull of the tendon. FIG. 3C is a bottom view of the embodiment of bone segment 3B showing the rows of angled ridges (teeth) on its tissue engaging surface. FIG. 3D is an enlarged detail of section 3D from FIG. 3B showing the teeth having angle a and height "H. " FIG. 3E is a front end view of the embodiment of bone segment 3B showing the leading end wherein the holes for the insertion tool and the texture of the tissue engaging surface are clearly visible.

FIGS. 4A-4D are views of one embodiment of a tendon tensioner for spacing opposing assembled bone blocks and applying tension to the tendon in embodiments of self fixing assembled BTBs of the present invention. FIG. 4A is a perspective view of the first member of a two-member tendon tensioner showing through-holes of a predetermined diameter for slideably receiving the corresponding prongs of an insertion tool, and further showing a groove for accommodating the exposed length of tendon in the assembled BTB. The second member (not shown) can be the same or different than the first member and would be sutured to first member by a suture in the suture hole. FIG. 4B is a top view of tendon tensioner having a suture hole and through holes. FIG. 4C is a side view of tensioner showing it's through holes and suture hole. FIG. 4D is an end view of the tensioner looking down its through holes.

FIGS. 5A-5D are views of one embodiment of a hand operated insertion tool for simultaneously inserting (threading) the leading block of a self fixing assembled BTB of the present invention into a tapped (threaded) hole in a femur and the trailing block into the tapped (threaded) bone tunnel in the tibia of the recipient patient. FIG. 5A is a perspective view of one embodiment of an insertion tool having four prongs that correspond to four sets of aligned holes shown in the first and second bone blocks in the embodiment of the self fixing assembled BTB graft of FIGS. 1A-1B. FIG. 5B is a top view of the insertion tool. FIG. 5C is a head on view of the pronged end of the insertion tool showing that in this embodiment the 4 prongs are optionally two opposing pairs of prongs of different diameters which allow for a specific orientation of the BTB on the implantation tool. FIG. 5D is a side view of the insertion tool, showing the two different sizes (diameters) of the prongs used to align and simultaneously thread the opposing bone blocks of one embodiment of an assembled self-threading BTB of the invention.

FIG. 6A shows an exploded view of a BTB implant comprising the self fixing assembled BTB of FIGS. 1A-1B, the tensioner (pair) of FIGS. 4A-4D, and the insertion tool of FIGS. 5A-5D. FIG. 6B shows this embodiment of a BTB implant comprising a self fixing assembled BTB of FIGS. 1A-1B with the tensioner of FIGS. 4A-4D in place, and positioned on the insertion tool of FIGS. 5A-5D for insertion (threading) into appropriately drilled, and optionally tapped, holes in the tibia and femur of a patient in need of tendon replacement, repair or augmentation.

FIGS. 7A-7D show various views of a semi-capsule shaped embodiment of a bone segment preferably used as a trailing bone block of one embodiment of the present invention having two substantially parallel channels with an omega-shaped cross section running substantially in the intended direction of pull (arrow) of a segment of soft tissue (e.g., tendon). Alternatively, this embodiment may also be used with alternative or secondary fixation as part of a leading bone block. FIG. 7A is a perspective view showing holes for receiving a biocompatible connector (e.g., pin or other connector) that would hold the depicted bone segment to any one of a variety of appropriately shaped opposing bone segments and a segment of soft tissue sandwiched therebetween. FIG. 7A also shows the exterior surface having a curved notch or groove for maximizing engagement with an interference screw. FIG. 7C is a bottom view showing the channels 77 in the tissue engaging surface and the pattern of pin holes 72. FIG. 7B is a side view showing the semi-capsular shape of this bone segment. FIG. 7D is an end view showing the groove on the exterior surface and the channels on the tissue engaging surface.

FIGS. 8A-8D show views of one embodiment of a bone segment of the present invention having an alternate embodiment for the exterior surface thereof. The exterior surface can be described as a series of crush ribs and can be used in a press fit fixation method. FIG. 8A is a perspective view of this embodiment showing holes for receiving a biocompatible connector, e.g., pin or other connector, (pin holes) that would hold this bone segment to any one of a variety of other appropriately shaped bone segments and to a segment of soft tissue sandwiched therebetween. Also shown on the exterior surface of this embodiment are ridges suitable for gripping a bone tunnel and reducing slippage in the direction of pull (arrow) of the tendon. FIG. 8B is a side view of the opposing bone block showing its semi-capsular shape. FIG. 8C is a top view of the exterior surface of this bone segment looking directly down at its capsule shape and the position of the pin holes. FIG. 8D is an end view of the bone segment of FIG. 8A.

FIGS. 9A-9D are views of another embodiment of a BTB graft of the present invention. FIG. 9A is an exploded perspective view of a preferred embodiment of an assembled BTB graft of the present invention. In this exploded perspective view, the BTB graft is composed of two assembled bone block assemblies, one on each of the opposing ends of a segment of soft tissue. FIG. 9B is a side view of the assembled BTB graft showing the soft tissue (e.g., tendon) sandwiched between opposing bone segments at each end. FIG. 9C is a top view of the assembled BTB. FIG. 9D is an end view of the assembled BTB showing the soft tissue (e.g., tendon) sandwiched between opposing bone segments. FIG. 9D further shows the bone block-tissue assembly as being generally cylindrical, having the approximate diameter of a bone tunnel into which it can be inserted, and a groove for maximizing contact with an interference screw.

FIG. 10A is a perspective view of this embodiment. FIG. 10B is a top view of this embodiment. FIG. 10C is a side view of this embodiment. FIG. 10D is an end view of this embodiment.

FIGS. 11A-11D are views of one embodiment of a first bone segment of a bone segment for use in BTB grafts of the present invention. FIG. 11A is a perspective view of one embodiment of a bone segment showing the leading end of the bone segment, and the tissue engaging surface of the bone segment having two substantially parallel omega channels therein. FIG. 11B is a side view of the embodiment showing its threaded exterior surface. FIG. 11C is a view of the embodiment looking through the bone segment. FIG. 11D is a front end view of the embodiment showing the leading end wherein the omega-shaped channels of the tissue engaging surface, and the holes for receiving the prongs of an insertion tool, are visible.

FIGS. 12A-12E are views of one embodiment of a bone segment of a bone block for use in BTB grafts. FIG. 12A is a perspective view of one embodiment of a bone segment showing the leading end of the bone segment, and its threaded exterior surface. Two holes are shown for receiving the prongs of an insertion tool. FIG. 12B is a side view of the embodiment of a bone segment showing its threaded exterior surface, and rows of ridged teeth on its textured tissue (e.g., tendon) engaging surface. The teeth as shown are angled against the direction of pull of the tendon. FIG. 12C is a bottom view of the embodiment of bone segment showing the rows of ridged teeth on its textured tissue (e.g., tendon) engaging surface. FIG. 12D is an front end view of the embodiment of bone segment showing the leading end wherein the holes for the insertion tool and the texture of the tissue engaging surface are also shown. FIG. 12E is an enlarged detail of section D from FIG. 12B showing the angled teeth.

FIGS. 13A-13B are views of another embodiment of a self fixing assembled BTB graft of the present invention having aligned holes through the leading and trailing bone block assemblies to receive a pronged insertion tool. In this embodiment, the bone segments of FIGS. 11 and 12 have been combined to form each of the first and second bone block assemblies. FIG. 13A is a top view of this embodiment of a self fixing assembled BTB graft of the present invention. FIG. 13B is a cross sectional view of section BB of FIG. 13A of this embodiment of a self fixing assembled BTB graft of the present invention.

FIGS. 14A-14B are views of another embodiment of a self fixing assembled BTB graft of the present invention. FIG. 14A is a top view of this embodiment of a self fixing assembled BTB graft of the present invention. FIG. 14B is a cross sectional view of section BB of FIG. 14A of this embodiment of a self fixing assembled BTB graft of the present invention.

FIGS. 15A-15B are views of another embodiment of a self fixing assembled BTB graft of the present invention having tapered leading end on the leading bone block. FIG. 15A is a top view of this embodiment of a self fixing assembled BTB of the present invention. FIG. 15B is a cross sectional view of section BB of FIG. 15A of this embodiment of a self fixing assembled BTB of the present invention.

FIGS. 16A-16B are views of a preferred embodiment of a self fixing assembled BTB graft of the present invention, wherein the leading bone block assembly has a smaller outer diameter (or cross-section) than the trailing bone block assembly. FIG. 16A is a top view of this embodiment of a self fixing assembled BTB graft of the present invention. As shown, the leading bone block and the trailing bone block have buttressed threads that run in opposite directions and have opposing thread angles. Alternatively, the threads may be configured to run in the same direction, with either the same or opposite thread angle, or with symmetric threads. FIG. 16B is a cross sectional view of Section BB of FIG. 16A showing this embodiment of a self fixing assembled BTB graft of the present invention.

FIGS. 17A-17B are views of one embodiment of a self fixing assembled BTB graft of the present invention having aligned internal slotted grooves through the interior of the bone blocks to receive an insertion tool. FIG. 17A is a top view of this embodiment of a self fixing assembled BTB graft of the present invention. As shown, the leading bone block and the trailing bone block have aligned buttressed threads. FIG. 17B is a cross sectional view of section BB of FIG. 17A showing this embodiment of a self fixing assembled BTB graft of the present invention.

FIG. 18A is a perspective view of one embodiment of a first bone segment showing the leading end of the bone segment and the tissue engaging surface having two substantially parallel omega channels therein. FIG. 18B is a side view of the embodiment of a first bone segment showing its threaded exterior surface. FIG. 18C is a bottom view of the embodiment of a first bone segment showing the channels in its tissue engaging surface. FIG. 18D is a front end view of the embodiment of a first bone segment having omega-shaped channels in the tissue engaging surface and an internal slotted groove through the interior of the bone block to receive an insertion tool.

FIG. 19A is a perspective view of one embodiment of a bone segment showing the leading end of the bone segment, and its threaded exterior surface. An internal slotted groove through the interior of the bone block to receive an insertion tool is also shown. FIG. 19B is a side view of the embodiment of a bone segment showing its threaded exterior surface, and rows of ridged teeth on the textured tissue (e.g., tendon) engaging surface. The teeth as shown are angled against the direction of pull of the tendon. FIG. 19C is a bottom view of the embodiment of bone segment showing its textured tissue engaging surface. FIG. 19D is an front end view of the embodiment of bone segment showing the leading end wherein the internal slotted groove for the insertion tool and the texture of the tissue engaging surface are also shown. FIG. 19E is an enlarged detail of section E from FIG. 19B showing the angled teeth.

FIG. 20A is a perspective view of a pair of members of a two-member tendon tensioner showing arced grooves along their length for slideably receiving the corresponding prongs of an insertion tool. FIG. 20B is a side view of the two members of the tensioner. FIG. 20C is a top view of one member of the two-member tensioner. FIG. 20D is an end view of the two members of a two-member tensioner, looking down the arced grooves therein for slideably receiving the corresponding prongs of an insertion tool.

FIG. 21A is a perspective view of one embodiment of an insertion tool having four prongs, where all of the prongs have the same diameter as the other prongs. This embodiment can be used with BTBs of FIG. 1 when the aligned holes of the opposing bone segments of the bone blocks have the same diameter. This embodiment can also be used with BTBs of FIG. 17. FIG. 21B is a side view of the insertion tool. FIG. 21C is a head on view of the pronged end of the insertion tool. FIG. 21D is a top view of the insertion tool, showing the prongs used to align and simultaneously thread the opposing bone blocks of an assembled self fixing BTB.

FIG. 22A shows the self fixing assembled BTB of FIGS. 17A-17B with the tensioner of FIGS. 20A-20D in place, and positioned on the insertion tool of FIGS. 21A-21D for insertion (threading) into appropriately drilled, and optionally tapped, holes in the tibia and femur of a patient in need of tendon replacement, repair or augmentation. FIG. 22B shows an exploded view of a self fixing assembled BTB of FIGS. 17A-17B, the tensioner (pair) of FIGS. 20A-20D, and the insertion tool of FIGS. 21A-21D.

FIGS. 23A-23B are views of one embodiment of a self fixing assembled BTB graft of the present invention having aligned internal slotted grooves through the interior of the bone blocks to receive an insertion tool. The internal slotted grooves of this embodiment have a curved profile. FIG. 23A is a top view of this embodiment of a self fixing assembled BTB graft of the present invention. As shown, the leading bone block and the trailing bone block have aligned buttressed threads. FIG. 23B is a cross sectional view of this embodiment of a self fixing assembled BTB of the present invention.

FIG. 24A is a perspective view of one embodiment of a first bone segment showing the leading end of the bone segment and the tissue engaging surface having two substantially parallel omega channels therein. FIG. 24B is a side view of the embodiment of a first bone segment showing its threaded exterior surface, as well as showing one of the omega channels in the tissue engaging surface and the slot through the bone segment for receiving an insertion tool. FIG. 24C is a bottom view of the embodiment of a first bone segment showing the threaded exterior surface and looking through the bone segment to the channels 249 on the tissue engaging surface. FIG. 24D is a front end view of the embodiment of a first bone segment showing the leading end having omega-shaped channels in the tissue engaging surface and a curved slot through the interior of the bone block to receive an insertion tool.

FIG. 25A is a perspective view of one embodiment of a bone segment showing the leading end of the bone segment, its threaded exterior surface, and a slot therethrough having a curved profile for receiving an insertion tool. FIG. 25B is a side view of the embodiment of a bone segment showing its threaded exterior surface, and rows of ridged teeth on the textured tissue (e.g., tendon) engaging surface. The teeth as shown are angled against the direction of pull of the tendon. FIG. 25C is a bottom view of the embodiment of bone segment showing its textured tissue engaging surface. FIG. 25D is a front end view of the embodiment of bone segment showing the leading end, the slot for the insertion tool, and the texture of the tissue engaging surface. FIG. 25E is an enlarged detail of section E from FIG. 25B showing the angled teeth.

FIG. 26A is a perspective view of a pair of members of a two-member tendon tensioner showing slots therethrough having a curved profile for receiving an insertion tool. FIG. 26B is a side view of the two members of the tensioner. FIG. 26C is a top view of one member of the two-member tensioner. FIG. 26D is an end view of the two members of a two-member tensioner, looking down the curved slots therethrough for slideably receiving the corresponding prongs of an insertion tool.

FIG. 27A is a perspective view of one embodiment of an insertion tool having two prongs, each of which has a curved elongated profile configured to be slidably received by the curved slots in BTB grafts such as those of FIG. 23. FIG. 27C is a head on view of the pronged end of the insertion tool. FIG. 27D is a side view of the insertion tool, showing the prongs used to align the opposing bone blocks of an assembled self fixing BTB graft.

FIG. 28A shows the self fixing assembled BTB of FIGS. 23A-23B with the tensioner of FIGS. 26A-26D in place, and positioned on the insertion tool of FIGS. 27A-27D for insertion (threading) into appropriately drilled, and optionally tapped, holes in the tibia and femur of a patient in need of tendon replacement, repair or augmentation. FIG. 28B shows an exploded view of a self fixing assembled BTB of FIGS. 23A-23B, the tensioner (pair) of FIGS. 26A-26D, and the insertion tool of FIGS. 27A-27D.

FIGS. 29A-29B are views of one embodiment of a self fixing assembled BTB of the present invention having an external slotted groove on each of the bone blocks to receive an insertion tool. The external slotted grooves of this embodiment have a rectangular profile. FIG. 29A is a top view of this embodiment of a self fixing assembled BTB of the present invention. As shown, the leading bone block and the trailing bone block have aligned buttressed threads. FIG. 29B is a cross sectional view of section AA of FIG. 29A showing this embodiment of a self fixing assembled BTB of the present invention.

FIG. 30A is a perspective view of one embodiment of a first bone segment showing the leading end of the bone segment and the tissue engaging surface having two substantially parallel omega channels therein. FIG. 30B is a side view of the embodiment of a first bone segment showing its threaded exterior surface. FIG. 30C is a top view of the embodiment of a first bone segment showing the threaded exterior surface and the external slotted groove along a portion of the length thereof. FIG. 30D is an end view of the embodiment of a first bone segment showing the leading end having omega-shaped channels in the tissue engaging surface and an external slotted groove on the bone block to receive an insertion tool.

FIG. 31A is a perspective view of one embodiment of a bone segment showing the leading end of the bone segment, its threaded exterior surface, and an external slotted groove for receiving an insertion tool. FIG. 31B is a side view of the embodiment of a bone segment showing its threaded exterior surface, and rows of ridged teeth on the textured tissue (e.g., tendon) engaging surface. The teeth as shown are angled against the direction of pull of the tendon. FIG. 31C is a bottom view of the embodiment of bone segment showing its textured tissue engaging surface. FIG. 31D is an end view of the embodiment of the bone segment showing the external slotted groove for the insertion tool, and the texture of the tissue engaging surface. FIG. 31E is an enlarged detail of section A from FIG. 31B showing the angled teeth.

FIG. 32A is a perspective view of one member of a pair of members that would be used with the BTB, having a rectangular notch therein for receiving a corresponding prong on an insertion tool. FIG. 32B is a side view of the tensioner member. FIG. 32C is a horizontal view of the tensioner member. FIG. 32D is a vertical view of the tensioner member.

FIGS. 33A-33D are views of one embodiment of a hand operated insertion tool for simultaneously inserting the leading block of a self fixing assembled BTB of FIG. 29. FIG. 33A is a perspective view of one embodiment of an insertion tool having two prongs, each of which has a rectangular profile configured to be slidably received by the external slotted grooves in the BTBs of FIG. 29. FIG. 33C is a head on view of the pronged end of the insertion tool. FIG. 33D is a side view of the insertion tool, showing the prongs used to align the opposing bone blocks of an assembled self fixing BTB.

FIG. 34A shows the self fixing assembled BTB of FIGS. 29A-29B with the tensioner of FIGS. 32A-32D in place, and positioned on the insertion tool of FIGS. 33A-33D for insertion (threading) into appropriately drilled, and optionally tapped, holes in the tibia and femur of a patient in need of tendon replacement, repair or augmentation. FIG. 34B shows an exploded view of a self fixing assembled BTB of FIGS. 29A-29B, the tensioner (pair) of FIGS. 32A-32D, and the insertion tool of FIGS. 33A-33D.

Figure 3A:
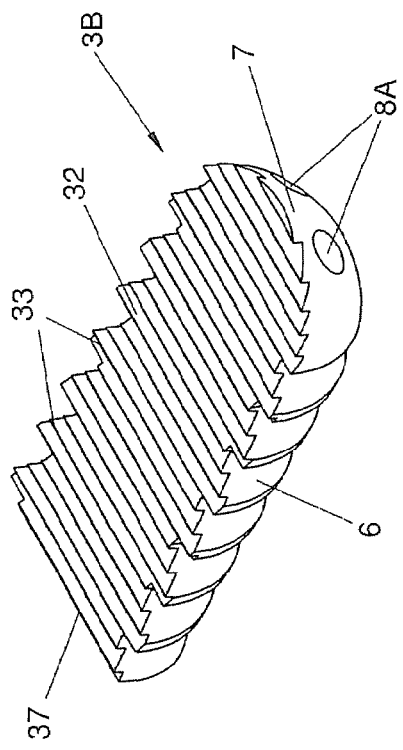
FIGS. 3A-3E are views of one embodiment of a second bone segment of a bone block of FIG. 1.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

The present invention has multiple aspects. In a first aspect, the present invention relates to self fixing bone-tendon-bone (BTB) grafts and implants that are useful in a mammalian patient in need of tendon replacement, repair or augmentation. In one embodiment, a self fixing bone-tendon-bone (BTB) graft comprises a length of tendon or ligament (collectively "tendon") having two opposing ends, a first opposing end and a second opposing end, wherein a first bone block is attached to the first opposing end of the tendon and a second bone block is attached to the second opposing end of the tendon.

More specifically, in one embodiment, a self fixing bone-tendon-bone (BTB) graft of the present invention comprises a length of tendon or ligament (collectively "tendon") having two opposing ends, a first opposing end and a second opposing end, wherein a first bone block is attached to said first opposing end of said tendon and a second bone block is attached to said second opposing end of said tendon, and wherein at least one of said first bone block or said second bone block has an exterior surface having threads along at least a portion thereof. In one aspect of such an embodiment, each of said first bone block and said second bone block has an exterior surface having threads along at least a portion thereof, and wherein the threads of said first bone block and said second bone block run in the same direction so that each bone block is implantable in a respective hole in opposing bones of a joint on a patient when the BTB is rotated as a whole in the threaded direction.

Another embodiment provides a self fixing bone-tendon-bone (BTB) graft comprising a length of tendon or ligament (collectively "tendon") having two opposing ends, a first opposing end and a second opposing end, said first opposing end having a leading bone block attached thereto, said second opposing end having a trailing bone block attached thereto, said leading bone block and said trailing bone block each having an exterior surface that is threaded so that the threads run in the same direction, whereby the leading bone block and the trailing bone block are suited for simultaneous threading into tapped holes in a patient's femur and tibia, respectively.

In another embodiment, an assembled self fixing bone-tendon-bone (BTB) graft of the present invention comprises a length of tendon or ligament (collectively "tendon") having two opposing ends, a first opposing end and a second opposing end, the first opposing end having a leading bone block assembly attached thereto, the second opposing end having a trailing bone block assembly attached thereto, the leading bone block assembly and the trailing bone block assembly each comprising a substantially cylindrical cross-section and an exterior surface that is threaded so that the threads run in the same direction, whereby the leading bone block assembly and the trailing bone block assembly are suited for simultaneous threading into tapped holes in a patient's femur and tibia, respectively; the leading bone block assembly comprises a first bone segment and a second bone segment sandwiching the first opposing end of said tendon therebetween, the first bone segment and the second bone segment each having a tendon engaging surface that is textured to grip the first opposing end of the tendon therebetween, and an exterior surface that is threaded such that in joined combination the first bone segment and the second bone segment form the threaded leading bone block assembly.

Yet another embodiment of the present invention provides an assembled self fixing bone-tendon-bone (BTB) graft for implantation through a tibial tunnel, the BTB graft comprising a length of tendon or ligament (collectively "tendon") having two opposing ends, a first opposing end and a second opposing end, the first opposing end having a leading bone block assembly attached thereto, the second opposing end having a trailing bone block assembly attached thereto, the leading bone block assembly and the trailing bone block assembly each comprising a substantially cylindrical cross-section, and a tensioner disposed between the leading bone block assembly and the trailing bone block assembly; the tensioner configured to maintain tension in the tendon between the two bone block assemblies during implantation.

Tendons

As discussed above, the term "tendon" refers to a length of tendon, a bundle of tendons of the same or different lengths, a length of ligament, a bundle of ligaments of the same length or different lengths, a segment or segments of pericardium, dermis or fascia, or a combination thereof. The tendons can be of the same thickness or of different thicknesses. The tendons can also be of the same cross-sectional area or of different cross-sectional areas. Preferably, the tendon is a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof.

The tendon (soft tissue) portion of BTB grafts is typically autograft, allograft or xenograft. It is also contemplated, however, that a tendon be an engineered construct of natural or synthetic origin, such as a synthetic ligament repair scaffold, other flexible synthetic biomaterial, or specially formulated natural material such as that disclosed in the applicant's copending applications U.S. Ser. No. 10/754,310, entitled "Matrix Composition For Human Grafts/Implants" and filed Jan. 9, 2004, and in U.S. Ser. No. 10/793,976, entitled "Muscle-Based Grafts/Implants" and filed Mar. 5, 2004. Engineered constructs include, for example, processed collagen-based tissue matrix, such as the product sold under the trade name GraftJacket®, by Wright Medical Technology, Inc., Arlington, Tenn.

Preferably, the source of the soft tissue is allograft or xenograft. When the recipient patient is a human, the source is preferably human allograft. However, in some situations, particularly in tendon repair, a tendon bundle comprising a xenograft tendon bundle or a combination of allograft and xenograft tendons of different thicknesses and lengths, provides for enhanced performance under extreme stresses.

As used herein, the term "bundle" refers to 1-10 discrete tendons or ligaments, which themselves can be made up of smaller fibers of tendons/ligaments that are stapled, glued, sutured, woven or braided. Alternatively, tendons or other soft tissues are crosslinked with a crosslinking agent. In another alternate embodiment, the segment of soft tissue is sufficiently large so that excess tissue extends beyond the end or sides of a bone block assembly. This excess soft tissue is useful for surgical placement and/or fixation.

By selecting a bundle of tendons or ligaments of different length, or a combination thereof, an assembled BTB of the present invention can be tailored to the needs of the patient. For example, when two of the shorter ligaments stretch under strain to the length of one or more longer ligaments, the restraint posed by the longer ligaments engages and acts to stabilize the joint. By having a BTB with two to four lengths of ligament, tendon or a combination thereof, a reconstructed tendon can have multiple fall back positions to stabilize a joint. This effect can also be achieved by utilizing assemblies that contain 3 or more bone blocks. Alternatively, multiple tendons can be designed to have multiple points of attachment or rotation, mimicking the structure and function of the multi-bundled native anterior cruciate ligament (ACL) construct. Such construction is particularly useful for anterior cruciate reconstruction in a human knee joint. By varying the number and length of ligaments or tendons in a bundle, an assortment of BTBs can be made that would be customized and suitable for a range of patients from the 65-year-old recreational shuffleboard enthusiast to the 25 year old star professional football running back.

Typical lengths for the tendon depends upon the application and the size of the patient. In the case of a BTB intended for anterior cruciate ligament repair in a human patient, the length of the soft tissue between the bone blocks can range from about 32 mm to about 58 mm, preferably from about 38 mm to about 52 mm, and more preferably from about 42 mm to about 48 mm.

Bone Blocks and Bone Segments

Assembled self fixing BTB grafts of the present invention may have a bone block on only one end of the tendon, or on each end thereof. When the BTB graft has only one bone block on one end of the tendon, it is referred to as a bone-tendon, or BT graft.

Bone blocks suitable for use with the present invention can comprise one or more bone segments. In preferred embodiments, a bone block comprises a first bone segment and a second bone segment. In particularly preferred embodiments, each bone segment has a tissue (e.g., tendon or ligament) engaging surface and tissue is sandwiched between. Bone blocks comprising two bone segments are sometimes referred to as bone block assemblies or assembled bone blocks. Alternative embodiments of shapes for the exterior surface of a bone segment or bone block assembly include but are not limited to polygonal, cylindrical, threaded, bulleted, chamfered, angled, ridged, capsule shaped, tapered or a combination thereof. When an assembled self fixing BTB of the present invention has a bone block assembly on each of its ends, the bone block assemblies may be the same or different.

It is also within the scope of the present invention that bone segments or bone blocks can be independently constructed from 1 to 30 bone portions, preferably from 1-10 bone portions, more preferably from 1 to 5 bone portions, even more preferably 1 to 3 bone portions, most preferably from 1 to 2 bone portions. In certain embodiments, the bone portions are cortical bone, cancellous bone, artificial bone or a combination thereof. Preferably, the bone block portions are cortical bone, cancellous bone or a combination thereof. More preferably, the bone block portions are cortical bone. Typically, a majority of the bone portions are cortical bone.

Embodiments of bone blocks and bone segments of the present invention are typically made from components that are autograft, allograft or xenograft, or artificial. Preferably, the bone source is allograft or xenograft bone. While autograft is the most immunologically acceptable material, its use necessitates an additional trauma to the patient which makes its use less acceptable. Additionally, because preferred embodiments of bone segments and bone blocks are machined, the bone source is typically allograft, xenograft, or artificial bone. When the recipient patient is a human, the bone source is preferably human allograft bone. Due to constraints of human allograft availability and current advances in the use and processing of xenografts, there are also some cases where the bone source is preferably xenograft bone, and more preferably xenograft bone treated to reduce antigenicity and immune response.

It is also within the scope of the invention that the bone segments of the bone blocks may be made of artificial bone, by which is meant natural or synthetic materials including metals, ceramics polymers, composites or combinations thereof which exhibit properties similar to cortical bone. Commonly known examples are Poly L-Lactic Acid (PLLA) or calcium phosphate or hydroxyapatite based materials. These are available from various manufacturers such as U.S. Biomaterials, Alachua, Fla., and OsteoBiologics, Inc. (OBI), San Antonio, Tex. Artificial or natural bone constructs may also be enhanced by the addition of cultured autologous or allograft or xenograft cells or genetically modified cells which support bone growth and healing by the presence of or expression of growth factors, hormones, or cell lines involved in the healing process. Any cells added to the artificial or natural bone constructs may be selected, treated, genetically modified, processed or otherwise engineered to reduce negative effects such as antigenicity, inflammation, rejection, or immune response by or against the host.

When a BTB of the present invention is assembled from natural materials, it is within the scope of the present invention that it be constructed from autograft, allograft, xenograft or a combination of these. When a BTB of the present invention is assembled from synthetic materials, it is within the scope of the present invention that it be constructed from metals, ceramics, synthetic polymers, synthetic inorganics, or a combination of these. It is further contemplated within the scope of the present invention that the graft be assembled from any combination of autograft, allograft or xenograft tissue components, together with any combinations of metals, ceramics, or synthetic polymers. In some cases BTB grafts of the present technology comprising a combination of allograft, xenograft, synthetic or artificial tissues offers advantages in strength, fixation, mechanical properties, biochemical properties, healing, design freedom and/or availability. In one embodiment, a BTB is constructed of synthetic or allograft or autograft tendon, with a xenograft bone block assembly at one or both ends. In a second embodiment, a BTB is constructed of artificial or allograft bone with xenograft tendons. In a third embodiment, an allograft tendon is attached to a conventional bone block by a naturally occurring attachment at one end, and attached to a xenograft or artificial bone block assembly at the other end. In yet other embodiments, a combination of allograft and xenograft tendons is assembled with a combination of allograft or xenograft or synthetic bone blocks. In one preferred embodiment for use in humans, the pins used to assemble the bone blocks are ceramic, the bone segments used to form the bone blocks are machined from xenograft bone and the tendon portion is preshaped from a harvested xenograft or allograft tendon.

From a regulatory point of view, allograft material is preferred. From the perspective of relative abundance, xenograft material is preferred. From the perspectives of strength, machinability and cost, metal or ceramic materials are preferred. From the perspective of manufacturability and some degree of biocompatibility, synthetic polymer materials are preferred. From the perspective of enhanced biocompatibility and biomimetics, synthetic anorganic materials such as polymer or carbon nanofibers are preferred.

Methods for obtaining a tendon that is naturally attached to a block of bone is disclosed commonly assigned U.S. Pat. No. 6,497,726, entitled "Materials and methods for improved bone tendon bone transplantation" which issued on Dec. 24, 2002, and in commonly assigned U.S. Pat. No. 6,805,713, entitled "Materials and methods for improved bone tendon bone transplantation" which issued on Oct. 19, 2004, both of which are expressly incorporated herein by reference in relation to their disclosure on BTBs and on obtaining a tendon naturally attached to a bone block. A tendon that is naturally attached to one or more bone block(s) may be adapted to accept an insert and tensioner of the present invention. Partial threads may be cut into the cancellous portion found in a naturally attached bone block. Alternatively, full threads may be cut through the bone block and the attached tendon. Preferably, the naturally attached bone blocks are used as a component of an assembled BTB graft, thus realizing the benefits of strong natural attachment together with the added functionality and benefits of the present invention. Naturally attached bone blocks are typically comprised primarily of cancellous bone with a thin cortical cap at the tendon attachment. This cancellous bone is weaker and more difficult to shape or machine than cortical bone. Therefore, it is preferred when working with naturally attached cancellous bone blocks (or any cancellous bone blocks) to further assemble cortical pieces outside the cancellous, then use the cortical pieces to incorporate threading or other features of the present invention.

Suitable technology for producing intermediate bone blocks, bone blocks, and assembled embodiments of self fixing BTB grafts for use with the present invention is disclosed, for example, in commonly assigned U.S. patent application Ser. No. 11/313,280, filed Dec. 19, 2005, now pending; in commonly assigned U.S. Patent Publication No. 2003/0023304, published on Jan. 30, 2003; and in commonly assigned U.S. Pat. No. 6,893,462, issued May 17, 2005. Potentially suitable technology for producing intermediate bone blocks, bone blocks, and assembled embodiments of self fixing BTB grafts for use with the present invention is disclosed, for example, in U.S. Patent Publication No. 20010021875, to Enzerink, et. al., published on Sep. 13, 2001; and in U.S. Patent Publication No. 20050203623, to Steiner, et. al., published on Sep. 15, 2005. These and other known methods of assembling tendon to bone could potentially be adapted to support the present invention, with specific issues to be overcome including the potential weakness, low reproducibility, regulatory concerns and time requirements of suture as a primary fastening mechanism between bone and tendon, large amounts of tendon outside the bone blocks potentially interfering with the self-fixing features, and design constructs requiring cancellous bone which is weaker and more difficult to machine into a shape which will support the features required for a workable self fixing design. Particularly preferred technology for producing intermediate bone blocks, bone blocks, and assembled embodiments of self fixing BTB grafts for use with the present invention is disclosed in commonly assigned U.S. patent application Ser. No. 11/073,400, filed Mar. 4, 2005, now pending; U.S. Ser. No. 11/073,202, filed Mar. 4, 2005, now pending; and U.S. Ser. No. 11/073,281, filed Mar. 4, 2005, now pending, all of which are incorporated herein by reference.

In particular, certain embodiments of assembled self fixing BTB grafts of the present invention utilize the commonly assigned discovery that inserting one to ten cavities on the compressive surface (i.e., the soft tissue engaging surface) of a segment of a bone block ("bone segment") provides the bone segment with an unexpectedly superior grip on a tendon (or other soft tissue), relative to bone blocks of the prior art with untextured (smooth) or textured tissue engaging surfaces. Although not being bound by any particular theory, it is thought that the cavities on the tendon engaging face capture uncompressed tendon (or soft tissue) from above the cavity and the overflow of adjacent compressed tendon (or soft tissue) allowing the compressive surfaces of the bone block segment to grab and hold the tendon (or soft tissue) without damaging it, rather than simply floating on it. A preferred cavity is a channel cut into the tendon (or soft tissue) engaging face of a bone segment.

The cross-sectional shape of the cavities, and the layout of the cavities across the soft tissue engaging face of the bone block greatly affects the overall grip on a segment of soft tissue sandwiched between the tissue engaging faces of a first bone segment and an opposing bone segment. In some embodiments of the present invention, one or more cavities have cross-sectional profiles that are rectangular, square, semi-circular, semi-ovular, triangular, trapezoidal, sinusoidal, curvilinear, dovetail, omega or a combination thereof. Preferably, the cavity is undercut such that the body of the cavity is wider than its opening. More preferably, the cavity has an omega ("Ω") shaped cross-section, i.e., is an omega shaped cavity. By the term "omega" or "Ω" shaped cross section is meant that the lateral cross section of the cavity that is cut into the face of a bone segment has the shape of the Greek letter "Ω". By way of example, such an "Ω" shaped cavity is shown as element 29 of FIG. 2D herein.

These compression surfaces and cavities (i.e., enhanced gripping features) result in an assembled BTB graft that has various advantages. Some of the that may be provided include full internal tendon capture, bone to bone contact at the healing interface, allowing the use of any suitable soft tissue (e.g., tendon) specimen, construction to a predetermined gage length, and adherence to preferred surgical techniques and fixation methods, while providing a significantly increased tensile strength over BTBs formed by stitching, stapling or compression alone.

When the cross-sectional shape of the cavity (preferably, a channel) is omega ("Ω") shaped, an even more enhanced gripping of the soft tissue (e.g., tendon) between the opposing faces of the bone blocks can be achieved. Without being bound by any particular theory, it is believed that the undercut shape of the omega cavity allows it to advantageously capture and hold the uncompressed and overflow soft tissue. Specifically, the omega cavity has a unique shape because it has a narrower mouth than the width of its cross section due to the fact that the face of the bone block is undercut and the undercut is rounded. This feature allows the soft tissue to enter the cavity and expand in a direction opposite to the direction of the compressed soft tissue immediately above on the tissue engaging surface of the bone block. The rounded profile also greatly reduces stress concentrations and allows the soft tissue to distribute the compressive load more evenly across the entire cavity. As a result, the omega cavity gently grips the soft tissue without cutting, and prevents it from slipping, sliding or flowing in the direction it is being pulled or squeezed. Moreover, unlike the edges of teeth or ridges (see FIGS. 3A-3D) that concentrate force on a tissue at all times during compression, the edge of the omega cavity only exerts force when needed in response to the tissue therein being pulled or squeezed. In addition, the narrow mouth of the omega cavity (or channel) on the bone block surface provides an additional benefit by maximizing contact (and thus grip) between the soft tissue (e.g., tendon) and the tissue-engaging surface of the bone block.

Any layout of cavities and/or channels suitable for use with bone-tendon-bone grafts of the present invention, is also within the scope of this invention. Examples of bone blocks and bone segments suitable for use with the present invention can be found in commonly assigned U.S. patent applications Ser. No. 11/073,400, filed Mar. 4, 2005, now pending; U.S. Ser. No. 11/073,202, filed Mar. 4, 2005, now pending; U.S. Ser. No. 11/073,281, filed Mar. 4, 2005, now pending; and Ser. No. 11/313,280, filed Dec. 19, 2005, all of which are incorporated herein by reference. For example, a cavity can be a single hole in the surface of the bone segment with an omega shaped sidewall. Alternatively, a cavity can be a pocket or larger hole made by removing an area of material with an undercut around some or all of the periphery. When the cavity is a single channel or a plurality of channels, the channel(s) can run in the direction of pull of the tendon, or across the direction of pull of the tendon, or at an angle to the direction of pull of the tendon. In some embodiments of the present invention, the bone segment has two channels with an omega cross-section running in the direction of pull of the tendon. See, e.g., FIGS. 7A and 11A.

In other embodiments of the present invention, the layout of the channels can be such that the channels intersect or cross one another. In one embodiment, a series of channels can be used that criss-cross one another to produce a waffle-like pattern on the tendon engaging surface of a bone segment. In another embodiment, two channels can intersect one another to produce a "V" shaped layout on the tendon engaging face of a bone segment. This embodiment can also be thought of as a single channel that changes direction much like a bend in the road. It is within the scope of the present invention that the layout of channels include a single "V" shape, a plurality of "V" shapes, or some combination of different layouts. Other examples of layouts of the channels are "U" shaped, "W" shaped and "A" shaped. Alternative layouts for channels are graphic designs such as company insignia, random or psuedo-random designs such as a labyrinth or maze, or complex mathematically derived patterns such as fractal patterns.

A preferred layout for the channels is "Y" shaped. The "U" shaped layout includes a single "U" or 2-10 "Us," which may be stacked or overlapped. Typically, the U's in the layout are stacked top to bottom. In a preferred embodiment, a set of three "U" channels are stacked top to bottom. In an especially preferred embodiment, a bone segment has a layout on its tendon engaging face of three stacked "U" shaped channels where each channel has an omega-shaped cross-section. This channel arrangement of three stacked "U" shapes can also be interpreted as a double stacked "A" shape.

It is also within the scope of the present invention that one or both ends of a bone segment or bone block have the edge of the tendon engaging face reduced. Typically, this is performed by sanding, routing, grinding or cutting the edge to produce a round, beveled or chamfered edge. Preferably, this reduction of the end of the tendon engaging face results in an internal leading edge configuration that reduces tissue stresses during assembly and use. It is also within the scope of the present invention that the cross-sectional size of the cavities in any layout be the same or different. It is additionally within the scope of this invention for a bone segment or a bone block to have an overall lengthwise tapering profile.

In the present invention, a bone block assembly can comprises a combination of 2-10 bone segments. The 2-10 bone segments can be the same or different than the first bone segment. The 2-10 bone segments can have various configurations.

Embodiments of bone blocks or bone block assemblies of the present invention can be affixed to the end of a predetermined length of tendon by 1 to 30 biocompatible connectors that engage each of two opposing bone segments and the tendon that is sandwiched therebetween. The term "biocompatible connector" includes but is not limited to a pin, screw, suture, staple, rivet, strap, nail, band, adhesive, or chemical cross linker. Suitable biocompatible connectors include any connectors capable of holding the bone segments together as a unit (i.e., a bone block assembly). Some examples include pins that form an interference fit with holes machined in the bone blocks. Biocompatible connectors may be made from: metal (e.g., stainless steel, titanium), polymer, bone (e.g., cortical bone), or other biologics including connective tissues. Preferred bone pins are cortical bone pins (i.e., pins made from cortical bone).

It should be understood that when discussing sutures, adhesives, cross linkers, and other continuous or non-unitary biocompatible connectors, that a single application of the biocompatible connector type may contain multiple smaller units. For example, a single suture connection can be fabricated by stitching a plurality of sutures, e.g., 10 to 100 small individual sutures, and a single adhesive connection may be made by applying a plurality of drops of adhesive, e.g., 10 to 100 small individual drops of adhesive. A suitable biocompatible connector is a pin that is press fitted into a hole machined in the bone block. A typical pin is made from stainless steel, titanium, or cortical bone. A preferred pin is a cortical bone pin (i.e., a pin made from cortical bone). Interference fit cortical bone pins are preferred over the alternative biocompatible connector types listed above because they offer a strong and predictable fixation, are readily manufactured, incorporate and heal into the body, are simple to assemble, integrate easily into most graft designs and have minimal regulatory or safety risks.

It is desirable to have a tight and accurate interference fit between the pin(s) and the hole(s) in bone pieces that are connected by the pin(s). The target range for the pin in such an interference fit is 0.001 inches (0.0254 mm) to 0.003 inches (0.0762 mm) larger than the hole diameter, and is pressed fit into place. However, when the pin is made from cortical bone, it has been learned that freeze-drying the bone pins and other bone pieces exerts a disproportionate shrinkage upon the pins compared to the hole diameters. That is, the pin shrinks slightly more than the hole shrinks. Uncorrected, this would result in a less accurate, and less acceptable, interference fit.

The following method can solve this problem. A bone pin, preferably of cortical bone, of a desired diameter is vacuum dried for at least five hours. This drying is preferably at room temperature and at a negative pressure of approximately 100 milliTorre. This pre-treatment results in a shrinkage of approximately 80 percent of the total shrinkage that would occur in freeze drying. The pin diameter is measured, and a hole is made in the portions to be assembled using an appropriately sized drill bit. The target size for the hole is 0.002 inches (0.0508 mm) to 0.0025 inches (0.0635 mm) smaller than the post-vacuum-drying pin diameter. Preferably, prior to this drilling, the bone portions to be assembled have been kept saturated with moisture to maintain a consistent size and subsequent shrinkage percent. After all holes are drilled, the pin(s) are press fitted into the through holes, machined into a bone segment of the present invention (or into a second bone block), and then freeze dried. The resulting assembled allografts have been found to have interference fits in the desired target range. This method is applicable to the various embodiments described in this disclosure. Where the bone pins are not freeze dried, it is sufficient to dip them in alcohol to facilitate their insertion (press fitting).

Exterior Surfaces of Bone Segments and Bone Blocks

In preferred embodiments of bone blocks of the present invention, BTB grafts have a first bone block and a second bone block, where at least one of the bone blocks has an exterior surface having threads along at least a portion thereof. In some embodiments, the first bone block has an exterior surface having threads along at least a portion thereof, and the second bone block has an exterior surface that is substantially cylindrical, stepped, tapered, or otherwise configured to be fixed in a bone tunnel.

Threads on a bone block may be any configuration suitable for use in the intended application. For example, threads may be angled to either side, or may follow a normal (symmetrical) thread pattern. Various types of threads that may be suitable for use with the present technology are disclosed, for example, in the "Machinery's Handbook," 24th Edition, by Erik Oberg et al., pp. 1617-1657 (1992 Industrial Press Inc.), the disclosure of which is hereby incorporated by reference with respect to thread types. Types of thread profiles that may be useful with the present technology include, but are not limited to, symmetrical threads, ACME centralizing threads, stub threads, square threads, buttress threads, hose coupling threads, rolled threads, and pipe threads.

The thread major diameter, minor diameter (i.e., inner diameter or shaft diameter), pitch, and direction may be the same or different between two bone blocks on a single BTB graft. For example, a graft may be configured so that the angles of the threads (such as buttressed threads) is the same for both bone blocks of a BTB graft, or so that the angles of the threads on the first bone block opposes the angles of the threads on the second bone block. In such an embodiment, the threads would still preferably run in the same direction so that they could be simultaneously threaded into opposing bone tunnels by rotating an insertion tool. As another example, individual thread parameters may be selectively matched or varied along the individual bone block at either end of the graft or between the two bone blocks. A graft with the same pitch but varying diameter would allow the leading end of and ACL replacement graft to pass through the tibial tunnel with minimal contact before engaging a smaller hole in the femoral tunnel. Alternatively, the graft may have the same diameter on each bone block, or a larger diameter on the leading bone block and be configured for installation in retrograde (reverse rotation, or backing out of the threads) or for bidirectional implantation. A graft may also be configured with a slight variation in pitch between the two bone blocks, producing a change in tension during insertion, as one block advances slightly more than the other with each rotation.

By altering the thread geometry, the graft can be tuned to provide optimal holding power for a given surgical application. For example, smaller diameter, sharp-V or UN (symmetrical) profile threads of a fine pitch may be advantageous in anchoring the graft into the tibia of a relatively small patient such as a 5 foot tall, 17 year old high school soccer player. As another example, larger diameter, buttress (angled) profile threads of a coarse pitch may be advantageous in anchoring the graft into the femur of a relatively large patient such as a 7 foot tall, 25 year old professional basketball player.

Bone Block Assembly

Bone block assemblies are a subset of bone blocks, and are also referred to as assembled bone blocks. A bone block assembly is a particular type of bone block comprising two or more bone segments. In preferred embodiments, a bone block assembly comprises a first bone segment and a second bone segment that sandwich one end of a length of tendon therebetween in an assembled BTB graft.

In some embodiments, a bone block assembly is made by stacking a first bone segment into an assembly fixture with its tendon engaging surface facing upward, then placing an end of a tendon into the fixture on top of the tendon engaging face, followed by stacking a second bone segment into the fixture such that its tendon engaging face engages the tendon. The assembly fixture is then tightened or clamped to hold the pieces in register while the biocompatible connectors are installed. When the biocompatible connectors are pins, a drill is used to create holes through the assembly, then a reamer cleans and sizes the holes, and finally pins are pressed into the holes to hold the assembly together.

Treatment of Components

To be suitable for implantation in humans, the bone blocks and tendons (soft tissue) of the present invention must be treated to remove any antigenic proteins, which may generate a rejection of the implant. It also must be treated to remove any bacteria and viruses. The entire assembly can be treated through one or more cleaning or sterilization processes which produces an implantable graft without damaging the tissues in the graft. Alternatively, the components can be treated individually by an appropriate cleaning or sterilization process prior to assembly. In either case, the optional step of terminal sterilization is performed by methods known in the art such as gamma, e-beam, X-ray, or UV irradiation or by vapor phase hydrogen peroxide, or supercritical $CO_2$. Other optional steps include sterile packaging, and/or freezing or freeze drying.

Suitable processes for removing antigenic proteins and sterilizing to neutralize any bacteria and viruses are known in the art. See U.S. Pat. No. 5,846,484, entitled "Pressure flow system and method for treating a fluid permeable workpiece such as a bone," which issued to Scarborough, et al. on Dec. 8, 1998. In the present case, the applicants utilized the assignees' well known method for defatting tissue, which also has the added benefit of removing blood, cellular debris, and soluble and antigenic proteins, by subjecting the muscle tissue to alternating cycles of pressure and vacuum in the sequential presence of solvents, such as isopropyl alcohol, hydrogen peroxide and a detergent. These assignee's processes also neutralize any bacteria and viruses. These processes are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety.

An improved process for cleansing (treating) soft tissues (and bone) for implantation, while preserving the desirable traits of flexibility and strength in the soft tissue, is disclosed in commonly assigned U.S. patent application Ser. No. 10/828,653, entitled "Process and Apparatus for Treating Implants Comprising Soft Tissue," in the name of Mills et al., filed Apr. 20, 2004, which is hereby incorporated by reference for its disclosure on such process for cleansing.

BTB Graft and Implant Embodiments

Preferred self fixing bone-tendon-bone (BTB) grafts of the present invention comprise a length of tendon having a first opposing end and a second opposing end, wherein a first bone block is attached to the first opposing end of the tendon and a second bone block is attached to the second opposing end of said tendon. The bone blocks of these BTB grafts most preferably comprise one or two bone segments. Additionally, at least one bone block preferably has an exterior surface having threads along at least a portion thereof.

In one preferred embodiment, the first bone block and the second bone block each have an exterior surface having threads along at least a portion thereof, and the threads of each run in the same direction so that each bone block is implantable in a respective hole in opposing bones of a joint on a patient when the BTB is rotated as a whole in the threaded direction. In another preferred embodiment, threads on along at least a portion of the first bone block run in an opposing direction to threads along at least a portion of the second bone block. In other embodiments where both the first and second bone block have threads along at least a portion thereof, the threads on the first bone block can have a smaller outer diameter than the threads on the second bone block. The threads on a bone block can also have a diameter which varies along the length of the bone block.

In other embodiments, the first bone block has an exterior surface having threads along at least a portion thereof, and the second bone block has an exterior surface that is substantially cylindrical, stepped, or tapered.

In some embodiments of BT implants of the present invention, a single bone block is attached to one end of a tendon or tendon bundle, and the opposing end of the tendon or tendon bundle is left free and fixed by means known in the art, such as an endo-button, soft tissue interference screw, or cross pin fixation device. It is contemplated by the present invention that any features discussed with respect to a single bone block of any BTB embodiment my be applied to the single bone block of a BT embodiment, as well.

In some embodiments of BT implants of the present invention, the bone block preferably has an exterior surface having threads along at least a portion thereof. Alternatively, the bone block may have an exterior surface having grooves, notches, or protrusions along at least a portion thereof. In any of the BT embodiments of the present invention, the implant may optionally be mated with either a tensioner or an inserter, or both, specially adapted to accept the BT implant. In one such embodiment the tensioner and inserter are combined into a single device which simplifies surgical preparation, implantation, and fixation by maintaining tension and orientation of the implant during implantation and fixation.

In some embodiments of BTB implants of the present invention, the implant comprises a tensioner spanning the length of the tendon. The tensioner can be configured to exert a predetermined tension on the spanned tendon during implantation, and can also be configured to maintain tension in the tendon during processing of the graft. In embodiments of implants comprising a tensioner, the tensioner can be integrated with an inserter, and can be external to the inserter.

In some embodiments, tensioners comprise a pair of spacers positioned on opposing sides of said tendon. In other embodiments, tensioners comprise a single spacer having a slot along its length for encasing said tendon. It is contemplated that tensioners disclosed herein as two-member tensioners could be produced as a single piece with a flexible or removable hinge or brace connecting them together. It is further contemplated that each member may be made of two to twenty smaller pieces which are held together by the inserter tool or sutures or a combination of the two, such that removal of the inserter after implantation facilitates removal of the tensioner.

In some embodiments, tensioners are essentially rigid and thus impart a fixed displacement between the two bone blocks. This fixed displacement can then be matched to the fixed gage length of the tendon to produce the desired tension and graft positioning, post implantation. In other embodiments, tensioners are configured to act essential as springs of a given spring constant which may be linear or non-linear. The spring constant can be selected to produce a desired tension and orientation in the graft before during and after implantation (pre-operative, intra-operative, and post-operative tension). The tensioner and inserter may also be designed together to provide intra-operative control and manipulation of tension and orientation of the implant. For example, a tensioner may be constructed featuring a plurality of multiple degree of freedom (MDOF) joints which support tension in the tendon, while allowing rotation and flexion of the implant and tensioner. In one embodiment, such tensioner is supported by an inserter featuring flexible wires which are themselves in tension, thus maintaining the tensioner and implant in alignment with controlled tension on the tendon while the bone blocks are threaded into non-coaxial bone tunnels.

Tensioners may be crafted from metals, polymers, composite materials, or any other biocompatible material of sufficient strength and toughness to withstand the loads associated with manufacturing, preparing and implanting the graft. Biocompatible polymers are preferred for their ease of manufacture, cost, and functionality. Metals may be preferred for their high strength and machinability.

The outside surface of a tensioner can be threaded with threads running in the same direction as the threads on said first bone block or said second bone block. In some such embodiments, the threads on the surface of the tensioner are contiguous with the threads on one or both of the bone blocks.

In some embodiments, tensioners for use with the present invention bend, flex, or break away after implantation. This is advantageous because it allows for removal of tensioners post implantation through the arthroscopic access ports already in use for many surgical procedures. The separation of tensioners from implant may by initiated by removal of the inserter, through predisposition, biasing or spring-loading the tensioners then capturing the tensioners and constraining them in an otherwise unstable position by their interaction with the inserter. Alternatively, the tensioners may be designed to rest in place regardless of the presence of the inserter, and thus require a secondary motion such as the retraction of a pre-attached suture or manipulation with an instrument through and arthroscopic access port in order to release them from the graft.

In some embodiments, the insertion tool or inserter is formed as a continuous piece of metal. Metals such as stainless steel and titanium are widely known in the art as preferred materials for surgical instruments and inserters, due to their high strength and toughness. In other embodiments the inserter may be assembled and even modular, allowing for cleaning and sterilization between uses, and for the selection of specific components such as a shaped handle or a specific length shaft for each surgical procedure. In one preferred embodiment, the stainless steel shaft, handle and prongs of the inserter are press-fit or shrunk-fit together to form a rigid unitary inserter tool for maximum strength and rigidity. In an alternatively preferred embodiment, the prongs, shaft and handle are all separate pieces, allowing for some controlled motion between each piece, for example, squeezing the handle to pull tension back on the prongs and through the graft by pressing the graft and tensioner assembly between the prongs and the shaft of the inserter. In this embodiment, tension in the inserter components and graft assembly may be used to control distribution of forces and displacements including torsional loads experienced during threading of the graft into the bone tunnels.

Alternative acceptable materials for the inserter are widely known in the art, including polymers, ceramics and composite materials.

In preferred embodiments, BTB implants of the present invention are inserted into a patient using an insertion tool on which the BTB implant is mounted. In particularly preferred embodiments, a first bone block and a second bone block of a BTB graft, as well as a tensioner, can all be mounted on the insertion tool when the BTB implant is assembled. To facilitate this mounting, the first bone block and second bone block of a BTB graft preferably each have at least one hole, slot, or groove, (collectively "holes") therethrough, and the holes in the leading bone block assembly are aligned with the holes in the trailing bone block assembly for accommodating prongs of an insertion device. More preferably, the first and second bone blocks have 2 to 5 holes, slots or grooves that are aligned. In particularly preferred embodiments, the first bone block, the second bone block and the tensioner each preferably comprise at least one hole, slot, or groove in alignment for mounting on an insertion tool. More preferably, the first bone block, the second bone block and the tensioner each comprise from 2 to 5 holes, slots, or grooves in alignment. Suitable holes, slots, or grooves can have a circular or non-circular cross sectional profile.

Various embodiments of bone-tendon-bone grafts of the present invention, as well as the components thereof and tools for use therewith, are provided in the following discussion, which can be better understood by reference to the Figures.

FIGS. 1A-1B are views of one embodiment of an assembled self fixing assembled BTB of the present invention. FIG. 1A is a top view of one embodiment of a self fixing assembled BTB of the present invention, showing a first (leading) bone block 1, a length of tendon (e.g., tendon, ligament or fascia) 5 and a second (trailing) bone block 3. Bone blocks 1 and 3 are threaded on their exterior surface with buttressed threads 6 running in the same direction and having aligned angles. Bone block 1 has a leading end 7 that is optionally tapered to facilitate insertion and threading into a bone tunnel in the tibia and/or femur of a patient, typically a human patient. FIG. 1B is a cross sectional view of section BB of the self fixing assembled BTB from FIG. 1A. FIG. 1B shows the assembled nature of the BTB with bone block 1 having a first bone segment 1A and a second bone segment 1B sandwiching the first opposing end 5A of tendon 5. In a like manner, trailing bone block 3 has a third bone segment 3A and a fourth bone segment 3B sandwiching the second opposing end 5B of tendon 5. Bone segments 1B and 3B have a tendon engaging surface that is textured by rows of ridges that appear as teeth 2 that angle against the direction of pull of the tendon.

FIGS. 2A-2D are views of one embodiment of a first bone segment 1A of bone block 1 of FIG. 1. FIG. 2A is a perspective view of one embodiment of a first bone segment showing the leading end 7 of the bone segment 1A and its threaded exterior surface 28 characterized by threads 6, through holes 8B for alignment with the holes of a tailing bone block and ultimate placement on the prongs or pins of an insertion tool (see e.g., FIGS. 5A-5D). FIG. 2A also shows a pair of omega-shaped channels 29 on the tissue engaging surface. FIG. 2B is a side view of one embodiment of a first bone segment showing its threaded exterior surface with threads 6, having a height 26, an edge thickness 16 that defines the outer diameter OD, and an inner edge 14 that defines the inner diameter ID. On curved leading end 7, there is shown through hole 8 and omega-shaped channel 29. FIG. 2C is a top view looking through this embodiment of a first bone segment. The tissue (e.g., tendon) engaging surface has two substantially parallel omega-shaped channels 29. Also shown is leading end 7, lagging end 27, threads 6 having height 26, of pitch P and an edge 16. FIG. 2D is an end view of one embodiment of a first bone segment showing the lagging end wherein the omega-shaped channels 29 of the tissue engaging surface 4 are visible. Also visible are a pair of machined through holes 8B of a predetermined diameter for slideably engaging a corresponding pair of prongs or pins of an insertion tool.

Figure 3D:
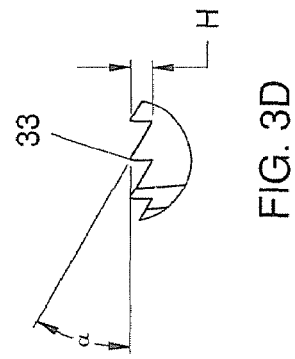
Figure 3E:
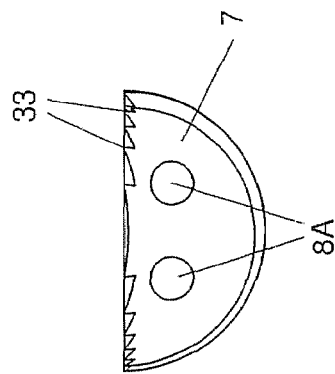
Figure 3C:
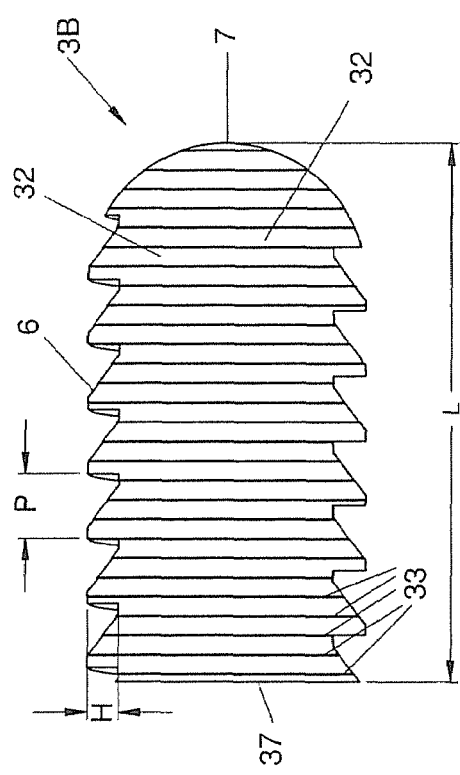
Figure 3B:
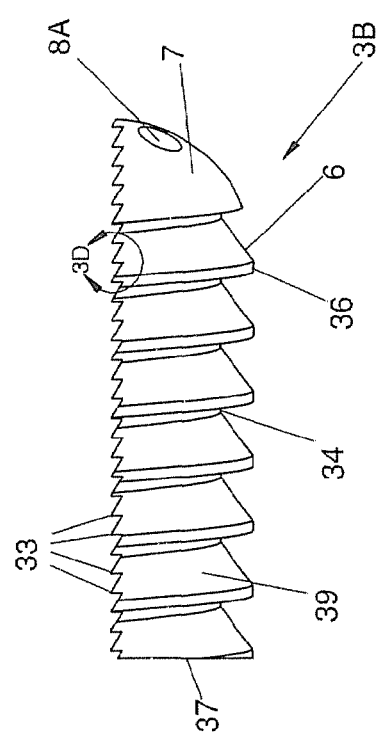

FIGS. 3A-3D are views of one embodiment of a bone segment 3B of a bone block 3 of FIG. 1. FIG. 3A is a perspective view of one embodiment of a bone segment 3B showing the leading end 7 of the bone segment, and its textured tissue (e.g., tendon) engaging surface 32. FIG. 3B is a side view of one embodiment of bone segment 3B showing its threaded exterior surface 39, and rows of ridges 33 angled against the direction of pull of the tendon. FIG. 3C is a bottom view of one embodiment of bone segment 3B showing the rows of angled ridges 33 on its tissue (tendon) engaging surface 32. FIG. 3D is a detail view of section 3D of FIG. 3B, showing the angled ridges having angle α and height H. FIG. 3E is and end view of one embodiment of bone segment 3B showing the leading end 7 having through holes 8A of a predetermined diameter for slideably engaging prongs or pins of an insertion tool and the ridges 33 texture of the tissue engaging surface are clearly visible.

FIGS. 4A-4D are views of one embodiment of a tendon tensioner for applying tension to the tendon in a self fixing assembled BTB of the present invention and for spacing the first and second bone blocks a predetermined distance from one another. FIG. 4A is a perspective view of one member 40 of a two member tendon tensioner showing its through holes 48 of a predetermined diameter for engaging the prongs of an insertion tool and a curved groove 42 for accommodating the tendon. The second member (not shown) can be the same or different and would be sutured to member 40 by a suture in its suture hole 41. FIG. 4B is a top view of tendon tensioner 40 having suture hole 41 and through holes 48. FIG. 4C is a side view of one member of the tensioner pair showing through holes 48 and suture hole 41. FIG. 4D is an end view of tensioner 40 looking down its through holes 48.

FIGS. 5A-5C are views of one embodiment of a hand operated insertion tool 50 for inserting (threading) the leading block of embodiments of a self fixing assembled BTB of the present invention into a tapped (threaded) hole in a femur and simultaneously inserting the trailing block into the tapped (threaded) bone tunnel in the tibia of the recipient patient. FIG. 5A is a perspective view of one embodiment of an insertion tool 50 having a shaft 51, a cross handle 52 and four prongs that correspond to the four holes shown in the embodiment the self fixing assembled BTB of FIGS. 1A-1B. The prongs are shown as pairs 58A and 58B. FIG. 5B is a bottom view of the insertion tool 50. FIG. 5C is a head on view of the pronged end of the insertion tool 50 showing that in this embodiment the 4 prongs are optionally two pairs 58A and 58B of prongs of different diameters which allow for a specific orientation of the self fixing assembled BTB on the implantation tool 50. FIG. 5D is a side view of the insertion tool 50, showing the two different sizes (diameters) of the prongs 58A and 58B.

FIG. 6A shows an exploded view of a BTB implant comprising a self fixing assembled BTB of FIGS. 1A-1B, a pair of tensioners of FIGS. 4A-4D, and the insertion tool of FIGS. 5A-5D. FIG. 6B shows the BTB implant comprising a self fixing assembled BTB of FIGS. 1A-1B with the tensioner of FIGS. 4A-4D in place, and the tensioned BTB slideably positioned on insertion tool 50 of FIGS. 5A-5D for insertion (threading) into appropriately drilled, and preferably tapped, holes in the tibia and femur of a patient in need of tendon replacement, repair or augmentation. As shown, one end of tendon 5 is sandwiched between the bone segments of leading bone block 1 and the other end is sandwiched between the bone segments of trailing bone block 3. Tensioner 40, comprising a pair of tensioner members, spans the length of the tendon 5 between the bone blocks, and is integrated with the insertion tool in that the prongs of the insertion tool are engaging the through holes of the tensioner.

FIGS. 7A-7D show a series of views of an embodiment of a bone segment that can be used with the present invention. FIG. 7A is a perspective view of the exterior surface of bone segment 70 showing its semi-capsular shape, which is rounded at both ends. Bone block 70 has a longitudinal groove 79 running its length. As shown, groove 79 is centered on the bone segment. In an alternate embodiment, the groove is positioned off center. Groove 79 has radius R, which is suitable for maximizing radial contact with an interference screw (not shown). Groove 79 also has two holes 72 positioned thereon and suitably sized for receiving an interference pin (not shown) which would hold bone segment 70 to a suitably sized opposing bone segment and a segment of soft tissue sandwiched therebetween. Bone segment 70 also has a pair of channels 77 with an omega shaped cross section running the length of its tissue engaging surface 71. FIG. 7B is a side view of the bone segment showing its semi-capsular shape and the positions of the holes 72 running through to tissue engaging surface 71. FIG. 7C is a bottom view of bone segment 70 showing the omega shaped channels 77 in the tissue engaging surface, and the two symmetrically placed pin holes 72. Each of the ends of the bone block have a second radius R2. As shown in FIG. 7D, the body of the bone block also has a radius R3. Different combinations of radius values for R, R2, and R3 will result in tangent, truncated, or sharp corner edge transitions between the end of the bone block and the body of the bone block, e.g., 7 mm diameter bone block with a 10 mm R will produce a sharp edge or corner between the body and the end, while a 10 mm diameter bone block with a 5 mm R will produce a tangent edge between the end of the bone block and the body of the bone block. FIG. 7D is an end view of the bone segment of FIG. 7A, showing the generally hemispherical shape of radius R3 interrupted by groove 79 having a radius R. Typically, a bone segment has 1 such groove for an interference screw, alternatively a bone segment can have 2 to 6 such grooves, resulting in final bone block assemblies with grooves to accommodate from 1 to 12 interference screws, preferably 1 to 6 interference screws, more preferably 2 to 4 interference screws. Grooves for interference screws have threads, tapped threads or no threads. In an alternate embodiment, a same or similar groove is included in the design to accommodate soft tissue that is external to the bone block assembly.

FIGS. 8A-8D show views of another embodiment of a bone segment 80 suitable for use with the present invention. Bone segment 80 is semi-capsule shaped bone segment. FIG. 8A is a perspective view of semi-capsule shaped bone segment 80, having holes 82 for receiving a biocompatible pin (not shown) that would hold this bone segment to any one of a variety of appropriately shaped opposing bone segments and to a segment of soft tissue sandwiched therebetween. Also shown on the exterior surface of this embodiment are ridges 89 suitable for gripping a bone tunnel and reducing slippage in the direction of pull (arrow) of the tendon. Ridges 89 can be described as crush ribs and are particularly useful for press fit fixation. FIG. 8C is a top view of the exterior surface of bone segment 80. In this figure, the hemispherical ends have radius R1, and the ridges project at an angle "C". The angle C preferably ranges from 1° to 60°. As shown in FIG. 8B, each of the ends of the bone segment have a second radius R2. As shown in FIG. 8D, the body of the bone segment has a radius R3. FIG. 8B is a side view of the bone segment 80 showing its semi-capsular shape and channel 87 running its length. FIG. 8D is an end view of the bone segment 80, showing the generally hemispherical shape of radius R3. A pair of channels 87 having an omega shaped cross section is shown on the tissue engaging surface 81.

FIGS. 9A-9D are views of another embodiment of a BTB graft of the present invention. FIG. 9A is an exploded perspective view of a preferred embodiment of an assembled BTB graft of the present invention. In this exploded perspective view, the BTB graft is composed of two assembled bone block assemblies, one on each of the opposing ends of a segment of soft tissue 93 of predetermined length. In FIG. 9A, each bone block-tendon assembly has at least one bone segment 91 of the present invention as a component thereof. Each of bone segments 91 are shown as having tendon engaging surface 91A with a stacked/overlapping triple "U" pattern of channels 97 thereon, each channel having the omega-shaped cross section. Bone segments 91 also have holes 92 for receiving interference pins 98. Bone segments 96 have a groove 98 of a predetermined radius for accommodating the curvature of an interference screw (not shown). FIG. 9B is a side view of the assembled BTB graft 90 wherein the bone segments 96 are shown as having a soft tissue engaging face 96A with teeth (actually rows of ridges) angled against the direction of pull of the tendon and engaging the soft tissue 93. FIG. 9C is a top view of the assembled BTB graft wherein one embodiment for positioning three bone pins 98 is shown. Additional holes 99 can be used to accommodate additional pins, or may be used for two pin placement instead of the currently shown three pin placement, or to accept suture during surgery for purposes of holding, guiding, or pulling graft into place in the bone tunnel and for tensioning the graft prior to and during fixation. Depressions 95 are useful as physical and visual placement aids during surgery, as they provide a visual marker for the surgeon to align fixations devices such as an interference screw, and they also provide a physical reference point and positive location and contact for instruments or guide wires to push or guide the graft into place. FIG. 9D is an end view of the assembled BTB graft showing the soft tissue sandwiched between opposing semi-capsular bone segments 91 and 96. In this view, the assembled BTB graft has the generally circular diameter of a bone tunnel into which it can be inserted during a surgical repair of a tendon in a patient in need of such a repair. In this view, the groove 98 is visible and would accommodate an interference screw (not shown) for locking that end of the BTB in its corresponding bone tunnel.

Figure 10D:
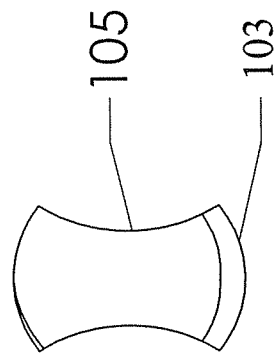
FIGS. 10A-10D provide views of one embodiment of a bone block comprising a top, a bottom, at least two lateral sides connecting said top and said bottom, and at least one portal through said bone block from said top side to said bottom side. This bone block may preferably be used as the leading bone block in a BTB graft such as that shown in FIGS. 1A-1B. This bone block may also be used as the trailing bone block in a BTB graft, or alternatively used as the sole bone block in a BT graft, such as in the case of a medial patellar femoral ligament reconstruction.
Figure 10A:
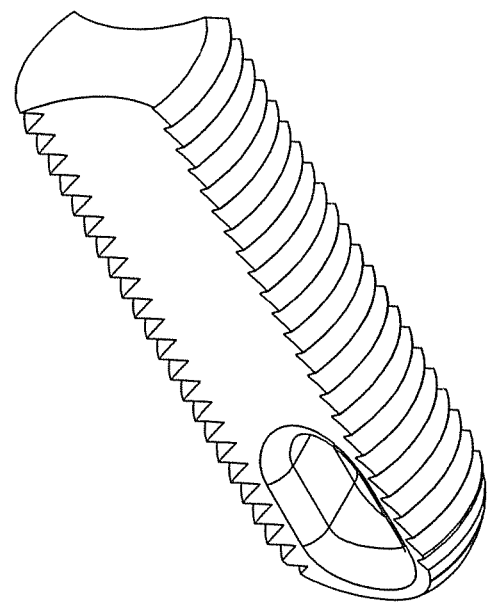
Figure 10B:
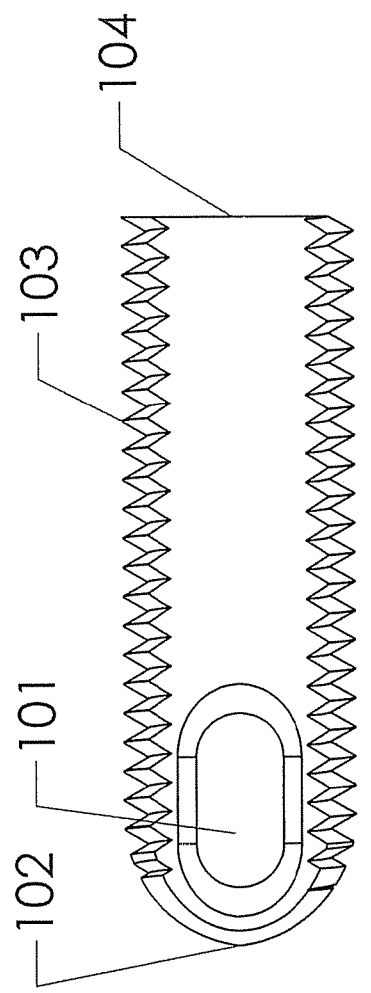
Figure 10C:
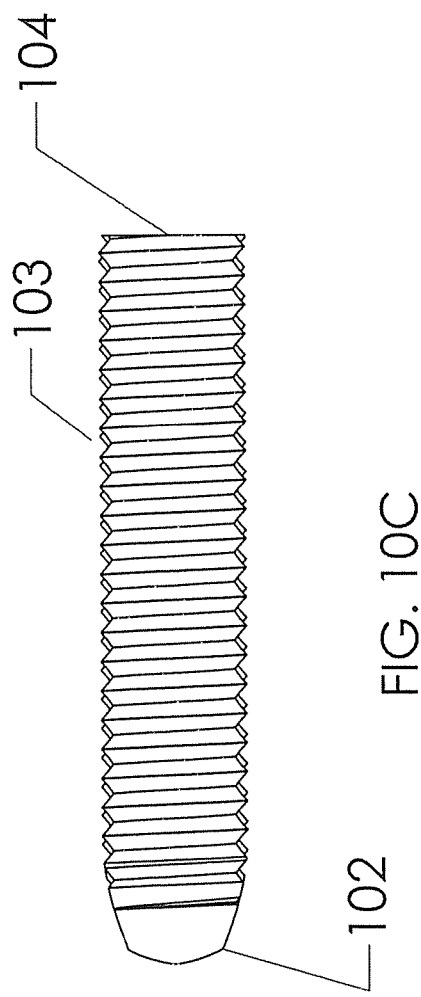

FIGS. 10A-10D provide views of one embodiment of bone segment comprising a top, a bottom, at least two lateral sides connecting said top and said bottom, and at least one portal through said bone segment from said top side to said bottom side. A bone segment of this type could be used with the present technology as a bone block on its own rather than in conjunction with another bone segment in forming a bone block. The illustrated bone segment comprises a leading end 102 and a lagging end 104 opposite the leading end. FIG. 10A is a perspective view of the bone segment. FIG. 10B is a top view, showing the bone segment having a portal 101 located in leading end 102. In this embodiment, the interior wall of portal 101 forms a closed loop within the bone segment, and leading end 102 is rounded to aid in insertion of the implant. In other embodiments, the interior wall of the portal is an open shape or a notch, which results in leasing end 102 having an open end rather than a closed rounded end as shown in FIGS. 10A-10D. In various embodiments the interior wall of the portal as viewed from the top side of the bone segment forms a shape selected from the group comprising an oval, a circle, a curved "U", a block "U", a rectangle, a "V", and a semi-circle. FIG. 10D is an end view of the bone block showing textured surface 103 and curved surfaces 105. Curved surfaces 105 are curved notches or grooves on the sides of the exterior surface for maximum engagement of interference screws. One similar embodiment has only one curved notch or groove, and another embodiment has none at all. Textured surfaces 103 can be threads, striations, or any other texture that would facilitate fixation of the bone segment at the surgical site.

FIGS. 11A-11D are views of one embodiment of a bone segment of the present invention. FIG. 11A is a perspective view of one embodiment of a bone segment showing the leading end 112 of the bone segment 111 and its threaded exterior surface characterized by threads 116, and through holes 118 for ultimate placement on the prongs or pins of an insertion tool. FIG. 11A also shows a pair of omega-shaped channels 119 on the tissue engaging surface 115. FIG. 11B is a side view of this embodiment of a bone segment showing its threaded exterior surface with threads 116 having an inner edge 114 that defines the inner diameter ID. On curved leading end 112, there is shown throughhole 118 and omega-shaped channel 119. FIG. 11C is a view looking through the threaded exterior surface of the bone segment. FIG. 11D is an end view showing the omega-shaped channels 119 of the tissue engaging surface. Also visible are the pair of through holes 118 of a predetermined diameter for slideably engaging a corresponding pair of prongs or pins of an insertion tool.

FIGS. 12A-12D are views of another embodiment of a bone segment for use with the present invention. FIG. 12A is a perspective view of one embodiment of a bone segment showing the threaded exterior surface 126. FIG. 12B is a side view this embodiment showing its symmetrically threaded exterior surface 126, and rows of ridges 123 angled against the direction of pull of the tendon. FIG. 120 is a bottom view of this embodiment of bone segment showing the rows of angled ridges 123 on the tissue (tendon) engaging surface 122. FIG. 12E is and end view of this embodiment of a bone segment showing through holes 128 of a predetermined diameter for slideably engaging prongs or pins of an insertion tool and the ridges 123 texture of the tissue engaging surface. FIG. 12D is a detail view of section D on FIG. 12B, showing the rows of angled ridges 123 on the tissue (tendon) engaging surface.

FIGS. 13A-13B are views of another embodiment of a self fixing assembled BTB of the present invention having aligned holes in the bone blocks to receive a pronged insertion tool. In this embodiment, the bone segments of FIGS. 11 and 12 have been combined to form both the first and second bone block assemblies. FIG. 13A is a top view of this embodiment of a self fixing assembled BTB of the present invention showing a first (leading) bone block 133, a length of tendon (e.g., tendon, ligament or fascia) 135 and a second (trailing) bone block 131. Bone blocks 131 and 133 have an overall bullet shaped configuration, which has a rounded leading end 138 and a substantially flat lagging end 137. Leading end 138 of bone block 133 is also optionally tapered to facilitate insertion and threading into a bone tunnel in the tibia and/or femur of a patient, typically a human patient. As shown, leading end 138 of each bone block has holes therein (two shown) in alignment between bone blocks 131 and 133 to receive a pronged insertion tool. Bone blocks 131 and 133 are also threaded on their exterior surface with symmetrical threads 136 running in the same direction. FIG. 13B is a cross sectional view of section BB of the self fixing assembled BTB from FIG. 13A. FIG. 13B shows the assembled nature of the BTB with bone block 133 having a first bone segment 133A and a second bone segment 133B sandwiching the first opposing end 135A of tendon 135. In a like manner, bone block 131 has a third bone segment 131A and a fourth bone segment 131B sandwiching the second opposing end 135B of tendon 135. Bone segments 131B and 133B have a tendon engaging surface that is textured by rows of ridges that appear as teeth 132 that angle against the direction of pull of the tendon.

FIGS. 14A-14B are views of another embodiment of a self fixing assembled BTB of the present invention. FIG. 14A is a top view of this embodiment of a self fixing assembled BTB of the present invention showing a first (leading) bone block 141, a length of tendon (e.g., tendon, ligament or fascia) 145 and a second (trailing) bone block 143. Bone blocks 141 and 143 have an overall bullet shaped configuration, which has a rounded leading end 147 and a substantially flat lagging end 148. Leading end 147 of bone block 141 is also optionally tapered to facilitate insertion and threading into a bone tunnel in the tibia and/or femur of a patient, typically a human patient. Bone blocks 141 and 143 are also threaded on their exterior surface with buttressed threads 146 running in the opposite direction and having opposing angles. FIG. 14B is a cross sectional view of section BB of the self fixing assembled BTB from FIG. 14A. FIG. 14B shows the assembled nature of the BTB with bone block 141 having a first bone segment 141A and a second bone segment 141B sandwiching the first opposing end 145A of tendon 145. In a like manner, bone block 143 has a third bone segment 143A and a fourth bone segment 143B sandwiching the second opposing end 145B of tendon 145. Bone segments 141B and 143B have a tendon engaging surface that is textured by rows of ridges that appear as teeth 142 that angle against the direction of pull of the tendon.

FIGS. 15A-15B are views of another embodiment of a self fixing assembled BTB of the present invention. FIG. 15A is a top view of this embodiment of a self fixing assembled BTB of the present invention showing a first (leading) bone block 151, a length of tendon (e.g., tendon, ligament or fascia) 155 and a second (trailing) bone block 153. Leading end 157 of bone block 151 is tapered, with a self centering protusion configured with one concave surface, one convex surface and a rounded lead-in to facilitate insertion, alignment and engagement of the threads leading into a bone tunnel in the tibia and/or femur of a patient, typically a human patient. Leading end 159 of bone block 153 is shown as being rounded. Lagging ends 158 of each bone block are shown as being substantially flat. Bone blocks 151 and 153 are also threaded on their exterior surface with buttressed threads 156 running in the opposite direction and having opposing angles. FIG. 15B is a cross sectional view of section BB of the self fixing assembled BTB from FIG. 15A. FIG. 15B shows the assembled nature of the BTB with bone block 151 having a first bone segment 151A and a second bone segment 151B sandwiching the first opposing end 155A of tendon 155. In a like manner, bone block 153 has a third bone segment 153A and a fourth bone segment 153B sandwiching the second opposing end 155B of tendon 155. Bone segments 151B and 153B have a tendon engaging surface that is textured by rows of ridges that appear as teeth 152 that angle against the direction of pull of the tendon.

FIGS. 16A-16B are views of a particularly preferred embodiment of a self fixing assembled BTB of the present invention. FIG. 16A is a top view of this embodiment of a self fixing assembled BTB of the present invention showing a first (leading) bone block 161, a length of tendon (e.g., tendon, ligament or fascia) 165 and a second (trailing) bone block 163. Bone blocks 161 and 163 are have an overall bullet shaped configuration, which has a rounded leading end 167 and a substantially flat lagging end 168. Bone block 161 as shown has an outer diameter that is smaller than the outer diameter of bone block 163. Leading end 167 of bone block 161 can also be optionally tapered to facilitate insertion and threading into a bone tunnel in the tibia and/or femur of a patient, typically a human patient. Bone blocks 161 and 163 are also threaded on their exterior surface with buttressed threads 166 running in the opposite direction and having opposing angles. The smaller diameter of leading bone block 161 enables it to pass through the larger first bone tunnel (e.g., the tibial tunnel in an ACL replacement procedure) without engaging the threaded surface of that tunnel. This is particularly advantageous when the threads are configured to run in opposite directions and with opposing angles in the case of a buttressed thread as shown. The resulting implant cleanly mates with buttressed threads opposing the direction of pull of the tendon at each end, producing an optimal result for resisting pullout or slippage of the bone blocks in the tunnels following surgery and during early aggressive rehabilitation. FIG. 16B is a cross sectional view of section BB of the self fixing assembled BTB from FIG. 16A. FIG. 16B shows the assembled nature of the BTB with bone block 161 having a first bone segment 161A and a second bone segment 161B sandwiching the first opposing end 165A of tendon 165. In a like manner, bone block 163 has a third bone segment 163A and a fourth bone segment 163B sandwiching the second opposing end 165B of tendon 165. Bone segments 161B and 163B have a tendon engaging surface that is textured by rows of ridges that appear as teeth 162 that angle against the direction of pull of the tendon.

FIGS. 17A-17B are views of another embodiment of a self fixing assembled BTB of the present invention having aligned internal slotted grooves 178 in the bone blocks to receive an insertion tool. The internal slotted grooves 178 have a rounded-end rectangular profile. FIG. 17A is a top view of this embodiment of a self fixing assembled BTB of the present invention showing a first (leading) bone block 173, a length of tendon (e.g., tendon, ligament or fascia) 175 and a second (trailing) bone block 171. Bone blocks 173 and 171 have an overall bullet shaped configuration, which has a rounded leading end 177. Leading end 177 of bone block 173 can also be optionally tapered to facilitate insertion and threading into a bone tunnel in the tibia and/or femur of a patient, typically a human patient. As shown, leading end 177 of each bone block has internal slotted grooves 178 therein. Bone blocks 171 and 173 are also threaded on their exterior surface with buttressed threads 176 running in the same direction. FIG. 17B is a cross sectional view of section BB of the self fixing assembled BTB from FIG. 17A. FIG. 17B shows the assembled nature of the BTB with bone block 173 having a first bone segment 173A and a second bone segment 173B sandwiching the first opposing end 175A of tendon 175. In a like manner, bone block 171 has a third bone segment 171A and a fourth bone segment 171B sandwiching the second opposing end 175B of tendon 175. Bone segments 171B and 173B have a tendon engaging surface that is textured by rows of ridges that appear as teeth 172 that angle against the direction of pull of the tendon. The cross-sectional view of internal slotted grooves 178 shows that the slots go through the bone blocks, and are in alignment between bone blocks 171 and 173 to receive an insertion tool.

Figure 18A:
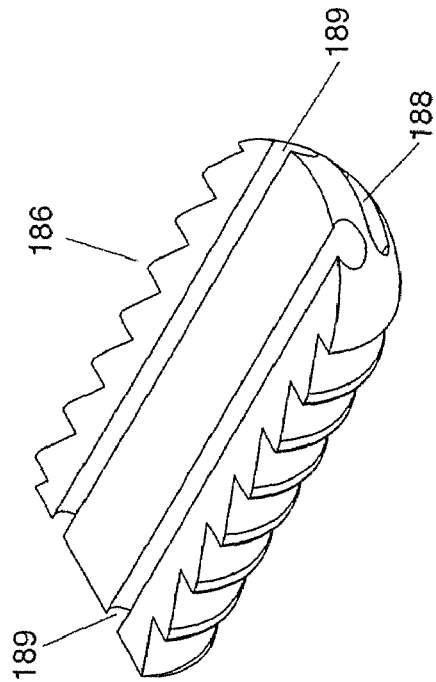
FIGS. 18A-18D are views of one embodiment of a first bone segment of a bone block of FIG. 17.
Figure 18D:
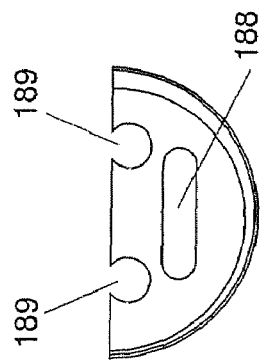
Figure 18C:
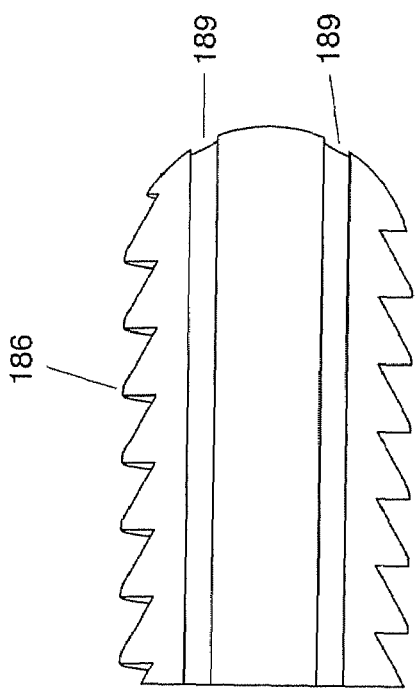
Figure 18B:
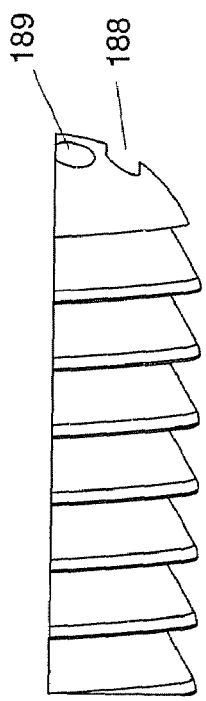

FIGS. 18A-18D are views of one embodiment of a bone segment having an internal slotted groove 188. This embodiment can be used, for example, in the BTB graft of FIGS. 17A-17B. FIG. 18A is a perspective view of one embodiment of a bone segment showing the threaded exterior surface characterized by threads 186, internal slotted groove 188 for slidably receiving an insertion tool, and omega shaped substantially parallel channels 189 on the tissue engaging surface of the bone segment. FIG. 18B is a side view of this embodiment of a bone segment showing its threaded exterior surface with threads 186. On the curved leading end, there is shown internal slotted groove 188 and omega-shaped channel 189. FIG. 18C is a bottom view showing the substantially parallel omega shaped channels 189 in the tissue engaging surface. FIG. 18D is an end view showing the omega-shaped channels 189 of the tissue engaging surface and the internal slotted groove 188 for slideably engaging a prong, or a pair of prongs or pins, of an insertion tool. In this embodiment, internal slotted groove 188 has a rounded-end rectangular profile.

Figure 19A:
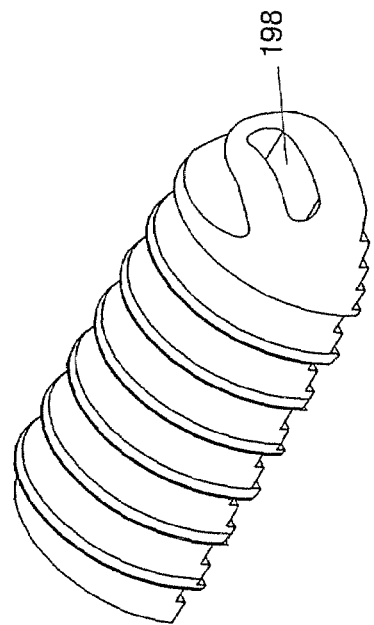
FIGS. 19A-19E are views of one embodiment of a second bone segment of a bone block of FIG. 17.
Figure 19C:
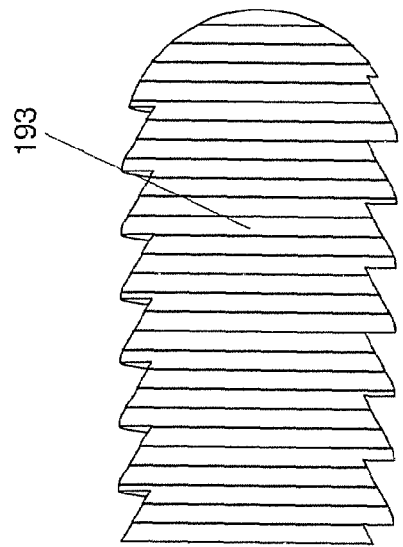
Figure 19B:
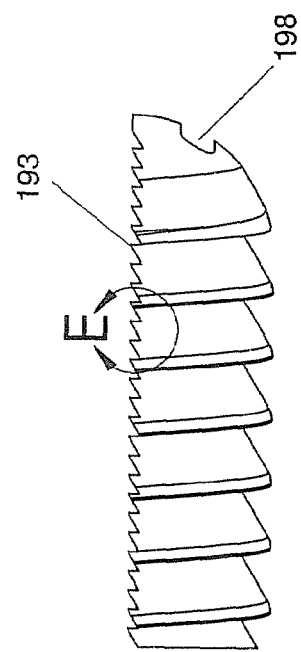
Figure 19D:
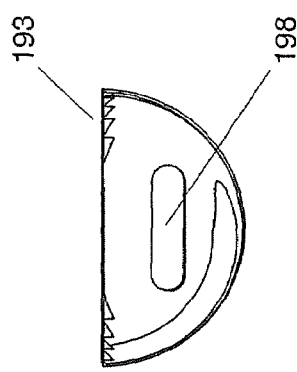
Figure 19E:
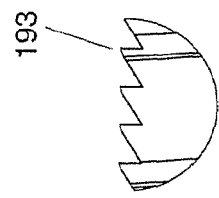

FIGS. 19A-19D are views of one embodiment of a bone segment with a textured tissue engaging surface, and having an internal slotted groove 198. This embodiment can be used, for example, in the BTB graft of FIGS. 17A-17B. In a preferred embodiment, the bone segment of FIGS. 19A-19D would be used with the bone segment of FIGS. 18A-18D, with the end of a tendon sandwiched therebetween, as a leading and/or trailing bone block of a BTB graft. FIG. 19A is a perspective view of one embodiment of a bone segment having internal slotted groove 198, and threads on the exterior surface of the bone segment. FIG. 19B is a side view of the bone segment showing its threaded exterior surface, and rows of ridges 193 on the tissue engaging surface, wherein the ridges are angled against the direction of pull of the tendon. FIG. 19C is a bottom view of the bone segment showing the rows of angled ridges 193 on its tissue (tendon) engaging surface. FIG. 19D is and end view of the bone segment showing internal slotted groove 198 for slideably engaging prongs or pins of an insertion tool, and the ridges 193 of the textured tissue engaging surface. The embodiment of the internal slotted groove shown has a rounded-end rectangular profile. FIG. 19E is a detail blow up of Section E of FIG. 19B, showing the ridges 193 of the textured tissue engaging surface.

Figure 20A:
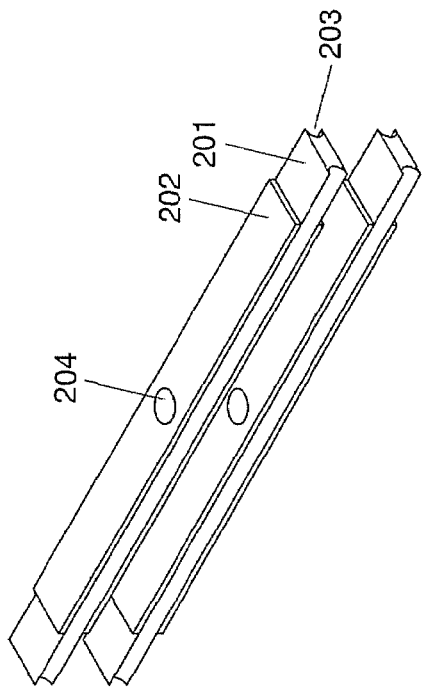
FIGS. 20A-20D are views of one embodiment of a tendon tensioner for spacing opposing assembled bone blocks and applying tension to the tendon in embodiments of self fixing assembled BTBs of the present invention.
Figure 20D:
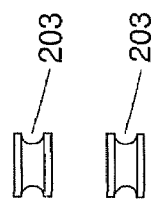
Figure 20C:
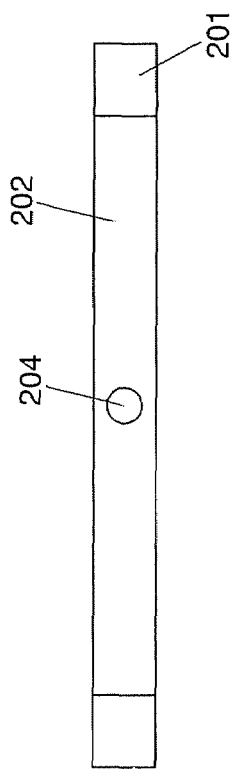
Figure 20B:
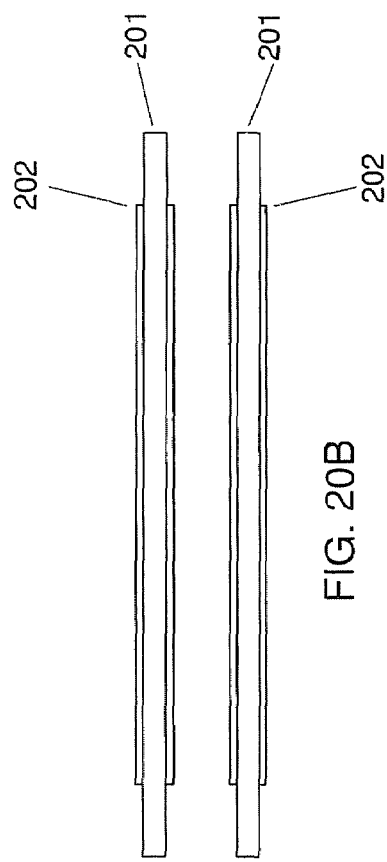

FIGS. 20A-20D are views of one embodiment of a tendon tensioner for applying tension to the tendon in the self fixing assembled BTB of the present invention and for spacing the first and second bone blocks a predetermined distance from one another. FIG. 20A is a perspective view of a pair of members that make up a two-member tendon tensioner. Curved grooves 203 are shown along the length of the tensioner members for engaging the prongs of an insertion tool. The tendon would be placed in between the two members along their length. As shown, the two members have the same configuration. Protrusions 201 may be adapted to mate with a corresponding recess, slot or other geometric feature of the bone blocks. Thickened portions 202 are configured to bear against the face of the bone blocks to carry the tension load and to help distribute torsional loads during insertion and rotation of the implant. In this embodiment, the two members may optionally be sutured together, with the tendon therebetween, by a suture in suture holes 204. FIG. 20C is a top view of one member of the pair, having suture hole 204. FIG. 20B is a side view of the tensioner pair. FIG. 20D is an end view of tensioner pair, showing curved grooves 203.

Figure 21A:
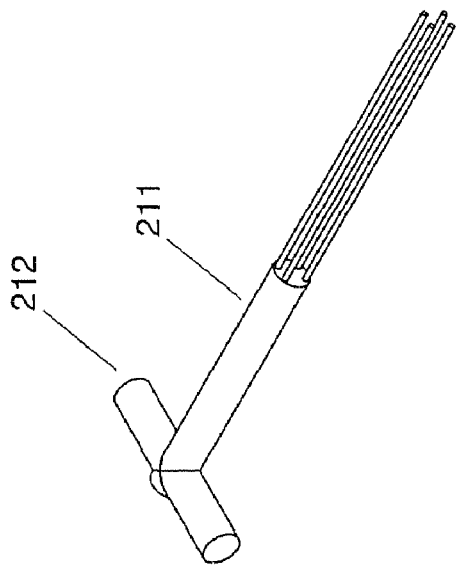
FIGS. 21A-21D are views of one embodiment of a hand operated insertion tool for simultaneously inserting the leading block of a self fixing assembled BTB of the present invention into a bone tunnel in a femur and the trailing block into a bone tunnel in the tibia of the recipient patient.
Figure 21C:
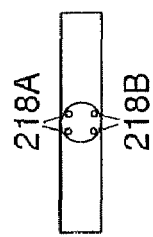
Figure 21D:
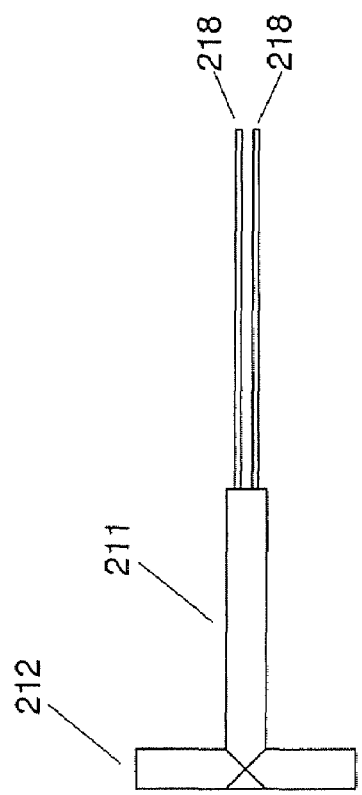
Figure 21B:
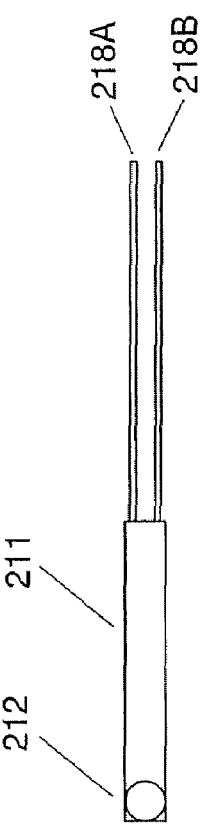

FIGS. 21A-21C are views of one embodiment of a hand operated insertion tool for inserting (threading) the leading block of the self fixing assembled BTB of the present invention into a tapped (threaded) hole in a femur and simultaneously inserting the trailing block into the tapped (threaded) bone tunnel in the tibia of the recipient patient. FIG. 21A is a perspective view of one embodiment of an insertion tool having a shaft 211, a cross handle 212 and four prongs. The four prongs can correspond to the four holes shown in the embodiment the self fixing assembled BTB of FIGS. 1A-1B when the corresponding holes in all of the bone segments are the same diameter. The prongs can also correspond to the rounded ends of the rounded-end rectangular internal slotted grooves of FIGS. 17A-17B. When additionally used with the tensioner of FIGS. 20A-20D, the prongs 218 of the insertion tool would engage the curved grooves 203 of FIG. 20A along the length of the tensioner members. FIGS. 21B and 21D are top and side views of the insertion tool. FIG. 21C is a head on view of the pronged end of the insertion tool showing that in this embodiment the 4 prongs have the same diameter.

FIG. 22A shows a BTB implant comprising a self fixing assembled BTB graft of FIGS. 17A-17B with the tensioner of FIGS. 20A-20D in place, and the tensioned BTB graft slideably positioned on insertion tool of FIGS. 21A-21D for insertion (threading) into appropriately drilled, and preferably tapped, holes in the tibia and femur of a patient in need of tendon replacement, repair or augmentation. As shown, one end of tendon 225 is sandwiched between the bone segments of leading bone block 223 and the other end is sandwiched between the bone segments of trailing bone block 224. Leading bone block 223 and trailing bone block 224 have a tensioner comprising a pair of tensioner members 226 spanning the length of the tendon 225 between the bone blocks. The lagging end of trailing bone block 224 is near or abuts shaft 221 of the insertion tool. FIG. 22B shows an exploded view of the BTB implant comprising a self fixing assembled BTB graft of FIGS. 17A-17B, a pair of tensioners of FIGS. 20A-20D, and the insertion tool of FIGS. 21A-21D.

FIGS. 23A-23B are views of another embodiment of a self fixing assembled BTB of the present invention having aligned internal slotted grooves 238 in the bone blocks to receive an insertion tool. The internal slotted grooves 238 have a curved profile. FIG. 23A is a top view of this embodiment of a self fixing assembled BTB of the present invention showing a first (leading) bone block 233, a length of tendon (e.g., tendon, ligament or fascia) 235 and a second (trailing) bone block 231. Bone blocks 233 and 231 have an overall bullet shaped configuration, which has a rounded leading end 237. Leading end 237 of bone block 233 can also be optionally tapered to facilitate insertion and threading into a bone tunnel in the tibia and/or femur of a patient, typically a human patient. As shown, leading end 237 of each bone block has internal slotted groove 238 therein. Bone blocks 231 and 233 are also threaded on their exterior surface with buttressed threads 236 running in the same direction. FIG. 23B is a cross sectional view of section AA of the self fixing assembled BTB from FIG. 23A. FIG. 23B shows the assembled nature of the BTB with bone block 233 having a first bone segment 233A and a second bone segment 233B sandwiching the first opposing end 235A of tendon 235. In a like manner, bone block 231 has a third bone segment 231A and a fourth bone segment 231B sandwiching the second opposing end 235B of tendon 235. Bone segments 231B and 233B have a tendon engaging surface that is textured by rows of ridges that appear as teeth 232 that angle against the direction of pull of the tendon. The cross-sectional view of internal slotted grooves 238 shows that the slotted grooves go through the bone blocks, and are in alignment between bone blocks 231 and 233 to receive an insertion tool.

Figure 24A:
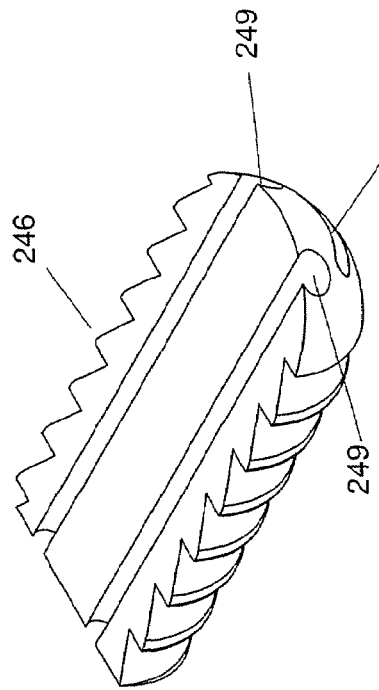
FIGS. 24A-24D are views of one embodiment of a first bone segment of a bone block of FIG. 23.
Figure 24D:
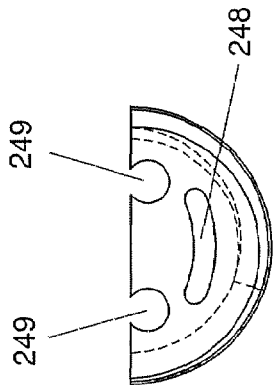
Figure 24C:
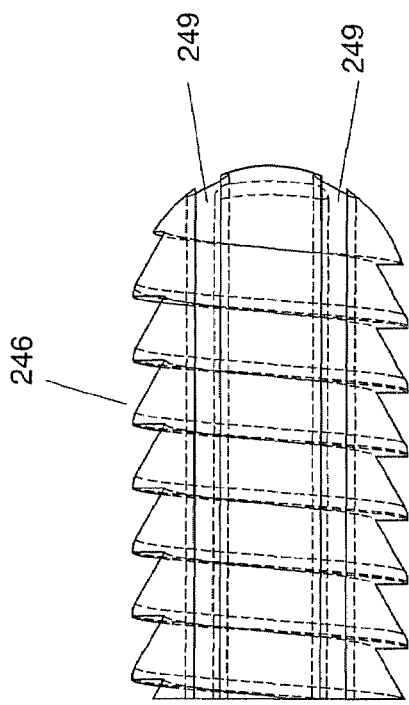
Figure 24B:
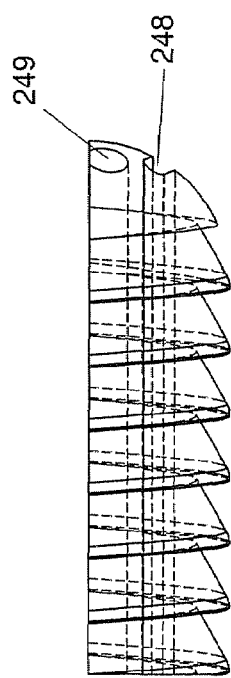

FIGS. 24A-24D are views of one embodiment of a bone segment having an internal slotted groove 248. This embodiment can be used, for example in the BTB graft of FIGS. 23A-23B. FIG. 24A is a perspective view of one embodiment of a bone segment showing the threaded exterior surface characterized by threads 246, internal slotted groove 248 for slidably receiving an insertion tool, and omega shaped substantially parallel channels 249 on the tissue engaging surface of the bone segment. FIG. 24B is a side view of this embodiment of a bone segment showing its threaded exterior surface with threads 246. On the curved leading end, there is shown internal slotted groove 248 and omega-shaped channel 249. FIG. 24C is a view looking through the bone segment, showing threads 246 on the exterior surface, and the substantially parallel omega shaped channels 249 in the tissue engaging surface. FIG. 24D is an end view showing the omega-shaped channels 249 of the tissue engaging surface and the internal slotted groove 248 for slideably engaging an insertion tool. In this embodiment, internal slotted groove 248 has a curved profile.

Figure 25A:
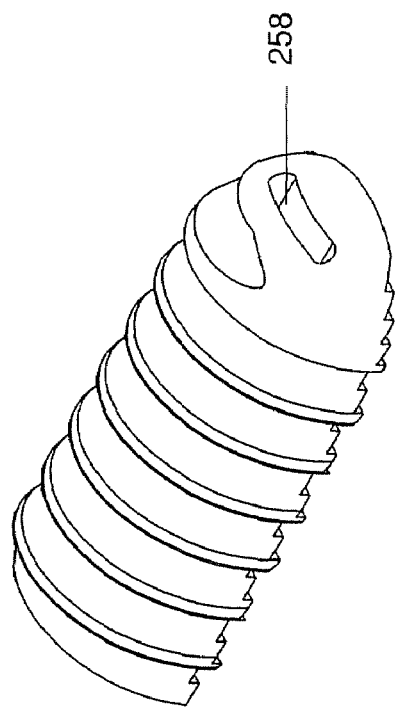
FIGS. 25A-25E are views of one embodiment of a second bone segment of a bone block of FIG. 23.
Figure 25C:
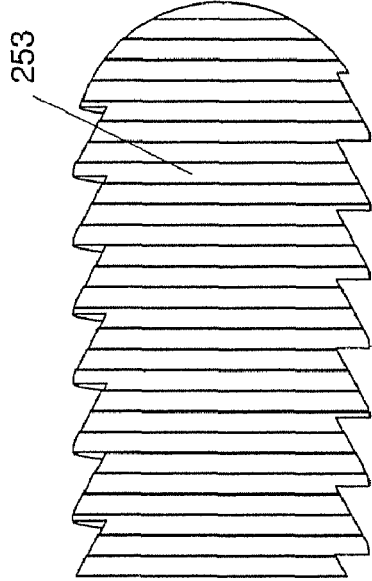
Figure 25E:
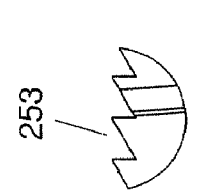
Figure 25D:
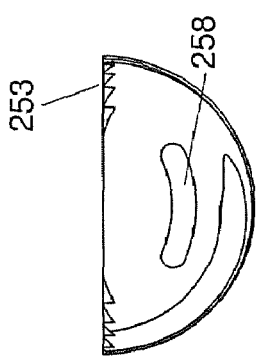
Figure 25B:
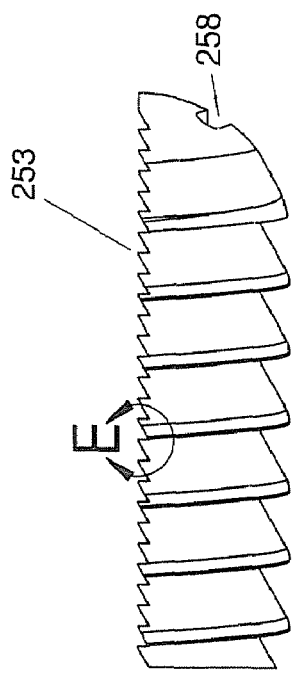

FIGS. 25A-25D are views of one embodiment of a bone segment with a textured tissue engaging surface, and having an internal slotted groove 258. This embodiment can be used, for example, in the BTB graft of FIGS. 23A-23B. In a preferred embodiment, the bone segment of FIGS. 25A-25D would be used with the bone segment of FIGS. 24A-24D, with the end of a tendon sandwiched therebetween, as a leading and/or trailing bone block of a BTB graft. FIG. 25A is a perspective view of one embodiment of a bone segment having internal slotted groove 258, and threads on the exterior surface of the bone segment. FIG. 25B is a side view of the bone segment showing its threaded exterior surface, and rows of ridges 253 on the tissue engaging surface, wherein the ridges are angled against the direction of pull of the tendon. FIG. 25C is a bottom view of the bone segment showing the rows of angled ridges 253 on its tissue (tendon) engaging surface. FIG. 25D is and end view of the bone segment showing internal slotted groove 258 for slideably engaging prongs or pins of an insertion tool, and the ridges 253 of the textured tissue engaging surface. In this embodiment, the internal slotted groove shown has a curved profile. FIG. 25E is a detail blow up of Section E of FIG. 25B, showing the ridges 253 of the textured tissue engaging surface.

Figure 26D:
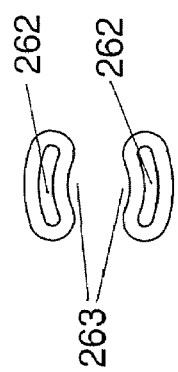
FIGS. 26A-26D are views of one embodiment of a tendon tensioner for spacing opposing assembled bone blocks and applying tension to the tendon in embodiments of self fixing assembled BTB grafts such as those of FIG. 23.
Figure 26A:
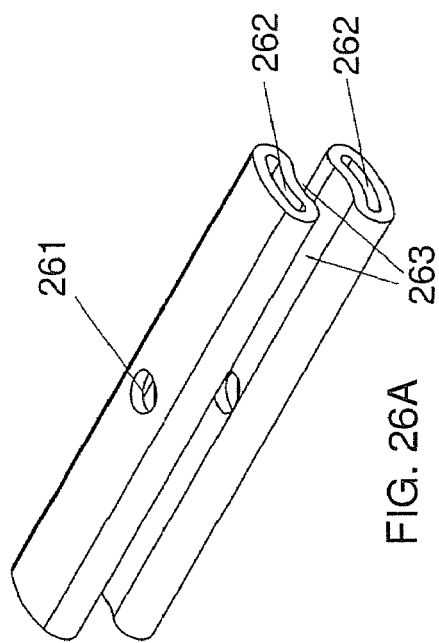
Figure 26C:
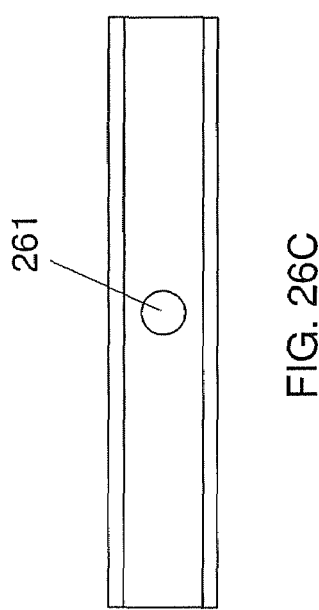
Figure 26B:
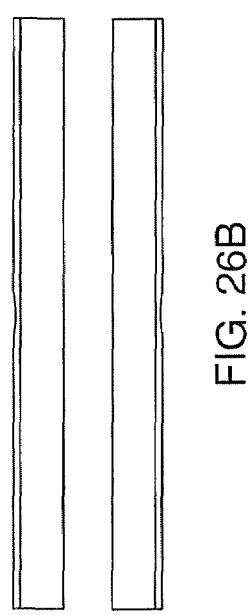

FIGS. 26A-26D are views of one embodiment of a tendon tensioner for applying tension to the tendon in a self fixing assembled BTB of the present invention and for spacing the first and second bone blocks a predetermined distance from one another. FIG. 26A is a perspective view of a pair of members of a two member tendon tensioner, showing internal slotted grooves 262 for engaging the prongs of an insertion tool and external curved grooves 263 for accommodating the tendon. The two members may optionally be sutured to each other by a suture in suture holes 261 to aid in maintaining positioning of the tensioner during implantation. Also optionally, suture or an instrument may be attached to suture holes 261 to aid in removal of the tensioner following insertion. FIG. 26B is a side view of tendon tensioner members. FIG. 26C is a top view of one member of the tensioner pair showing suture hole 261. FIG. 26D is an end view of tensioner 260 looking down its internal slotted grooves 262, which interface with the prongs of an inserter to share structural support and loading in minimal space. As shown, the two members are the same, and are oriented so that their external grooves face each other to engage either side of the tendon (not shown). This embodiment is advantageous in that the tensioner wraps around the tendon, protecting it and also offering maximum lateral and torsional stability while still fitting through the bone tunnels. The two members could also be of differing cross section, thickness or width and may be configured to differing orientations, as well as non-uniform or asymmetric distribution around the graft. It is also contemplated that the two members shown, or any tensioner disclosed herein, could be produced as a single piece with a flexible or removable hinge or brace connecting them together. It is further contemplated that each member may be made of two to twenty smaller pieces which are held together by the inserter tool or sutures or a combination of the two, such that removal of the inserter after implantation facilitates removal of the tensioner.

Figure 27A:
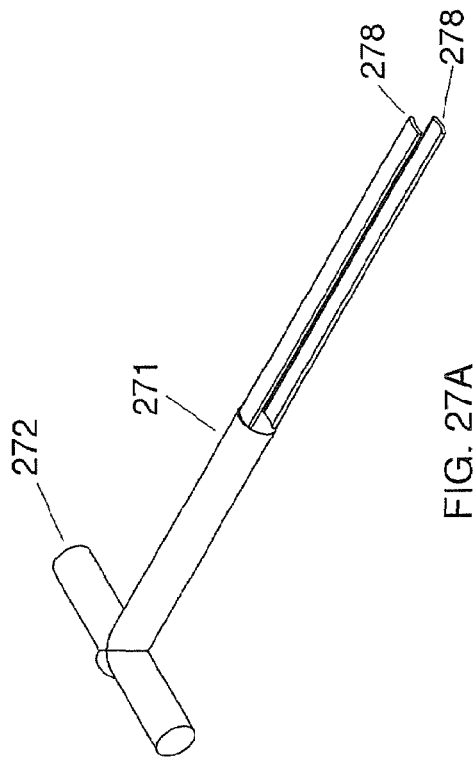
FIGS. 27A-27D are views of one embodiment of a hand operated insertion tool for simultaneously inserting the leading block of a self fixing assembled BTB of the present invention into a bone tunnel in a femur and the trailing block into a bone tunnel in the tibia of the recipient patient.
Figure 27C:
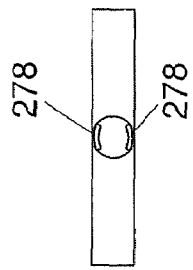
Figure 27D:
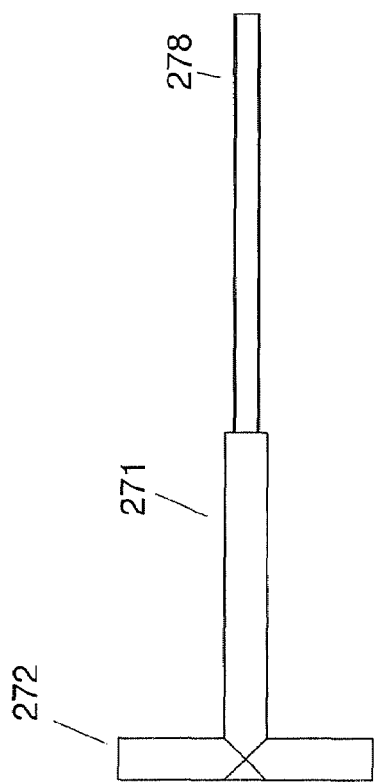
Figure 27B:
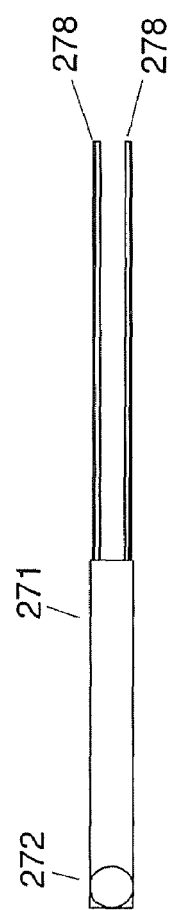

FIGS. 27A-27D are views of one embodiment of a hand operated insertion tool for inserting (threading) the leading block of the self fixing assembled BTB of the present invention into a tapped (threaded) hole in a femur and simultaneously inserting the trailing block into the tapped (threaded) bone tunnel in the tibia of the recipient patient. FIG. 27A is a perspective view of one embodiment of an insertion tool having a shaft 271, a cross handle 272 and two prongs having a curved profile. The curved profile of the prongs corresponds to the aligned internal slotted grooves of the BTB graft of FIGS. 23A-23B and the internal slotted grooves of the tensioner shown in FIGS. 26A-D. FIGS. 27B and 27D are top and side views of the insertion tool. FIG. 27C is a head on view of the pronged end of the insertion tool showing the curved profile of the prongs.

FIG. 28A shows a BTB implant comprising a self fixing assembled BTB graft of FIGS. 23A-23B with the tensioner of FIGS. 26A-26D in place, and the tensioned BTB graft slideably positioned on insertion tool of FIGS. 27A-27D for insertion (threading) into appropriately drilled, and preferably tapped, holes in the tibia and femur of a patient in need of tendon replacement, repair or augmentation. As shown, one end of tendon 285 is sandwiched between the bone segments of leading bone block 283 and the other end is sandwiched between the bone segments of trailing bone block 284. Leading bone block 283 and trailing bone block 284 have a tensioner comprising a pair of tensioner members 286 spanning the length of the tendon 285 between the bone blocks. The lagging end of trailing bone block 284 is near or abuts shaft 281 of the insertion tool. FIG. 28B shows an exploded view of the BTB implant comprising a self fixing assembled BTB graft of FIGS. 23A-23B, a pair of tensioners of FIGS. 26A-26D, and the insertion tool of FIGS. 27A-27D.

FIGS. 29A-29B are views of another embodiment of a self fixing assembled BTB of the present invention having aligned external slotted inserter grooves 298 in the bone blocks to receive an insertion tool. The external slotted inserter grooves 298 have a rectangular profile. FIG. 29A is a top view of this embodiment of a self fixing assembled BTB of the present invention showing a first (leading) bone block 293, a length of tendon (e.g., tendon, ligament or fascia) 295 and a second (trailing) bone block 291. Bone blocks 293 and 291 have an overall bullet shaped configuration, which has a rounded leading end 297. Leading end 297 of bone block 293 can also be optionally tapered to facilitate insertion and threading into a bone tunnel in the tibia and/or femur of a patient, typically a human patient. As shown, bone blocks 291 and 293 each have an external slotted inserter groove 298 in the exterior surface thereof. Bone blocks 291 and 293 are also threaded on their exterior surface with buttressed threads 296 running in the same direction. FIG. 29B is a cross sectional view of section AA of the self fixing assembled BTB from FIG. 29A. FIG. 29B shows the assembled nature of the BTB with bone block 293 having a first bone segment 293A and a second bone segment 293B sandwiching the first opposing end 295A of tendon 295. In a like manner, bone block 291 has a third bone segment 291A and a fourth bone segment 291B sandwiching the second opposing end 295B of tendon 295. Bone segments 291B and 293B have a tendon engaging surface that is textured by rows of ridges that appear as teeth 292 that angle against the direction of pull of the tendon.

Figure 30A:
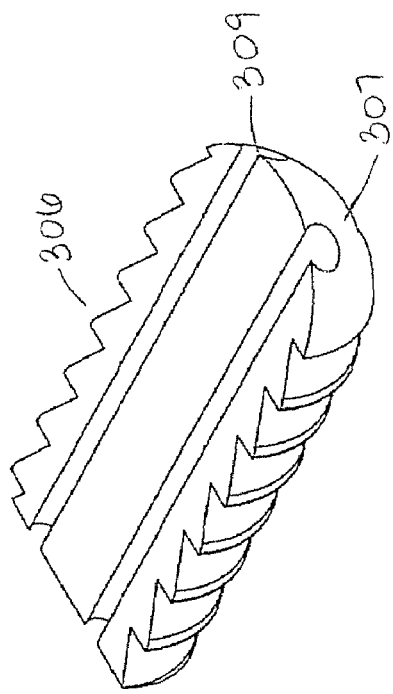
FIGS. 30A-30D are views of one embodiment of a first bone segment of a bone block of FIG. 29.
Figure 30D:
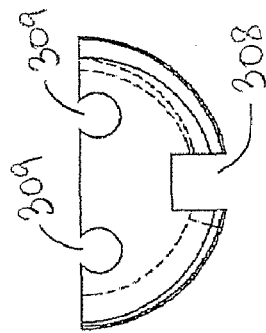
Figure 30C:
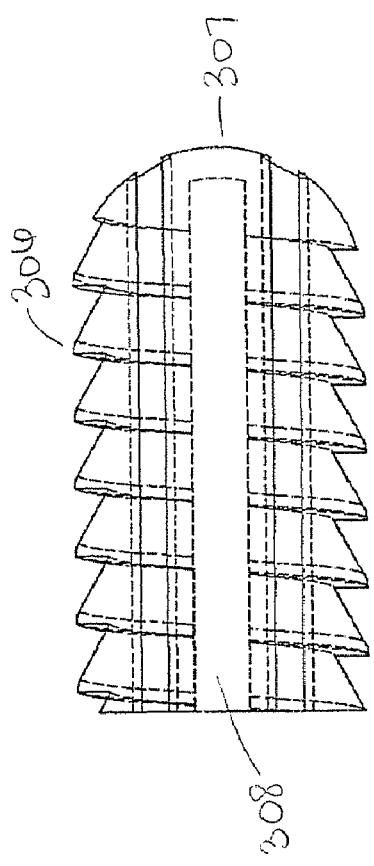
Figure 30B:
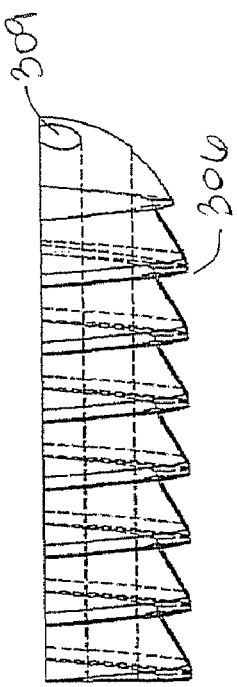

FIGS. 30A-30D are views of one embodiment of a bone segment having an external slotted groove 308. This embodiment can be used, for example in the BTB graft of FIGS. 29A-29B. FIG. 30A is a perspective view of one embodiment of a bone segment showing the threaded exterior surface characterized by threads 306, and omega shaped substantially parallel channels 309 on the tissue engaging surface of the bone segment. FIG. 30B is a side view of this embodiment of a bone segment showing its threaded exterior surface with threads 306 and omega-shaped channel 309. FIG. 30C is a view looking through the bone segment, showing threads 306 and external slotted groove 308 on the exterior surface. In this embodiment, the external slotted groove does not extent all the way to the edge of curved leading end 307. FIG. 30D is an end view showing the omega-shaped channels 309 of the tissue engaging surface and the external slotted groove 308 for slideably engaging an insertion tool. In this embodiment, external slotted groove 308 has a rectangular profile.

Figure 31A:
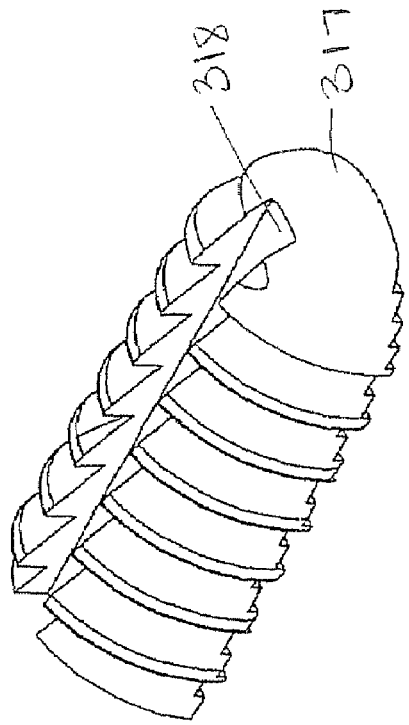
FIGS. 31A-31E are views of one embodiment of a second bone segment of a bone block of FIG. 29.
Figure 31C:
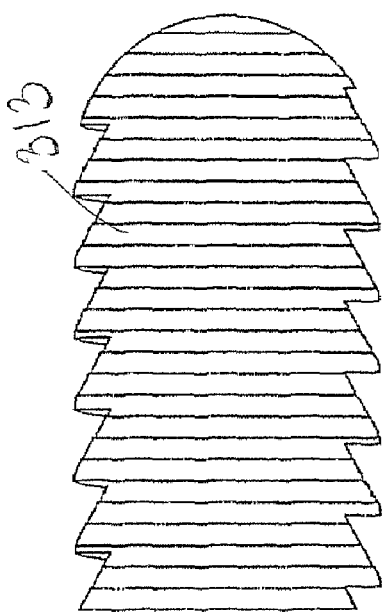
Figure 31B:
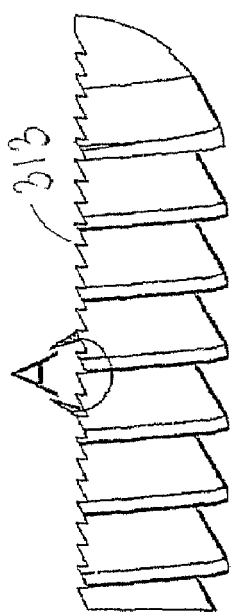
Figure 31D:
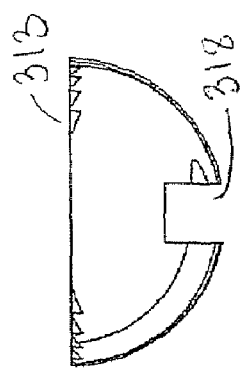
Figure 31E:

FIGS. 31A-31D are views of one embodiment of a bone segment with a textured tissue engaging surface, and having an external slotted groove 318. This embodiment can be used, for example, in the BTB graft of FIGS. 29A-29B. In a preferred embodiment, the bone segment of FIGS. 31A-31D would be used with the bone segment of FIGS. 30A-30D, with the end of a tendon sandwiched therebetween, as a leading and/or trailing bone block of a BTB graft. FIG. 31A is a perspective view of one embodiment of a bone segment having an external slotted groove 318, and threads on the exterior surface of the bone segment. FIG. 31B is a side view of the bone segment showing its threaded exterior surface, and rows of ridges 313 on the tissue engaging surface, wherein the ridges are angled against the direction of pull of the tendon. FIG. 31C is a bottom view of the bone segment showing the rows of angled ridges 313 on its tissue (tendon) engaging surface. FIG. 31D is and end view of the bone segment showing external slotted groove 318 for slideably engaging prongs or pins of an insertion tool, and the ridges 313 of the textured tissue engaging surface. In this embodiment, the external slotted groove shown has a rectangular profile. FIG. 31E is a detail blow up of Section A of FIG. 31B, showing the ridges 313 of the textured tissue engaging surface.

Figure 32A:
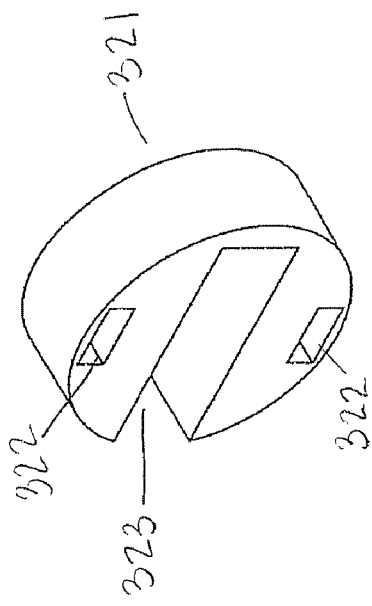
FIGS. 32A-32D are views of one embodiment of a tendon tensioner or spacer block for spacing opposing assembled bone blocks and applying tension to the tendon in embodiments of self fixing assembled BTB grafts of FIG. 29.
Figure 32D:
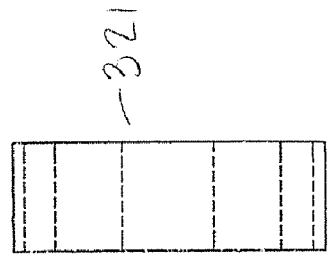
Figure 32C:
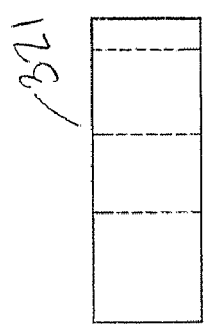
Figure 32B:
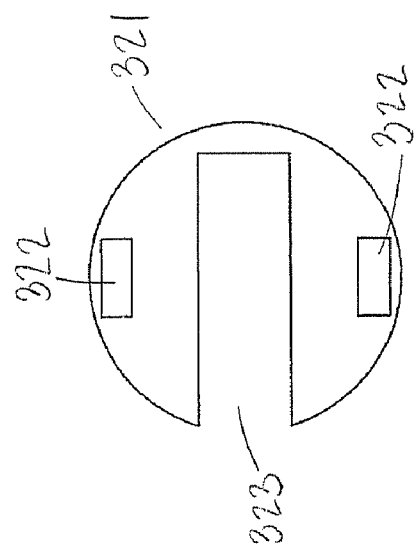

FIGS. 32A-32D are views of one embodiment of a tensioner member for applying tension to the tendon in the self fixing assembled BTB of the present invention. FIG. 32A is a perspective view of one member that would preferably be used as a pair of members that would be used in conjunction, with one member at (whether or not in contact with) the lagging end of the leading bone block and one at the leading end of the trailing bone bock, in tensioning the tendon. The tensioner member has an overall circular profile, with notch 323 interrupting the continuity of the circle. Notch 323 has a rectangular profile, and would slidably receive the tendon such that the top and bottom surfaces of the notch would engage the top and bottom surfaces of the tendon, respectively. The tensioner member has internal slotted grooves 322 therethrough for receiving the prongs or pins of an insertion tool. In a preferred embodiment, slotted grooves 322 are in aligned with corresponding slotted grooves in a first and/or second bone block when the BTB implant is assembled and mounted on the insertion tool. FIG. 32B is a front view of one tensioner member showing internal slotted grooves 322 for engaging the prongs of an insertion tool and notch 323 for accommodating the tendon. FIG. 32C is a horizontal side view of a tendon tensioner member. The two tensioner members that would be used in conjunction can be the same or different, and may be configured to hold tension on their own by resisting movement along the inserter prongs or pins, or may be configured to work with any one of the tensioners disclosed in FIG. 4 or 20 as an endcap or retainer between tensioner(s) and bone block(s).

FIGS. 33A-33D are views of one embodiment of a hand operated insertion tool for inserting (threading) the leading block of the self fixing assembled BTB of the present invention into a tapped (threaded) hole in a femur and simultaneously inserting the trailing block into the tapped (threaded) bone tunnel in the tibia of the recipient patient. FIG. 33A is a perspective view of one embodiment of an insertion tool having a shaft 331, a cross handle 332 and two prongs 333 having a rectangular profile. The rectangular profile of the prongs of this embodiment correspond to the aligned external slotted grooves of the BTB graft of FIGS. 29A-29B and the notches of the tensioner members shown in FIGS. 32A-32D. FIGS. 33B and 33D are top and side views of the insertion tool. FIG. 33C is a head on view of the pronged end of the insertion tool showing the rectangular profile of the prongs 333.

FIG. 34A shows a BTB implant comprising a self fixing assembled BTB graft of FIGS. 29A-29B with two tensioner members of FIGS. 32A-32D in place, and the tensioned BTB graft slideably positioned on insertion tool of FIGS. 33A-33D for insertion (threading) into appropriately drilled, and preferably tapped, holes in the tibia and femur of a patient in need of tendon replacement, repair or augmentation. As shown, one end of tendon 347 is sandwiched between the bone segments of leading bone block 344 and the other end is sandwiched between the bone segments of trailing bone block 345. Leading bone block 344 has one tensioner member 346 at the lagging end thereof and another tensioner member is placed at the leading end of trailing bone block 345. The lagging end of trailing bone block 345 is near or abuts shaft 341 of the insertion tool. FIG. 34B shows an exploded view of the BTB implant comprising a self fixing assembled BTB graft of FIGS. 29A-29B, a pair of tensioners of FIGS. 26A-26D, and the insertion tool of FIGS. 27A-27D.

EXAMPLES

Implantation Procedures

The details of surgical procedures appropriate for use in implanting BTB implants and grafts of the present invention vary depending upon the specific application. One example of a suitable procedure is provided here.

With the knee in approximately 90 degrees of flexion an incision approximately 2 cm in length is made medial to and just below the tibial tuberosity. The soft tissue is retracted and a small diameter guide pin is driven through the incision proximally to exit through the natural insertion point of the ACL on the tibial plateau. Typically the guide pin is then utilized to direct larger drills along its course sequentially increasing the size of the tibial tunnel. The guide pin is then introduced into the tibial tunnel to pass though the intra-articular space to a point deep in the posterior portion of the intra-condylar notch at the point of the origin of the natural ACL. The guide pin is then driven into the metaphyisis of the femur in a lateral and anterior direction. The guide pin is again used to direct drills of larger diameters into the distal femur creating a blind tunnel 25-30 mm in depth. The guide pin is removed if it remains in the tunnel and a dilator may be employed to increase the diameter of the tunnels by compacting the bone of the tunnels. A tap corresponding to the implant in size and thread form is then inserted and turned in both the tibial tunnel and continued on into the femoral tunnel to form (cut) the threads needed to accept the graft into the tunnel. The tap is threaded back out and the pretensioned graft with tensioner and insertion tool is retrieved from the back table. Using the insertion tool, the leading end of the BTB graft is then threaded into the prepared tunnel of the tibia and threaded through the tibia to pass through the intra-articular space into and bottoming out in the prepared femoral tunnel. The insertion tool is withdrawn from the femoral bone plug, the tensioner is disengaged from the graft and inserter, then removed through the arthroscopy access portals, and the graft tension may be adjusted by turning the tibial bone plug up to a half turn left or right independently of the femoral bone plug. The incision is closed in standard fashion.

The surgical procedure requires precise placement of the tunnels to insure that the natural isometrics of the knee are maintained. Therefore the guide pins are generally placed with the assistance of fluoroscopy, arthroscopy and/or mechanical guides. Bone tunnels would be drilled approximately one millimeter less in diameter than the minor diameter of the implant thread form. The tunnels would then be dilated to the minor diameter and then tapped prior to inserting the implant.

Guides and dilators are commercially available.

While the invention has been described above with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A self fixing bone-tendon-bone (BTB) graft, said self fixing BTB graft comprising a length of graft tendon or ligament having two opposing ends, a first opposing end and a second opposing end, wherein a first bone block is attached to said first opposing end of said graft tendon or ligament and a second bone block is attached to said second opposing end of said graft tendon or ligament, and wherein at least one of said first bone block or said second bone block has an exterior surface having threads along at least a portion thereof, and a tensioner that forceably engages the first and second bone blocks positioned on opposing ends of the graft tendon or ligament to exert a tension on the graft tendon or ligament, wherein said tensioner and at least one of said first bone block or said second bone block each comprise at least one hole, slot, or groove in alignment for mounting on an inserter; and wherein said tensioner is disposed between the first bone block and the second bone block.

2. The self fixing BTB graft of claim 1, wherein each of said first bone block and said second bone block has an exterior surface having threads along at least a portion thereof, and wherein the threads of said first bone block and said second bone block run in the same direction so that each bone block is implantable in a respective hole in opposing bones of a joint on a patient when the self fixing BTB graft is rotated as a whole in the threaded direction.

3. The self fixing BTB graft of claim 2, wherein the threads on the first bone block have a smaller outer diameter than the threads on the second bone block.

4. The self fixing BTB graft of claim 2, wherein the threads on the first bone block have a diameter which varies along the length of the first bone block.

5. The self fixing BTB graft of claim 1, wherein the first bone block has an exterior surface having threads along at least a portion thereof, and the second bone block has an exterior surface that is substantially cylindrical, stepped, or tapered.

6. The self fixing BTB graft of claim 1, wherein said tensioner is integrated with an inserter.

7. The self fixing BTB graft of claim 1, wherein said tensioner is not integrated with an inserter.

8. The self fixing BTB graft of claim 1, wherein said tensioner is configured to bend, flex, or break away after implantation.

9. The self fixing BTB graft of claim 1, wherein said tensioner comprises a pair of spacers positioned on opposing sides of said graft tendon or ligament.

10. The self fixing BTB graft of claim 1, wherein said tensioner comprises a single spacer having a slot along its length for encasing said graft tendon or ligament.

11. The self fixing BTB graft of claim 2, wherein the outside surface of said tensioner is threaded with threads running in the same direction as the threads on said first bone block or on said second bone block.

12. The self fixing BTB graft of claim 11, wherein the threads on the surface of said tensioner are contiguous with the threads on said first bone block or on said second bone block.

13. The self fixing BTB graft of claim 1, wherein said first bone block is an assembled bone block sandwiching the first opposing end of said graft tendon or ligament.

14. The self fixing BTB graft of claim 1 wherein said first bone block and said second bone block comprise the same or different materials and said materials are selected from the group consisting of cortical bone, cortical-cancellous bone, cancellous bone, calcium phosphate ceramic, hydroxy apatite, synthetic bone, and combinations thereof.

15. The self fixing BTB graft of claim 14, wherein said first bone block and said second bone block comprise cortical bone.

16. The self fixing BTB graft of claim 15, wherein said first bone block comprises a first bone segment comprising cortical bone and a second bone segment comprising cortical bone that sandwich the first end of said graft tendon or ligament; and said second bone block comprises a third bone segment comprising cortical bone and a fourth bone segment comprising cortical bone that sandwich the second end of said graft tendon or ligament.

17. The self fixing BTB graft of claim 16, wherein said first bone segment comprising cortical bone and said second bone segment comprising cortical bone each have a graft tendon or ligament engaging surface that is textured for gripping the end of said graft tendon or ligament.

18. The self fixing BTB graft of claim 17, wherein the graft tendon or ligament engaging surface of said first bone segment comprising cortical bone comprises compression surfaces and one to ten cavities.

19. The self fixing BTB graft of claim 18, wherein said one to ten cavities comprise one to ten channels.

20. The self fixing BTB graft of claim 19, wherein at least one of said channels comprise a cross-sectional profile selected from the group consisting of dovetail, omega-shaped and a combination thereof.

21. The self fixing BTB graft of claim 20, wherein at least one of said channels has an omega-shaped cross-sectional profile.

22. The self fixing BTB graft of claim 16, wherein said graft tendon or ligament engaging surface of said second bone segment comprising cortical bone comprises rows of ridges that angle opposite the direction of pull of said graft tendon or ligament.

23. The self fixing BTB graft of claim 1, wherein said self fixing BTB graft is perfused or coated with an osteoinductive substance.

24. A self fixing bone-tendon-bone (BTB) graft for implantation through a tibial tunnel, said self fixing BTB graft comprising a length of graft tendon or ligament having two opposing ends, a first opposing end and a second opposing end, said first opposing end having a leading bone block attached thereto, said second opposing end having a trailing bone block attached thereto, said leading bone block and said trailing bone block each having an exterior surface that is threaded so that the threads run in the same direction, whereby the leading bone block and the trailing bone block are suited for simultaneous threading into tapped holes in a patient's femur and tibia, respectively; wherein said self fixing bone-tendon-bone (BTB) graft further comprises a tensioner that wraps around and protects said graft tendon or ligament, and forcibly engages said leading and trailing bone blocks to hold said bone blocks a distance from one another; and wherein said tensioner is disposed between the leading bone block and the trailing bone block.

25. The self fixing BTB graft of claim 24, wherein the threaded surface is aligned between the leading bone block and the trailing bone block.

26. The self fixing BTB graft of claim 25, wherein the leading bone block has a smaller diameter than the trailing bone block.

27. The self fixing BTB graft of claim 25, wherein said leading bone block is an assembled bone block.

28. The self fixing BTB graft of claim 27, wherein said length of graft tendon or ligament is a bundle of one to ten graft tendons or ligaments having a first end and a second end.

29. The self fixing BTB graft of claim 25, wherein said trailing bone block is an assembled bone block.

30. The self fixing BTB graft of claim 25, wherein said leading bone block, said length of graft tendon or ligament, and said trailing bone block are allograft, xenograft or a combination thereof.

31. The self fixing BTB graft of claim 30, wherein said leading bone block, said length of graft tendon or ligament, and said trailing bone block are allograft.

32. The self fixing BTB graft of claim 30, wherein said leading bone block, said length of graft tendon or ligament, and said trailing bone block are xenograft.

33. The self fixing BTB graft of claim 30, wherein said leading bone block, said length of graft tendon or ligament, and said trailing bone block are a combination of allograft and xenograft.

34. An assembled self fixing bone-tendon-bone (BTB) graft for implantation through a tibial tunnel, the self fixing BTB graft comprising a length of graft tendon or ligament having two opposing ends, a first opposing end and a second opposing end, the first opposing end having a leading bone block assembly attached thereto, the second opposing end having a trailing bone block assembly attached thereto, the leading bone block assembly and the trailing bone block assembly each comprising a substantially cylindrical cross-section, and a tensioner disposed between the leading bone block assembly and the trailing bone block assembly; the tensioner configured to maintain tension in the graft tendon or ligament and spacing between the two bone block assemblies during implantation by forceably engaging said leading and trailing bone block assemblies to hold said bone block assemblies a distance from one another, and wherein said tensioner and at least one of said bone blocks each comprise at least one hole, slot, or groove in alignment for mounting on an insertion tool.

* * * * *